US009604055B2

(12) United States Patent
Mercanzini et al.

(10) Patent No.: US 9,604,055 B2
(45) Date of Patent: Mar. 28, 2017

(54) MICROFABRICATED SURFACE NEUROSTIMULATION DEVICE AND METHODS OF MAKING AND USING THE SAME

(71) Applicant: ECOLE POLYTECHNIQUE FEDERALE DE LAUSANNE, Lausanne (CH)

(72) Inventors: André Mercanzini, Saint Sulpice (CH); Philippe Renaud, Préverenges (CH)

(73) Assignee: ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 0 days.

(21) Appl. No.: 14/945,952

(22) Filed: Nov. 19, 2015

(65) Prior Publication Data

US 2016/0074655 A1    Mar. 17, 2016

Related U.S. Application Data

(63) Continuation of application No. 14/287,917, filed on May 27, 2014, now Pat. No. 9,192,767, which is a (Continued)

(51) Int. Cl.
*A61N 1/36*    (2006.01)
*A61B 5/04*    (2006.01)
(Continued)

(52) U.S. Cl.
CPC ........ *A61N 1/3606* (2013.01); *A61B 5/04001* (2013.01); *A61B 5/0478* (2013.01);
(Continued)

(58) Field of Classification Search
None
See application file for complete search history.

(56) References Cited

U.S. PATENT DOCUMENTS 4,245,645 A    1/1981    Arseneault et al.
4,550,733 A    11/1985   Liss et al.
(Continued)

FOREIGN PATENT DOCUMENTS

EP    0 677 743    10/1995
EP    0 743 839    11/1996
(Continued)

OTHER PUBLICATIONS

US 8,388,533, 03/2013, Hafezi et al. (withdrawn)
(Continued)

*Primary Examiner* — Brian T Gedeon
(74) *Attorney, Agent, or Firm* — Foley & Lardner LLP; James De Vellis

(57) ABSTRACT

Described herein are microelectrode array devices, and methods of fabrication and use of the same, to provide highly localized and efficient electrical stimulation of a neurological target. The device includes multiple microelectrode elements arranged along an supportive backing layer. The microelectrode elements are dimensioned and shaped so as to target individual neurons, groups of neurons, and neural tissue as may be located in an animal nervous system, such as along a region of a cortex of a human brain. Beneficially, the neurological probe can be used to facilitate location of the neurological target and remain implanted for long-term monitoring and/or stimulation.

19 Claims, 49 Drawing Sheets

Related U.S. Application Data continuation of application No. 13/512,936, filed as application No. PCT/EP2010/068658 on Dec. 1, 2010, now Pat. No. 8,774,937.

(60) Provisional application No. 61/265,725, filed on Dec. 1, 2009.

(51) Int. Cl.
  *A61N 1/05* (2006.01)
  *A61B 5/0478* (2006.01)
  *A61B 5/00* (2006.01)
  *A61N 1/372* (2006.01)

(52) U.S. Cl.
  CPC ............ *A61B 5/685* (2013.01); *A61B 5/6846* (2013.01); *A61N 1/0531* (2013.01); *A61N 1/0539* (2013.01); *A61N 1/36082* (2013.01); *A61N 1/36125* (2013.01); *A61N 1/36185* (2013.01); *A61N 1/37211* (2013.01); *A61B 2562/028* (2013.01); *A61B 2562/0209* (2013.01); *A61B 2562/046* (2013.01); *A61B 2562/125* (2013.01); *Y10T 29/49147* (2015.01)

(56) References Cited

U.S. PATENT DOCUMENTS

| | | |
|---|---|---|
| 4,837,049 A | 6/1989 | Byers et al. |
| 4,917,093 A | 4/1990 | Dufresne et al. |
| 4,928,297 A | 5/1990 | Tsutsui et al. |
| 4,969,468 A | 11/1990 | Byers et al. |
| 4,989,617 A | 2/1991 | Memberg et al. |
| 5,215,088 A | 6/1993 | Normann et al. |
| 5,391,250 A | 2/1995 | Cheney et al. |
| 5,400,784 A | 3/1995 | Durand et al. |
| 5,419,777 A | 5/1995 | Hofling |
| 5,496,369 A | 3/1996 | Howard, III |
| 5,524,338 A | 6/1996 | Martyniuk et al. |
| 5,628,317 A | 5/1997 | Starkebaum et al. |
| 5,643,330 A | 7/1997 | Holsheimer et al. |
| 5,679,355 A | 10/1997 | Alexander et al. |
| 5,683,422 A | 11/1997 | Rise |
| 5,697,651 A | 12/1997 | Fernandes |
| 5,697,975 A | 12/1997 | Howard et al. |
| 5,702,429 A | 12/1997 | King |
| 5,713,922 A | 2/1998 | King |
| 5,713,923 A | 2/1998 | Ward et al. |
| 5,716,377 A | 2/1998 | Rise et al. |
| 5,727,552 A | 3/1998 | Ryan |
| 5,752,979 A | 5/1998 | Benabid |
| 5,755,759 A | 5/1998 | Cogan |
| 5,782,798 A | 7/1998 | Rise |
| 5,792,186 A | 8/1998 | Rise |
| 5,797,970 A | 8/1998 | Pouvreau |
| 5,800,474 A | 9/1998 | Benabid et al. |
| 5,800,535 A | 9/1998 | Howard, III |
| 5,814,092 A | 9/1998 | King |
| 5,824,029 A | 10/1998 | Weijand et al. |
| 5,833,709 A | 11/1998 | Rise et al. |
| 5,833,714 A | 11/1998 | Loeb |
| 5,843,148 A | 12/1998 | Gijsbers et al. |
| 5,893,883 A | 4/1999 | Torgerson et al. |
| 5,913,882 A | 6/1999 | King |
| 5,921,924 A | 7/1999 | Avitall |
| 5,927,277 A | 7/1999 | Baudino et al. |
| 5,941,906 A | 8/1999 | Barreras et al. |
| 5,957,958 A | 9/1999 | Schulman et al. |
| 5,975,085 A | 11/1999 | Rise |
| 5,978,702 A | 11/1999 | Ward et al. |
| 5,991,668 A | 11/1999 | Leinders et al. |
| 6,011,996 A | 1/2000 | Gielen et al. |
| 6,018,682 A | 1/2000 | Rise |
| 6,024,095 A | 2/2000 | Stanley, III |
| 6,033,403 A | 3/2000 | Tu et al. |
| 6,038,480 A | 3/2000 | Hrdlicka et al. |
| 6,050,992 A | 4/2000 | Nichols |
| 6,094,598 A | 7/2000 | Elsberry et al. |
| 6,104,960 A | 8/2000 | Duysens et al. |
| 6,109,269 A | 8/2000 | Rise et al. |
| 6,125,300 A | 9/2000 | Weijand et al. |
| 6,128,537 A | 10/2000 | Rise |
| 6,129,685 A | 10/2000 | Howard, III |
| 6,161,047 A | 12/2000 | King et al. |
| 6,205,359 B1 | 3/2001 | Boveja |
| 6,205,361 B1 | 3/2001 | Kuzma et al. |
| 6,216,043 B1 | 4/2001 | Swanson et al. |
| 6,227,203 B1 | 5/2001 | Rise et al. |
| 6,253,109 B1 | 6/2001 | Gielen |
| 6,253,110 B1 | 6/2001 | Brabec et al. |
| 6,263,237 B1 | 7/2001 | Rise |
| 6,266,564 B1 | 7/2001 | Hill et al. |
| 6,295,476 B1 | 9/2001 | Schaenzer |
| 6,319,241 B1 | 11/2001 | King et al. |
| 6,330,466 B1 | 12/2001 | Hofmann et al. |
| 6,337,997 B1 | 1/2002 | Rise |
| 6,343,226 B1 | 1/2002 | Sunde et al. |
| 6,353,762 B1 | 3/2002 | Baudino et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,364,875 B1 | 4/2002 | Stanley, III |
| 6,366,813 B1 | 4/2002 | DiLorenzo |
| 6,374,140 B1 | 4/2002 | Rise |
| 6,375,666 B1 | 4/2002 | Mische |
| 6,379,353 B1 | 4/2002 | Nichols |
| 6,415,187 B1 | 7/2002 | Kuzma et al. |
| 6,434,431 B1 | 8/2002 | Camps et al. |
| 6,479,999 B1 | 11/2002 | DeMeester et al. |
| 6,484,059 B2 | 11/2002 | Gielen |
| 6,493,590 B1 | 12/2002 | Wessman et al. |
| 6,529,774 B1 | 3/2003 | Greene |
| 6,538,443 B2 | 3/2003 | Morich et al. |
| 6,549,812 B1 | 4/2003 | Smits |
| 6,556,873 B1 | 4/2003 | Smits |
| 6,560,472 B2 | 5/2003 | Hill et al. |
| 6,560,486 B1 | 5/2003 | Osorio et al. |
| 6,587,733 B1 | 7/2003 | Cross et al. |
| 6,591,128 B1 | 7/2003 | Wu et al. |
| 6,594,524 B2 | 7/2003 | Esteller et al. |
| 6,597,953 B2 | 7/2003 | Boling |
| 6,643,552 B2 | 11/2003 | Edell et al. |
| 6,671,544 B2 | 12/2003 | Baudino |
| 6,675,046 B2 | 1/2004 | Holsheimer |
| 6,687,538 B1 | 2/2004 | Hrdlicka et al. |
| 6,690,973 B2 | 2/2004 | Hill et al. |
| 6,708,064 B2 | 3/2004 | Rezai |
| 6,718,208 B2 | 4/2004 | Hill et al. |
| 6,718,211 B2 | 4/2004 | Smits |
| 6,741,893 B2 | 5/2004 | Smits |
| 6,745,079 B2 | 6/2004 | King |
| 6,757,970 B1 | 7/2004 | Kuzma et al. |
| 6,795,737 B2 | 9/2004 | Gielen et al. |
| 6,804,552 B2 | 10/2004 | Thompson et al. |
| 6,818,396 B1 | 11/2004 | Bloch et al. |
| 6,829,498 B2 | 12/2004 | Kipke et al. |
| 6,850,802 B2 | 2/2005 | Holsheimer |
| 6,871,098 B2 | 3/2005 | Nuttin et al. |
| 6,882,881 B1 | 4/2005 | Lesser et al. |
| 6,892,097 B2 | 5/2005 | Holsheimer |
| 6,892,438 B1 | 5/2005 | Hill et al. |
| 6,904,306 B1 | 6/2005 | Wu et al. |
| 6,909,920 B2 | 6/2005 | Lokhoff et al. |
| 6,920,359 B2 | 7/2005 | Meadows et al. |
| 6,928,320 B2 | 8/2005 | King |
| 6,950,706 B2 | 9/2005 | Rodriguez et al. |
| 6,950,709 B2 | 9/2005 | Baudino |
| 6,978,171 B2 | 12/2005 | Goetz et al. |
| 6,978,178 B2 | 12/2005 | Sommer et al. |
| 6,999,819 B2 | 2/2006 | Swoyer et al. |
| 7,006,859 B1 | 2/2006 | Osorio et al. |
| 7,010,351 B2 | 3/2006 | Firlik et al. |
| 7,010,356 B2 | 3/2006 | Jog et al. |
| 7,024,246 B2 | 4/2006 | Acosta et al. |

(56) References Cited

U.S. PATENT DOCUMENTS

| | | |
|---|---|---|
| 7,035,690 B2 | 4/2006 | Goetz |
| 7,047,082 B1 | 5/2006 | Schrom et al. |
| 7,047,084 B2 | 5/2006 | Erickson et al. |
| 7,050,856 B2 | 5/2006 | Stypulkowski |
| 7,051,419 B2 | 5/2006 | Schrom et al. |
| 7,061,240 B2 | 6/2006 | Ham et al. |
| 7,063,767 B1 | 6/2006 | Tyson et al. |
| 7,076,292 B2 | 7/2006 | Forsberg |
| 7,077,822 B1 | 7/2006 | Howard, III |
| 7,107,104 B2 | 9/2006 | Keravel et al. |
| 7,133,718 B2 | 11/2006 | Bakken et al. |
| 7,146,222 B2 | 12/2006 | Boling |
| 7,151,961 B1 | 12/2006 | Whitehurst et al. |
| 7,174,219 B2 | 2/2007 | Wahlstrand et al. |
| 7,177,701 B1 | 2/2007 | Pianca |
| 7,181,288 B1 | 2/2007 | Rezai et al. |
| 7,184,829 B2 | 2/2007 | Hill et al. |
| 7,187,978 B2 | 3/2007 | Malek et al. |
| 7,191,016 B2 | 3/2007 | Marshall et al. |
| 7,191,018 B2 | 3/2007 | Gielen et al. |
| 7,200,439 B2 | 4/2007 | Zdeblick et al. |
| 7,203,548 B2 | 4/2007 | Whitehurst et al. |
| 7,204,798 B2 | 4/2007 | Zdeblick et al. |
| 7,204,833 B1 | 4/2007 | Osorio et al. |
| 7,209,787 B2 | 4/2007 | DiLorenzo |
| 7,212,851 B2 | 5/2007 | Donoghue et al. |
| 7,212,867 B2 | 5/2007 | Van Venrooij et al. |
| 7,214,189 B2 | 5/2007 | Zdeblick |
| 7,216,000 B2 | 5/2007 | Sieracki et al. |
| 7,216,001 B2 | 5/2007 | Hacker et al. |
| 7,231,256 B2 | 6/2007 | Wahlstrand et al. |
| 7,236,822 B2 | 6/2007 | Dobak, III |
| 7,242,984 B2 | 7/2007 | DiLorenzo |
| 7,276,061 B2 | 10/2007 | Schaer et al. |
| 7,280,867 B2 | 10/2007 | Frei et al. |
| 7,282,030 B2 | 10/2007 | Frei et al. |
| 7,282,050 B2 | 10/2007 | Starkebaum et al. |
| 7,286,878 B2 | 10/2007 | Stypulkowski |
| 7,286,882 B2 | 10/2007 | Cole |
| 7,288,066 B2 | 10/2007 | Drew |
| 7,289,851 B2 | 10/2007 | Gunderson et al. |
| 7,289,852 B2 | 10/2007 | Helfinstine et al. |
| 7,295,880 B2 | 11/2007 | Gielen |
| 7,298,143 B2 | 11/2007 | Jaermann et al. |
| 7,307,223 B2 | 12/2007 | Tyson et al. |
| 7,313,430 B2 | 12/2007 | Urquhart et al. |
| 7,313,440 B2 | 12/2007 | Miesel |
| 7,315,759 B2 | 1/2008 | Markowitz et al. |
| 7,317,947 B2 | 1/2008 | Wahlstrand et al. |
| 7,317,948 B1 | 1/2008 | King et al. |
| 7,319,899 B2 | 1/2008 | Keizer |
| 7,319,904 B2 | 1/2008 | Cross et al. |
| 7,321,798 B2 | 1/2008 | Muhlenberg et al. |
| 7,321,837 B2 | 1/2008 | Osorio et al. |
| 7,322,832 B2 | 1/2008 | Kronich et al. |
| 7,328,057 B2 | 2/2008 | Freas et al. |
| 7,328,068 B2 | 2/2008 | Spinelli et al. |
| 7,328,069 B2 | 2/2008 | Gerber |
| 7,330,760 B2 | 2/2008 | Heruth et al. |
| 7,337,010 B2 | 2/2008 | Howard et al. |
| 7,343,206 B2 | 3/2008 | Sage et al. |
| 7,346,395 B2 | 3/2008 | Lozano et al. |
| 7,356,369 B2 | 4/2008 | Phillips et al. |
| 7,359,837 B2 | 4/2008 | Drew |
| 7,366,572 B2 | 4/2008 | Heruth et al. |
| 7,367,956 B2 | 5/2008 | King |
| 7,369,891 B2 | 5/2008 | Augustijn et al. |
| 7,369,893 B2 | 5/2008 | Gunderson |
| 7,369,894 B2 | 5/2008 | Gerber |
| 7,385,443 B1 | 6/2008 | Denison |
| 7,388,378 B2 | 6/2008 | Gray et al. |
| 7,389,147 B2 | 6/2008 | Wahlstrand et al. |
| 7,390,311 B2 | 6/2008 | Hildebrand et al. |
| 7,391,257 B1 | 6/2008 | Denison et al. |
| 7,392,089 B2 | 6/2008 | Wahlstrand et al. |
| 7,395,113 B2 | 7/2008 | Heruth et al. |
| 7,400,927 B1 | 7/2008 | Litvin |
| 7,406,351 B2 | 7/2008 | Wesselink |
| 7,418,292 B2 | 8/2008 | Shafer |
| 7,421,297 B2 | 9/2008 | Giftakis et al. |
| 7,427,280 B2 | 9/2008 | Gerber |
| 7,429,938 B1 | 9/2008 | Corndorf |
| 7,433,734 B2 | 10/2008 | King |
| 7,442,183 B2 | 10/2008 | Baudino et al. |
| 7,447,545 B2 | 11/2008 | Heruth et al. |
| 7,450,996 B2 | 11/2008 | MacDonald et al. |
| 7,463,917 B2 | 12/2008 | Martinez |
| 7,463,928 B2 | 12/2008 | Lee et al. |
| 7,474,247 B1 | 1/2009 | Heinks et al. |
| 7,479,910 B1 | 1/2009 | Heinks et al. |
| 7,483,748 B2 | 1/2009 | Torgerson et al. |
| 7,489,966 B2 | 2/2009 | Leinders et al. |
| 7,489,970 B2 | 2/2009 | Lee et al. |
| 7,491,181 B2 | 2/2009 | Heruth et al. |
| 7,497,844 B2 | 3/2009 | Spear et al. |
| 7,497,863 B2 | 3/2009 | Solar et al. |
| 7,502,217 B2 | 3/2009 | Zhao et al. |
| 7,505,815 B2 | 3/2009 | Lee et al. |
| 7,505,869 B2 | 3/2009 | Hartlaub |
| 7,515,961 B2 | 4/2009 | Germanson et al. |
| 7,519,431 B2 | 4/2009 | Goetz et al. |
| 7,519,432 B2 | 4/2009 | Bolea et al. |
| 7,520,890 B2 | 4/2009 | Phillips |
| 7,526,339 B2 | 4/2009 | Lahti et al. |
| 7,526,340 B2 | 4/2009 | Drew |
| 7,526,341 B2 | 4/2009 | Goetz et al. |
| 7,529,582 B1 | 5/2009 | DiLorenzo |
| 7,529,586 B2 | 5/2009 | Wahlstrand et al. |
| 7,542,803 B2 | 6/2009 | Heruth et al. |
| 7,546,164 B2 | 6/2009 | King |
| 7,546,166 B2 | 6/2009 | Michels et al. |
| 7,548,775 B2 | 6/2009 | Kipke et al. |
| 7,548,786 B2 | 6/2009 | Lee et al. |
| 7,551,951 B1 | 6/2009 | Osorio et al. |
| 7,551,960 B2 | 6/2009 | Forsberg et al. |
| 7,555,345 B2 | 6/2009 | Wahlstrand et al. |
| 7,561,921 B2 | 7/2009 | Phillips et al. |
| 7,563,141 B2 | 7/2009 | Alexander et al. |
| 7,563,541 B2 | 7/2009 | Howard et al. |
| 7,578,819 B2 | 8/2009 | Bleich et al. |
| 7,580,756 B2 | 8/2009 | Schulte et al. |
| 7,582,387 B2 | 9/2009 | Howard et al. |
| 7,590,451 B2 | 9/2009 | Tronnes et al. |
| 7,590,453 B2 | 9/2009 | Heruth et al. |
| 7,590,455 B2 | 9/2009 | Heruth et al. |
| 7,591,970 B2 | 9/2009 | Olson |
| 7,594,828 B2 | 9/2009 | Alexander et al. |
| 7,594,889 B2 | 9/2009 | St. Ores et al. |
| 7,596,399 B2 | 9/2009 | Singhal et al. |
| 7,596,408 B2 | 9/2009 | Singhal et al. |
| 7,596,415 B2 | 9/2009 | Brabec et al. |
| 7,599,730 B2 | 10/2009 | Hunter et al. |
| 7,603,161 B2 | 10/2009 | Wurmfeld et al. |
| 7,603,177 B2 | 10/2009 | Sieracki et al. |
| 7,604,629 B2 | 10/2009 | Gerber et al. |
| 7,604,644 B2 | 10/2009 | Schulte et al. |
| 7,608,458 B2 | 10/2009 | Soykan et al. |
| 7,610,083 B2 | 10/2009 | Drew et al. |
| 7,611,483 B2 | 11/2009 | Gerber et al. |
| 7,614,743 B2 | 11/2009 | Geiger |
| 7,615,015 B2 | 11/2009 | Coleman |
| 7,616,998 B2 | 11/2009 | Nuttin et al. |
| 7,617,002 B2 | 11/2009 | Goetz |
| 7,620,454 B2 | 11/2009 | Dinsmoor et al. |
| 7,622,303 B2 | 11/2009 | Soykan et al. |
| 7,622,988 B2 | 11/2009 | Denison et al. |
| 7,623,053 B2 | 11/2009 | Terry et al. |
| 7,623,918 B2 | 11/2009 | Goetz |
| 7,623,919 B2 | 11/2009 | Goetz et al. |
| 7,623,923 B2 | 11/2009 | Gerber et al. |
| 7,623,930 B2 | 11/2009 | Zeijlemaker et al. |
| 7,624,293 B2 | 11/2009 | Osorio et al. |
| 7,628,780 B2 | 12/2009 | Bonner et al. |
| 7,631,415 B2 | 12/2009 | Phillips et al. |

(56) References Cited

U.S. PATENT DOCUMENTS

| | | |
|---|---|---|
| 7,632,225 B2 | 12/2009 | Stypulkowski |
| 7,635,541 B2 | 12/2009 | Scott et al. |
| 7,637,867 B2 | 12/2009 | Zdeblick |
| 7,640,059 B2 | 12/2009 | Forsberg et al. |
| 7,640,060 B2 | 12/2009 | Zdeblick |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,663,066 B2 | 2/2010 | Tyson et al. |
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,713,194 B2 | 5/2010 | Zdeblick |
| 7,713,195 B2 | 5/2010 | Zdeblick |
| 7,720,548 B2 | 5/2010 | King |
| 7,729,768 B2 | 6/2010 | White et al. |
| 7,729,780 B2 | 6/2010 | Vardiman |
| 7,738,958 B2 | 6/2010 | Zdeblick et al. |
| 7,742,823 B2 | 6/2010 | King et al. |
| 7,756,588 B2 | 7/2010 | Jog et al. |
| 7,797,029 B2 | 9/2010 | Gibson et al. |
| 7,822,483 B2 | 10/2010 | Stone et al. |
| 7,853,303 B2 | 12/2010 | Nikumb et al. |
| 7,877,149 B2 | 1/2011 | Zdeblick |
| 7,899,539 B2 | 3/2011 | Whitehurst et al. |
| 7,925,329 B2 | 4/2011 | Zdeblick et al. |
| 7,930,035 B2 | 4/2011 | DiLorenzo |
| 7,935,056 B2 | 5/2011 | Zdeblick |
| 7,941,202 B2 | 5/2011 | Hetke et al. |
| 7,945,336 B2 | 5/2011 | Sauter-Starace et al. |
| 7,969,161 B2 | 6/2011 | Behzadi et al. |
| 7,974,705 B2 | 7/2011 | Zdeblick et al. |
| 7,978,064 B2 | 7/2011 | Zdeblick et al. |
| 7,979,105 B2 | 7/2011 | Kipke et al. |
| 7,983,751 B2 | 7/2011 | Zdeblick et al. |
| 8,000,794 B2 | 8/2011 | Lozano |
| 8,000,808 B2 | 8/2011 | Hegland et al. |
| 8,032,224 B2 | 10/2011 | Miesel et al. |
| 8,036,737 B2 | 10/2011 | Goetz et al. |
| 8,036,743 B2 | 10/2011 | Savage et al. |
| 8,036,748 B2 | 10/2011 | Zdeblick et al. |
| 8,055,334 B2 | 11/2011 | Savage et al. |
| 8,055,353 B2 | 11/2011 | Kreidler et al. |
| 8,099,170 B2 | 1/2012 | Jensen et al. |
| 8,114,021 B2 | 2/2012 | Robertson et al. |
| 8,115,618 B2 | 2/2012 | Robertson et al. |
| 8,121,687 B2 | 2/2012 | Jensen et al. |
| 8,123,684 B2 | 2/2012 | Zdeblick |
| 8,172,762 B2 | 5/2012 | Robertson |
| 8,187,161 B2 | 5/2012 | Li et al. |
| 8,195,308 B2 | 6/2012 | Frank et al. |
| 8,204,586 B2 | 6/2012 | Zdeblick |
| 8,258,962 B2 | 9/2012 | Robertson et al. |
| 8,261,428 B2 | 9/2012 | Fang et al. |
| 8,280,514 B2 | 10/2012 | Lozano et al. |
| 8,332,020 B2 | 12/2012 | Zdeblick |
| 8,355,768 B2 | 1/2013 | Masmanidis et al. |
| 8,412,347 B2 | 4/2013 | Zdeblick |
| 8,473,061 B2 | 6/2013 | Moffitt et al. |
| 8,473,069 B2 | 6/2013 | Bi et al. |
| 8,489,203 B2 | 7/2013 | Ortmann |
| 8,788,064 B2 | 7/2014 | Mercanzini et al. |
| 8,874,232 B2 | 10/2014 | Chen |
| 8,897,891 B2 | 11/2014 | Romero |
| 8,938,308 B2 | 1/2015 | Meadows |
| 2002/0062143 A1 | 5/2002 | Baudino et al. |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0060822 A1 | 3/2003 | Schaer et al. |
| 2003/0083724 A1 | 5/2003 | Jog et al. |
| 2003/0100823 A1 | 5/2003 | Kipke et al. |
| 2003/0135253 A1 | 7/2003 | Kokones et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 | 2/2004 | Schrom et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1 | 12/2004 | Plaza |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 | 1/2005 | DiLorenzo |
| 2005/0027284 A1 | 2/2005 | Lozano et al. |
| 2005/0033136 A1 | 2/2005 | Govari et al. |
| 2005/0038489 A1 | 2/2005 | Grill |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154425 A1 | 7/2005 | Boveja et al. |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 | 10/2005 | Przybyszewski et al. |
| 2005/0240242 A1 | 10/2005 | DiLorenzo |
| 2005/0245988 A1 | 11/2005 | Miesel |
| 2006/0004422 A1 | 1/2006 | De Ridder |
| 2006/0030897 A1 | 2/2006 | Gilmer et al. |
| 2006/0041295 A1 | 2/2006 | Osypka |
| 2006/0049957 A1 | 3/2006 | Surgenor et al. |
| 2006/0058588 A1 | 3/2006 | Zdeblick |
| 2006/0058727 A1 | 3/2006 | Bernabei |
| 2006/0058855 A1 | 3/2006 | Gill |
| 2006/0095105 A1 | 5/2006 | Jog et al. |
| 2006/0116581 A1 | 6/2006 | Zdeblick et al. |
| 2006/0129203 A1 | 6/2006 | Garabedian et al. |
| 2006/0135877 A1 | 6/2006 | Giftakis et al. |

(56) References Cited

U.S. PATENT DOCUMENTS

| | | |
|---|---|---|
| 2006/0149336 A1 | 7/2006 | Meadows |
| 2006/0149337 A1 | 7/2006 | John |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0276866 A1 | 12/2006 | McCreery |
| 2006/0282014 A1 | 12/2006 | Kipke et al. |
| 2006/0293720 A1 | 12/2006 | DiLorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0027540 A1 | 1/2008 | Cumming |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1 | 5/2008 | Gerber |
| 2008/0114417 A1 | 5/2008 | Leyde |
| 2008/0119900 A1 | 5/2008 | DiLorenzo |
| 2008/0139870 A1 | 6/2008 | Gliner et al. |
| 2008/0140152 A1 | 6/2008 | Imran et al. |
| 2008/0154328 A1 | 6/2008 | Thompson et al. |
| 2008/0154331 A1 | 6/2008 | John et al. |
| 2008/0161881 A1 | 7/2008 | Firlik et al. |
| 2008/0161896 A1 | 7/2008 | Sauter-Starace et al. |
| 2008/0172103 A1 | 7/2008 | Kao et al. |
| 2008/0177196 A1 | 7/2008 | Burdick et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1 | 10/2008 | Tang et al. |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0275526 A1 | 11/2008 | Lozano |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1 | 7/2009 | Masmanidis et al. |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0253977 A1 | 10/2009 | Kipke et al. |
| 2009/0256702 A1 | 10/2009 | Robertson et al. |
| 2009/0292325 A1 | 11/2009 | Cederna et al. |
| 2009/0299174 A1 | 12/2009 | Wright et al. |
| 2009/0306728 A1 | 12/2009 | Wright et al. |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0069717 A1 | 3/2010 | Hafezi et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1 | 4/2010 | Obermiller et al. |
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1 | 5/2010 | Williams et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |

(56) References Cited

U.S. PATENT DOCUMENTS

| | | | |
|---|---|---|---|
| 2010/0292602 A1 | 11/2010 | Worrell et al. |
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1 | 2/2011 | Barker |
| 2011/0040203 A1 | 2/2011 | Savage et al. |
| 2011/0071766 A1 | 3/2011 | Dolan et al. |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |
| 2011/0282179 A1 | 11/2011 | Zdeblick |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277821 A1 | 11/2012 | Martens et al. |
| 2012/0296444 A1 | 11/2012 | Greenberg et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1 | 12/2012 | Firlik et al. |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1 | 4/2013 | Mercanzini et al. |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345780 A1 | 12/2013 | Tabada et al. |
| 2013/0345789 A1 | 12/2013 | Havel et al. |
| 2014/0039578 A1 | 2/2014 | Whitehurst et al. |

FOREIGN PATENT DOCUMENTS

| | | | |
|---|---|---|---|
| EP | 0 892 654 | 1/1999 |
| EP | 0 895 483 | 2/1999 |
| EP | 0 959 942 | 12/1999 |
| EP | 1 048 319 | 11/2000 |
| EP | 1 062 973 | 12/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 167 188 | 3/2010 |
| EP | 2 320 221 | 5/2011 |
| EP | 2 341 979 | 7/2011 |
| EP | 2 456 513 A1 | 5/2012 |
| EP | 2 542 303 A1 | 1/2013 |
| EP | 2 559 454 A1 | 2/2013 |
| EP | 2 604 313 | 6/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 674 193 A1 | 12/2013 |
| WO | WO-98/10010 | 3/1998 |
| WO | WO-03/022354 | 3/2003 |
| WO | WO-03/028521 | 4/2003 |
| WO | WO-03/066152 | 8/2003 |
| WO | WO-03/066153 A2 | 8/2003 |
| WO | WO-03/066157 | 8/2003 |
| WO | WO-2004/045707 | 6/2004 |
| WO | WO-2005/002467 | 1/2005 |
| WO | WO-2005/067792 | 7/2005 |
| WO | WO-2005/112216 | 11/2005 |
| WO | WO-2006/104432 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 | 4/2007 |
| WO | WO-2007/092330 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |
| WO | WO-2008/051463 | 5/2008 |
| WO | WO-2008/064269 A2 | 5/2008 |
| WO | WO-2008/068759 | 6/2008 |
| WO | WO-2008/075294 | 6/2008 |
| WO | WO-2008/077440 | 7/2008 |
| WO | WO-2008/089726 | 7/2008 |
| WO | WO-2008/107822 | 9/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |
| WO | WO-2010/014686 | 2/2010 |
| WO | WO-2010/055421 | 5/2010 |
| WO | WO-2011/115999 | 9/2011 |
| WO | WO-2013/014206 | 1/2013 |

OTHER PUBLICATIONS

US 8,469,885, 06/2013, Hafezi et al. (withdrawn)
U.S. Appl. No. 07/151,961, filed Feb. 3, 1988, Masahiko Okunuki et al.
Australian Patent Examination Report No. 1 dated Jan. 30, 2014 in corresponding Australian Application No. 2010326613, 2 pages.
Australian Patent Examination Report No. 1 dated Jan. 31, 2014 in corresponding Australian Application No. 2009315316, 3 pages.

(56) References Cited

OTHER PUBLICATIONS

Benabid, et al. "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, Montreal 1987 Appl. Neurophysiol. 50: 344-346.
Canadian Office Action for Application No. 2,743,575 dated Sep. 25, 2014, 3 pages. (ANSA-002CA.).
Cogan, Stuart F., et al. "Plasma-enhanced chemical vapor deposited silicon carbide as an implantable dielectric coating." Journal of Biomedical Materials Research Part A 67.3 (2003): 856-867.
Communication from the European Patent Office in Application No. 09795810.2 dated Sep. 14, 2011.
Decision of Rejection and Decision for Dismissal of Amendment in JP Patent Application No. 2011-543841 dated May 15, 2014.
Decision of Rejection for Japanese Appl. Ser. No. 2012-541491 dated Oct. 26, 2015.
EIC Biomedical, "Thin-film Encapsulation for Neural Recording and Stimulation Electrodes", Silicon carbide and oxycarbide, Apr. 2008: pp. 1-2.
English translation of Notice of Reasons for Rejection in JP application No. 2011-543841 dated Oct. 21, 2013.
European Communication and Search Report for Application No. 09795810.2 dated Sep. 25, 2013.
European Communication mailed May 22, 2013 including search report for EP application No. 12198290.4-1652.
European Search Report for Appl. Ser. No. 09803534.8 dated Jul. 21, 2011.
European Search Report for Appl. Ser. No. 13169272.5 dated Aug. 30, 2013.
European Search Report for application No. EP 14172592 dated Aug. 28, 2014 (ANSA-002PCT/EP/DIV2), 8 pages.
Examination Report for EP09795810.2 dated Jun. 22, 2012.
Examination Report from European Patent Office in 09 795 810.2 dated May 8, 2014.
Examination Report in AU Patent Application No. 2009276603 dated Mar. 3, 2014.
Examination report in AU Patent Application No. 2011234422 dated Feb. 11, 2014.
Examination Report in EP Patent Application No. 11 711 884.4 dated Mar. 28, 2014.
Fierce Medical Devices, "Medtronic Announces First U.S. Implant of World's Smallest, Minimally Invasive Cardiac Pacemaker", Feb. 20, 2014, pp. 1-3.
Gibney, "St. Jude places its Nanostim leadless pacemaker in a U.K. patient", Fierce Medical Devices, Jan. 27, 2014, pp. 1-3.
International Preliminary Report on Patentability for PCT/EP2010/068658 dated Jun. 5, 2012.
International Preliminary Report on Patentability for PCT/IB2009/007715 dated May 17, 2011.
International Preliminary Report on Patentability for PCT/US2009/052077 dated Feb. 1, 2011.
International Search Report and Written Opinion for PCT Appl. Ser. No. PCT/IB2015/053610 dated Jul. 20, 2015.
International Search Report and Written Opinion for PCT Appl. Ser. No. PCT/IB2015/056437 dated Nov. 5, 2015.
International Search Report and Written Opinion for PCT Appl. Ser. No. PCT/IB2015/056438 dated Nov. 5, 2015.
International Search Report and Written Opinion for PCT/EP2010/068658 dated Mar. 21, 2011.
International Search Report and Written Opinion in Application No. PCT/EP2011/055045 dated Jul. 18, 2011.
International Search Report and Written Opinion in PCT/US09/52077 dated Sep. 25, 2009.
International Search Report for PCT/IB2009/007715 dated Apr. 22, 2010.
Notice of Allowance for U.S. Appl. No. 14/287,917 dated Apr. 15, 2015.
Notice of Reasons for Rejection for Japanese Patent Application No. 2011-543841 dated May 30, 2013.
Notice of Reasons for Rejection in JP Patent Application No. 2011-521276 dated Mar. 3, 2014.
Notice of Reasons for Rejection in JP Patent Application No. 2011-521276 dated May 30, 2013.
Notice of Reasons for Rejections for Japanese Patent Appl. Ser. No. 2012-541491 dated Aug. 28, 2014, 8 pages.
Office Action for Canadian Appl. Ser. No. 2743575 dated Jan. 21, 2015 (4 pages).
Office Action for Canadian Appl. Ser. No. 2743575 dated Jun. 11, 2015.
Office Action for Canadian Appl. Ser. No. 2743575 dated Sep. 14, 2015.
Office Action for EPO Appl. Ser. No. 10787404.2 dated May 6, 2015.
Office Action for EPO Appl. Ser. No. 14172592.9 dated Aug. 20, 2015.
Office Action for European Application No. 10787404.2 dated Mar. 26, 2013.
Office Action for Japanese Appl. Ser. No. 2013-501857 dated Jun. 1, 2015.
Office Action for Japanese Appl. Ser. No. 2013-501857 dated Sep. 17, 2014.
Pollak, et al. "Effets de la Stimulation du Noyau Sous-Thalamique Dans La Maladie De Parkinson", Rev. Neurol (Paris),149, 3, 175-176. Mason, Paris, 1993.
Rousche, et al., "Flexible polyimide-based intracortical electrode arrays with bioactive capability," IEEE Transactions on Biomedical Engineering 48(3): 361-371 (Mar. 2001).
Second Notice of Reasons for Rejection for Japanese Application No. 2012-541491 mailed Apr. 8, 2015.
Sepulveda et al., "Finite Element Analysis of Current Pathways with Implanted Electrodes", J. Biomed. Eng. 1983, vol. 5, pp. 41-48.
US Notice of Allowance for U.S. Appl. No. 14/287,917 dated Jul. 20, 2015.
US Notice of Allowance for U.S. Appl. No. 14/316,154 dated Apr. 20, 2015.
US Notice of Allowance for U.S. Appl. No. 13/512,936 dated Feb. 20, 2014.
US Notice of Allowance for U.S. Appl. No. 13/512,936 dated Nov. 25, 2013.
US Notice of Allowance for U.S. Appl. No. 13/056,261 dated May 8, 2014.
US Notice of Allowance in U.S. Appl. No. 13/128,821 dated Dec. 24, 2013.
US Notice of Allowance in U.S. Appl. No. 13/128,821 dated Mar. 25, 2014.
US Office Action for U.S. Appl. No. 13/638,435 dated Jun. 30, 2015.
US Office Action for U.S. Appl. No. 14/309,491 dated Jul. 28, 2015.
US Office Action for U.S. Appl. No. 13/128,821 dated Dec. 14, 2012.
US Office Action for U.S. Appl. No. 13/128,821 dated Apr. 24, 2012.
US Office Action for U.S. Appl. No. 13/638,435 dated Mar. 12, 2015.
US Office Action for U.S. Appl. No. 14/316,154 dated Dec. 18, 2014.
US Office Action for U.S. Appl. No. 13/512,936 dated Aug. 14, 2013.
US Office Action for U.S. Appl. No. 13/056,261 dated Jan. 9, 2014.
US Office Action in U.S. Appl. No. 13/128,821 dated Nov. 14, 2013.
US Office Action in U.S. Appl. No. 13/056,261 dated Aug. 7, 2013.
US Office Action on U.S. Appl. No. 14/287,917 dated Sep. 26, 2014.
Written Opinion for PCT/EP2010/068658 dated Jun. 1, 2012.
Written Opinion for Singapore Application No. 201103393-3 dated May 2, 2012.
Written Opinion of the International Search Authority for PCT/IB2009/07715 dated May 12, 2011.
US Notice of Allowance for U.S. Appl. No. 14/309,491 dated May 11, 2016.
US Notice of Allowance for U.S. Appl. No. 14/470,356 dated Apr. 13, 2016.

(56) References Cited

OTHER PUBLICATIONS

Office Action for Canadian Appl. Ser. No. 2732309 dated Dec. 7, 2015.
US Notice of Allowance for U.S. Appl. No. 14/470,356 dated Mar. 18, 2016.
US Office Action for U.S. Appl. No. 13/638,435 dated Feb. 10, 2016.
US Office Action for U.S. Appl. No. 14/309,491 dated Mar. 3, 2016.
US Office Action for U.S. Appl. No. 14/470,423 dated Jan. 21, 2016.
Notice of Allowance on U.S. Appl. No. 14/470,423 dated Jun. 15, 2016.
Office Action on U.S. Appl. No. 15/194,033 dated Aug. 22, 2016.
US Corrected Notice of Allowability for U.S. Appl. No. 14/470,356 dated May 18, 2016.
US Notice of Allowance on U.S. Appl. No. 13/638,435 dated Sep. 16, 2016.

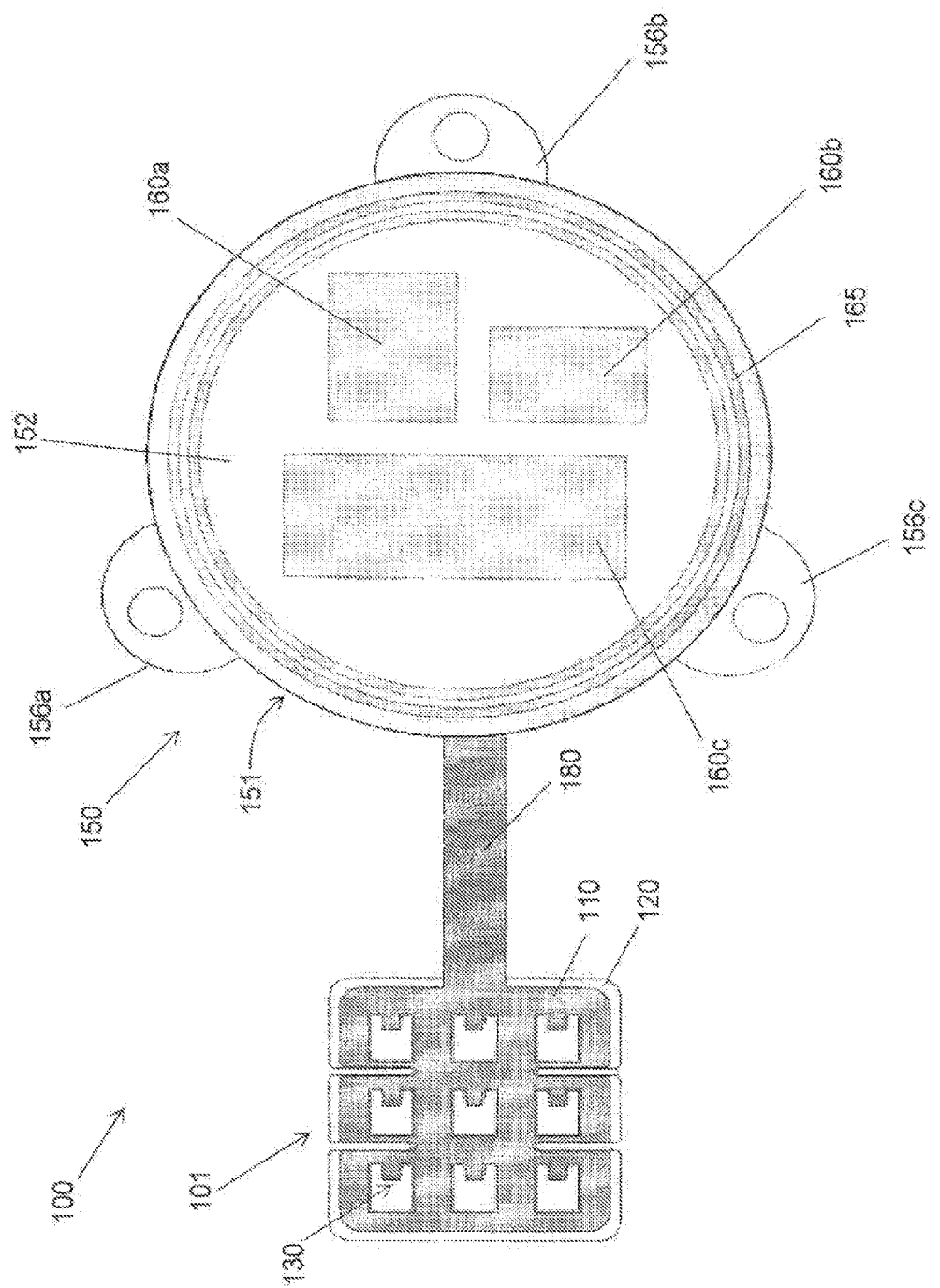

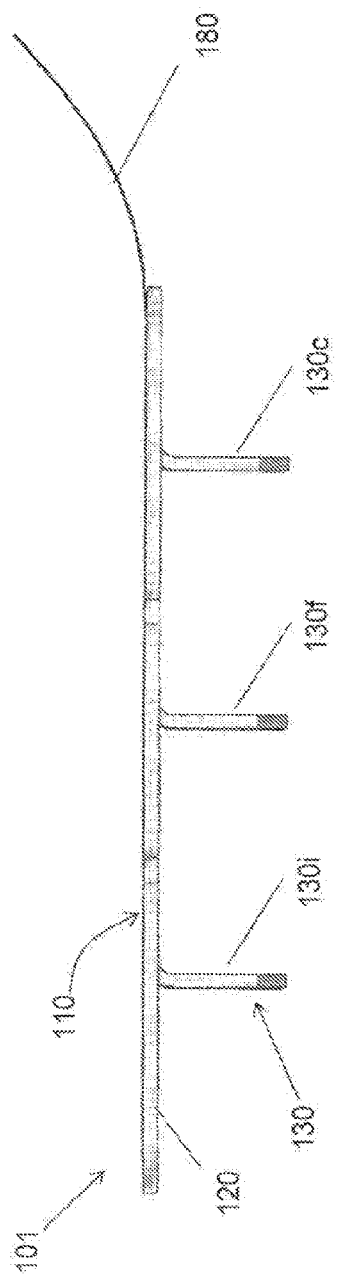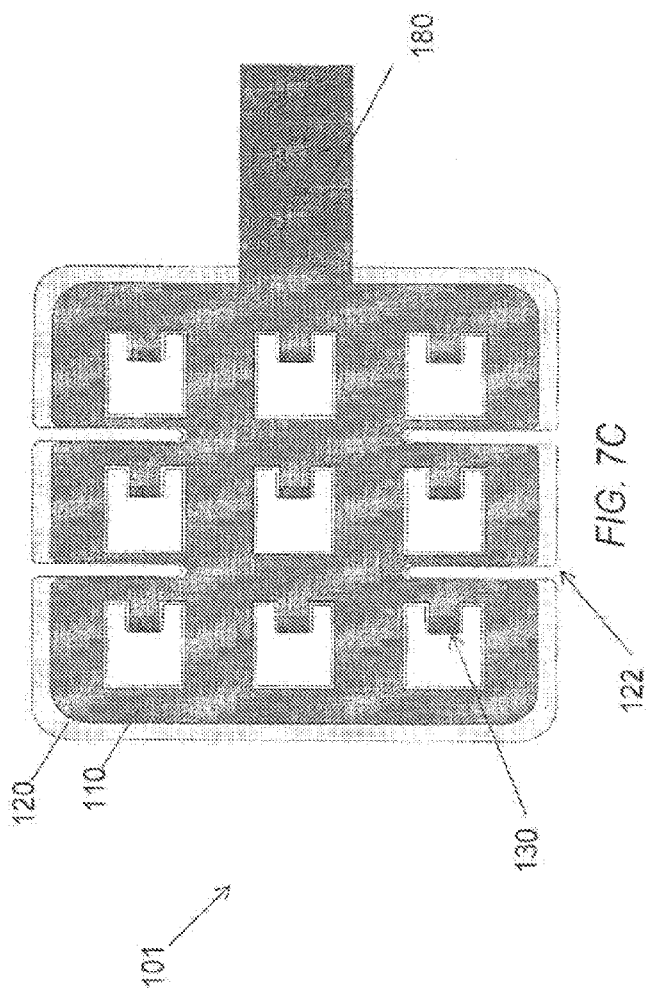

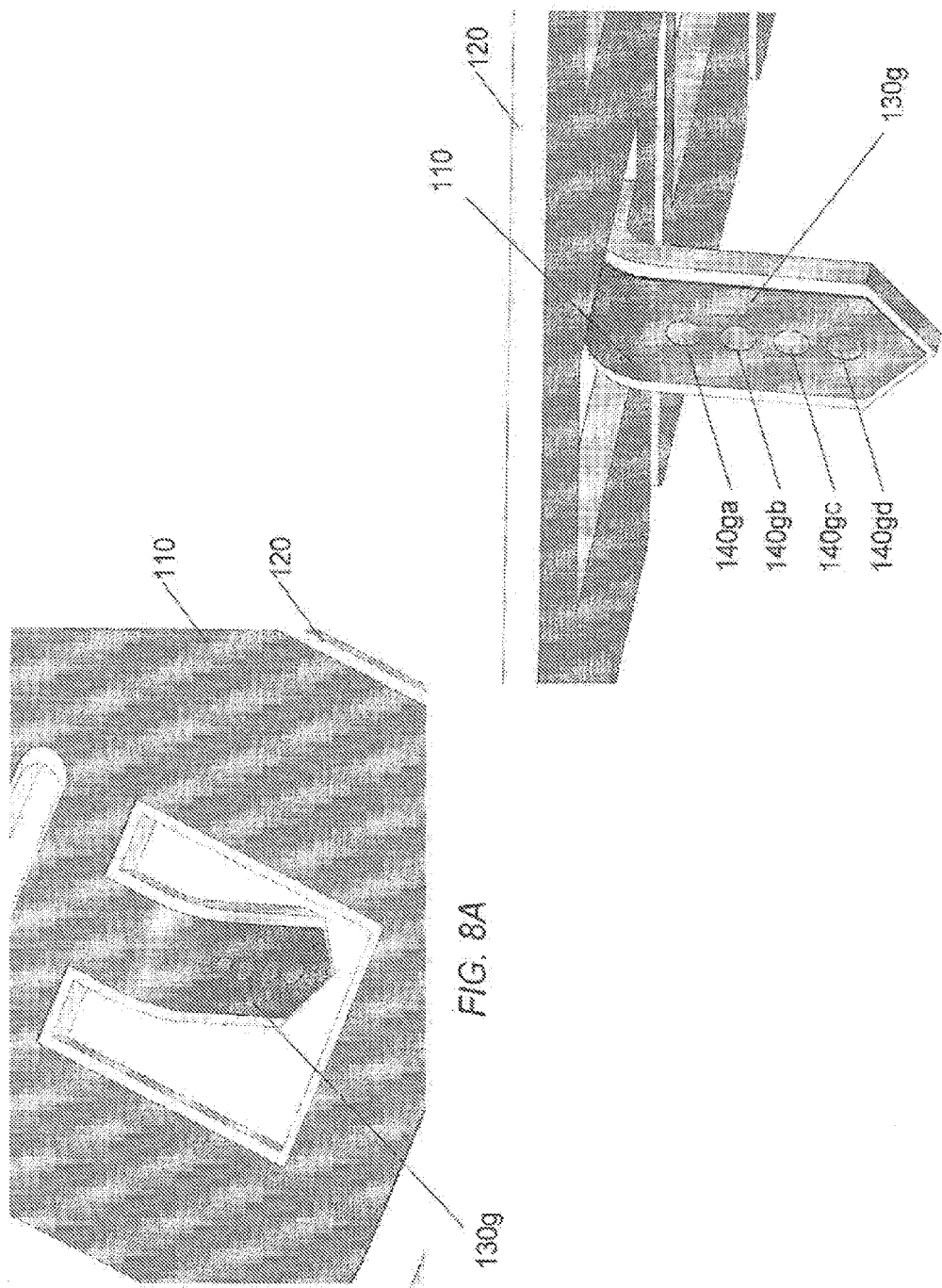

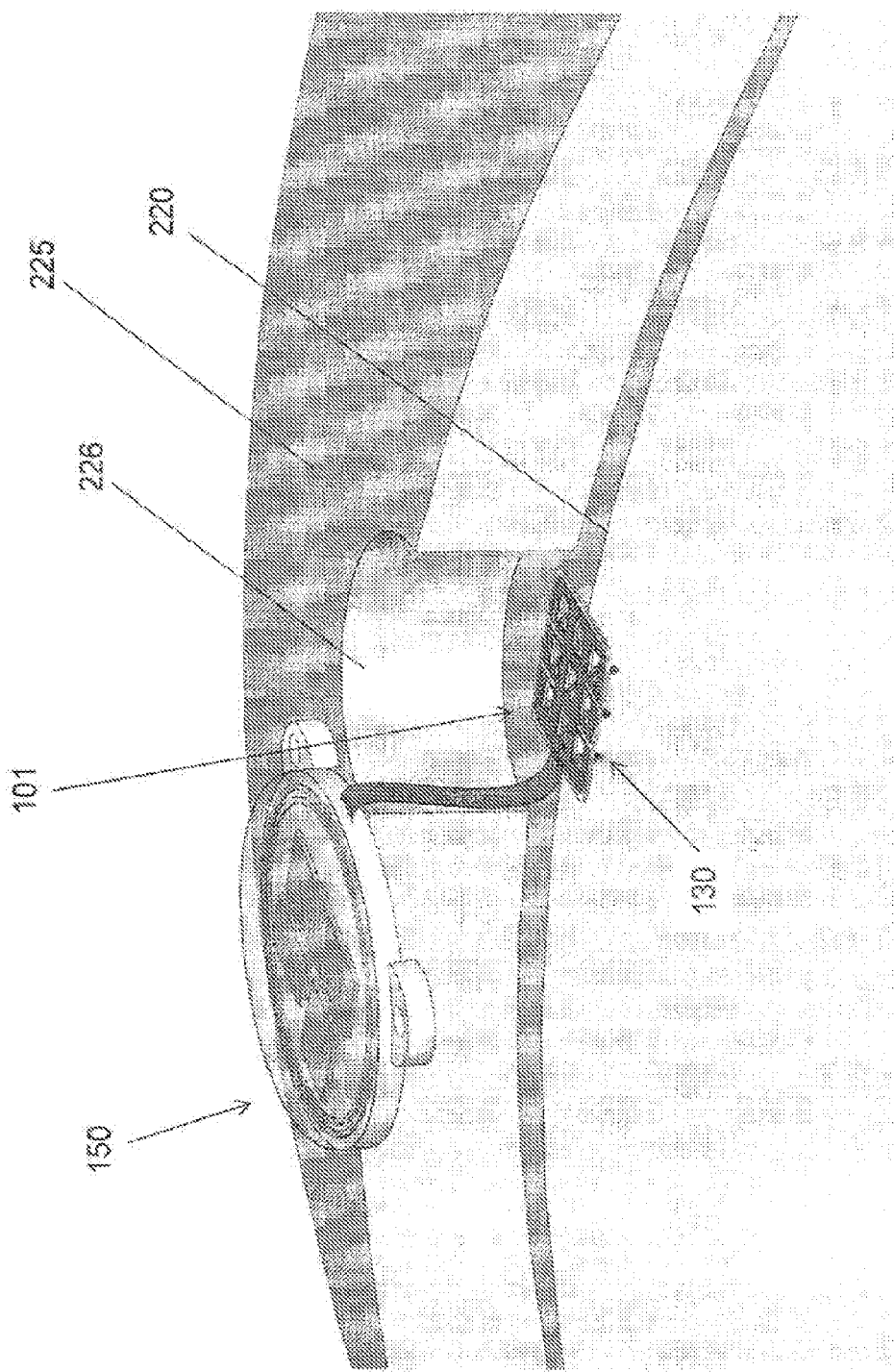

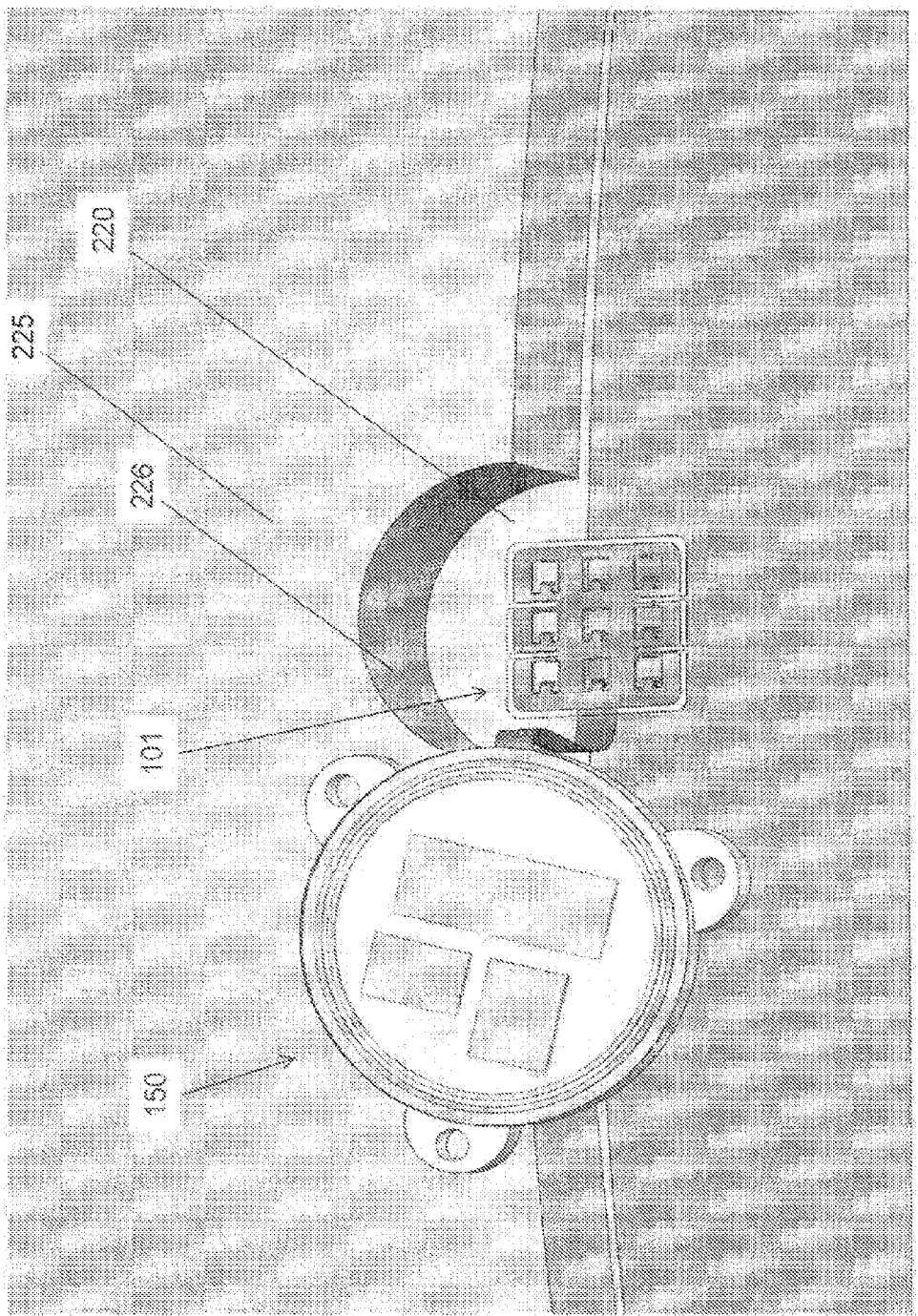

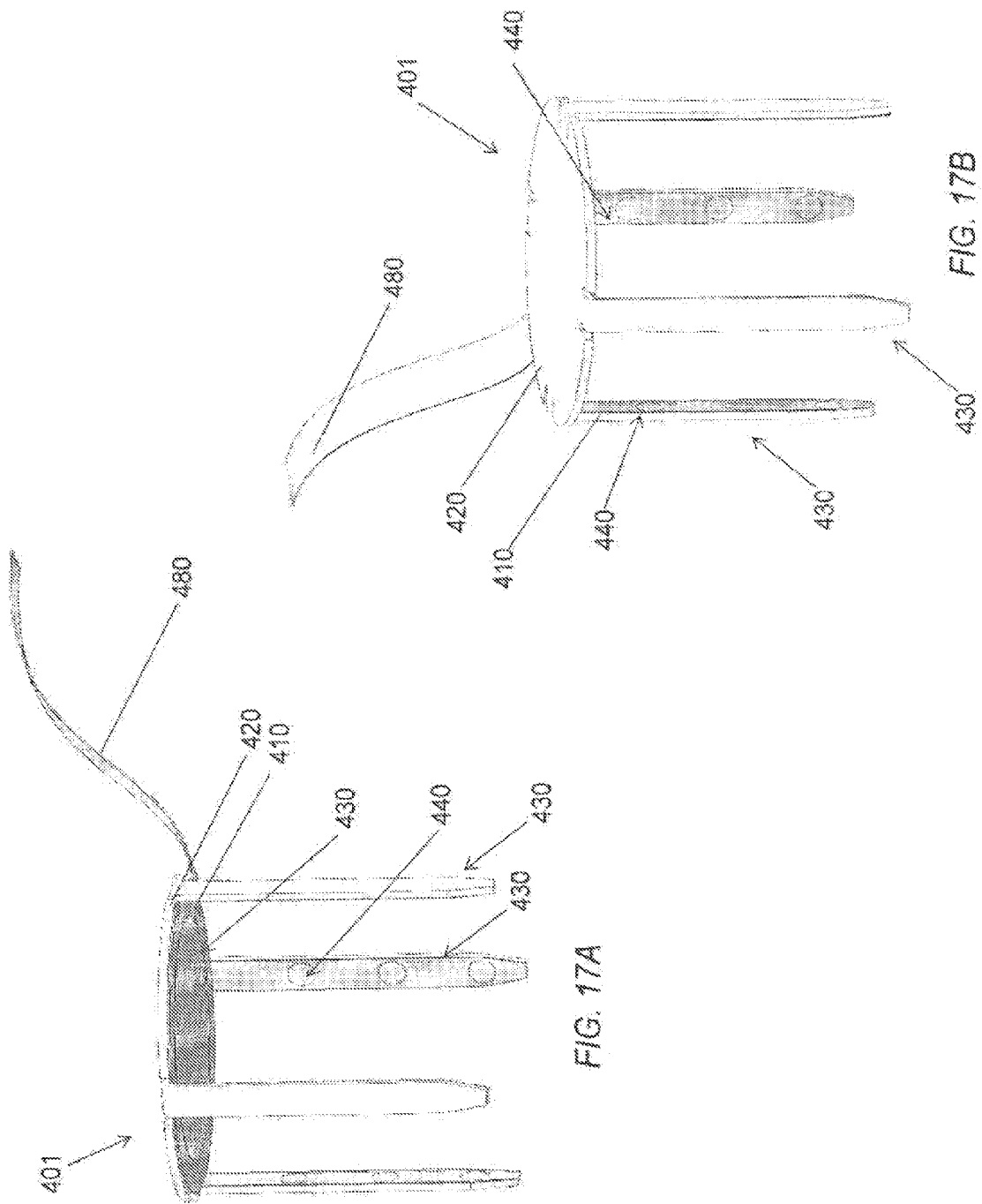

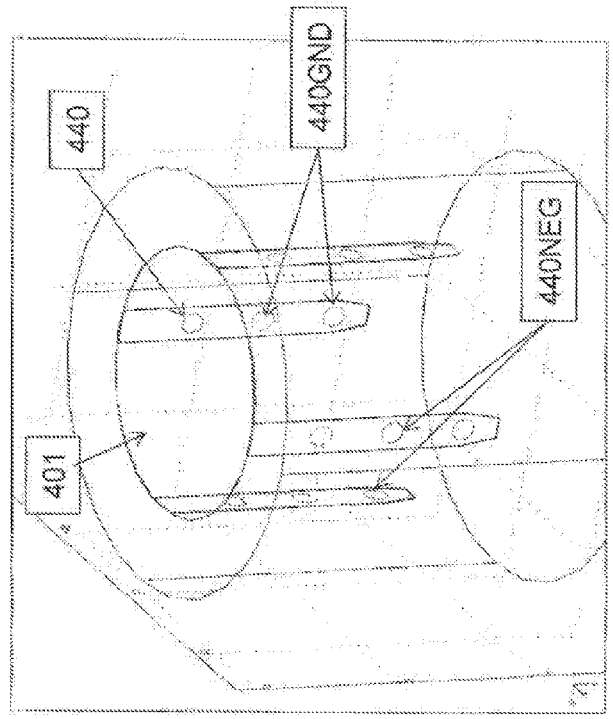
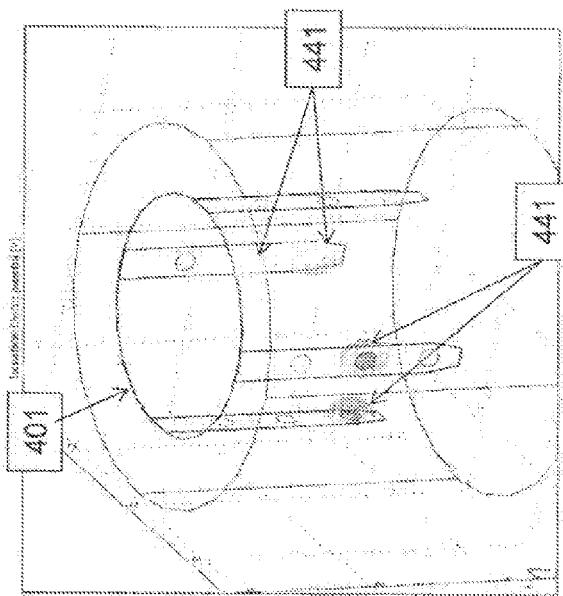
FIG. 17C
FIG. 17D

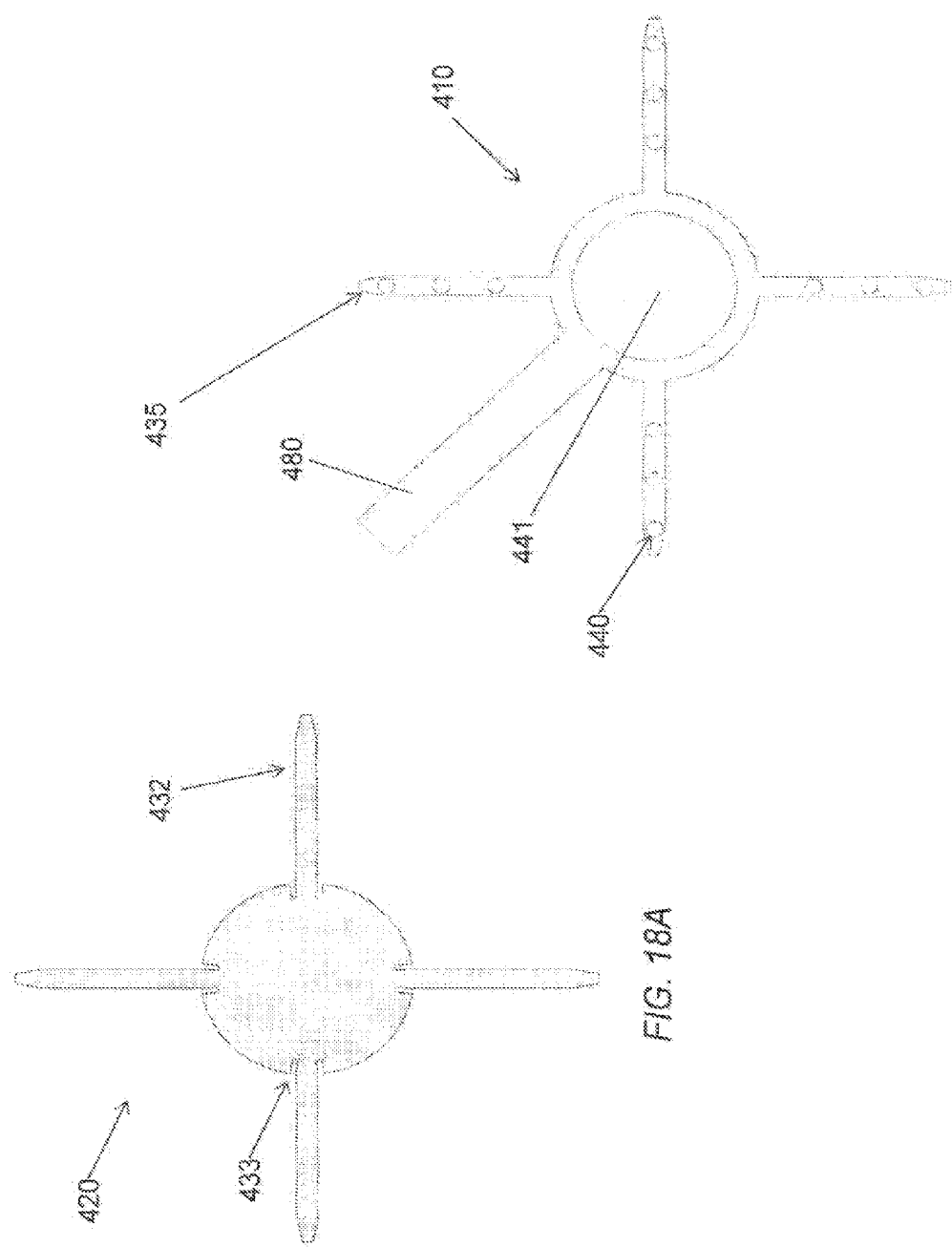

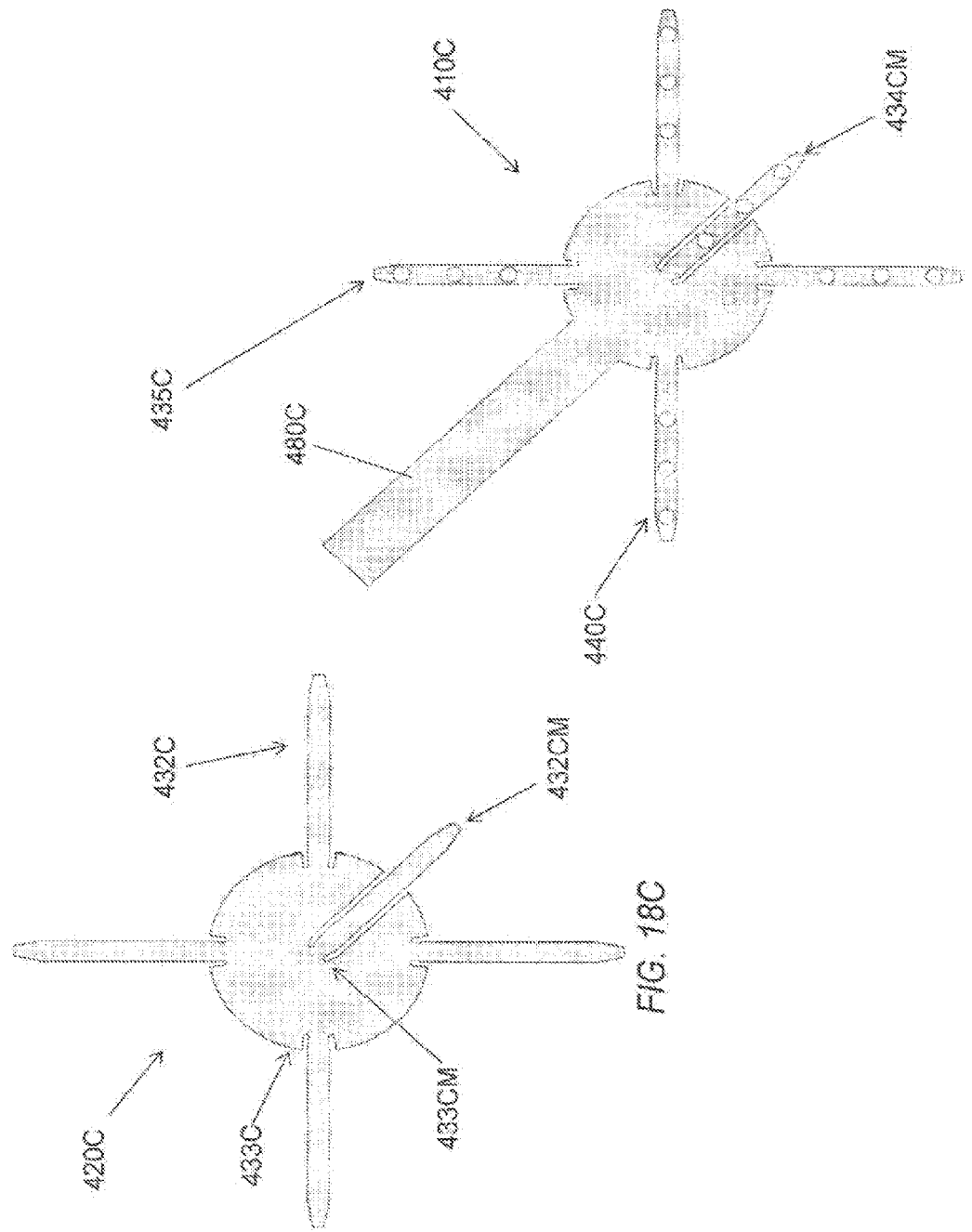

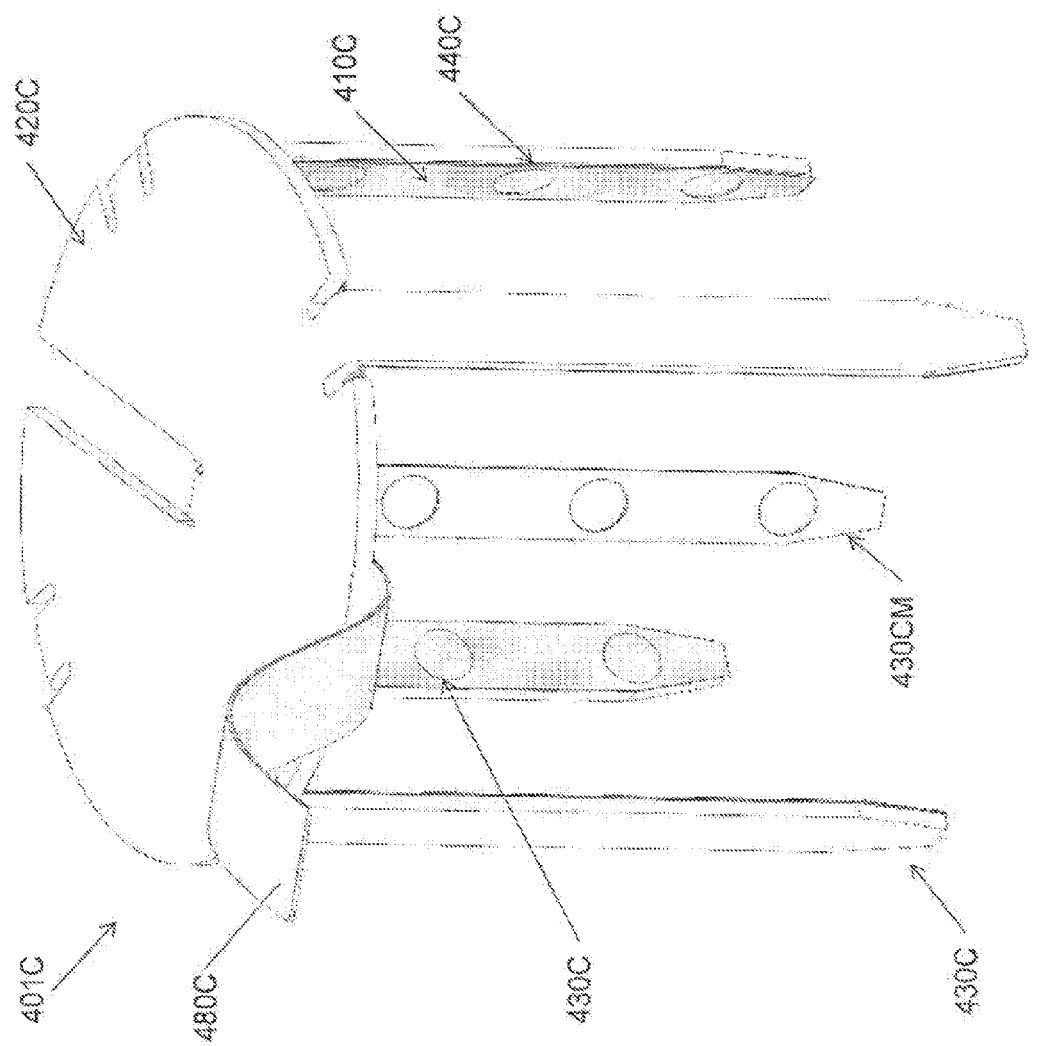

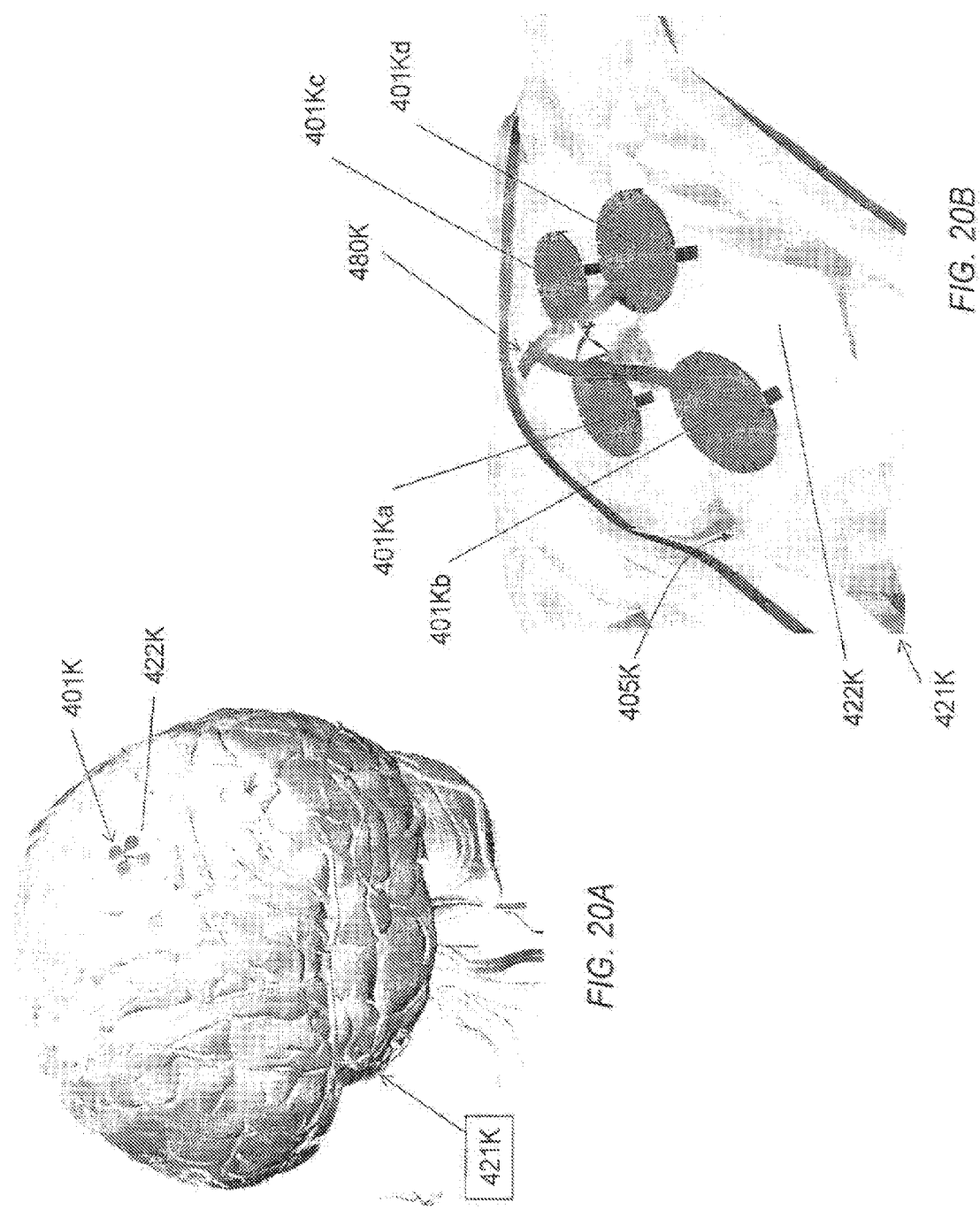

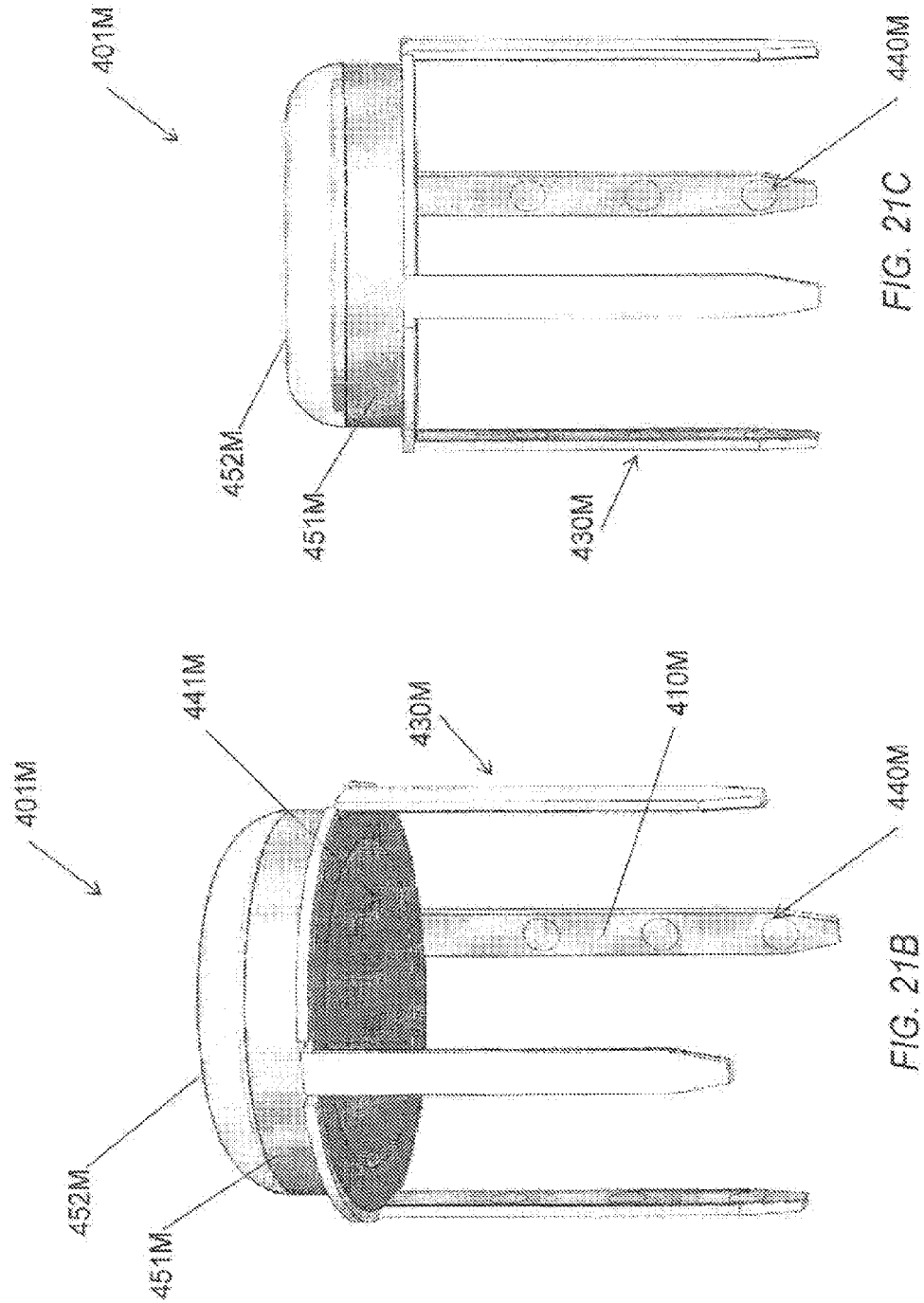

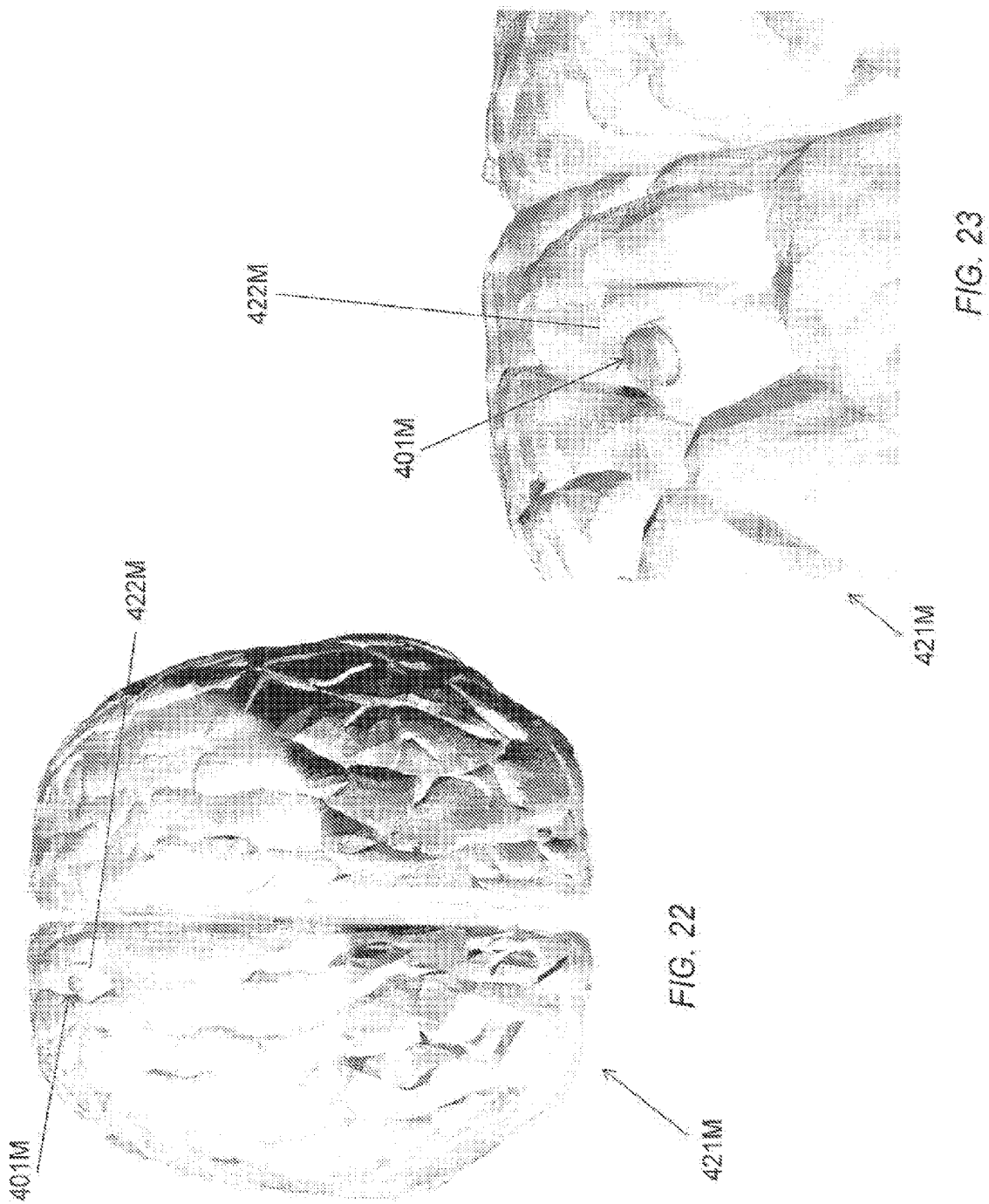

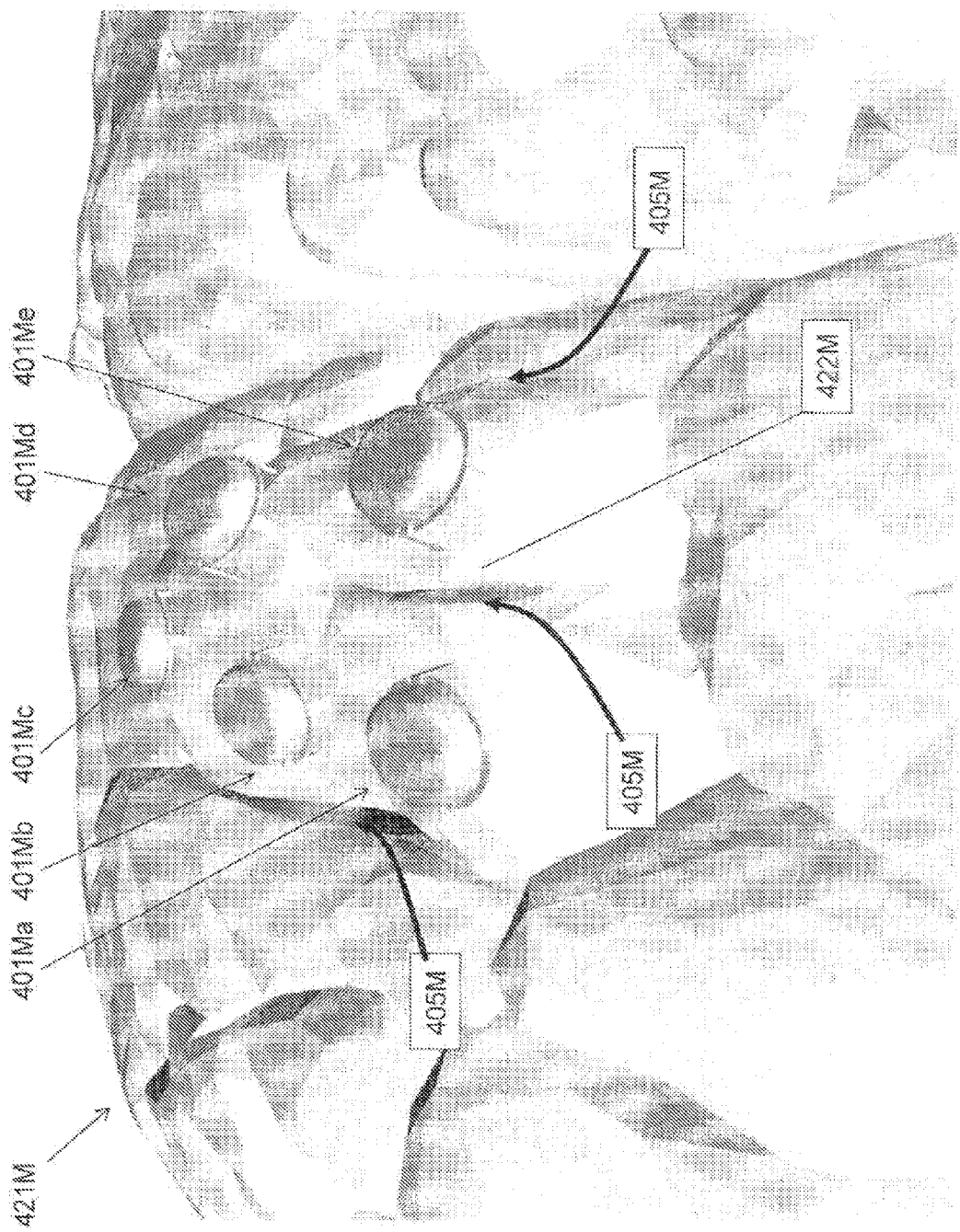

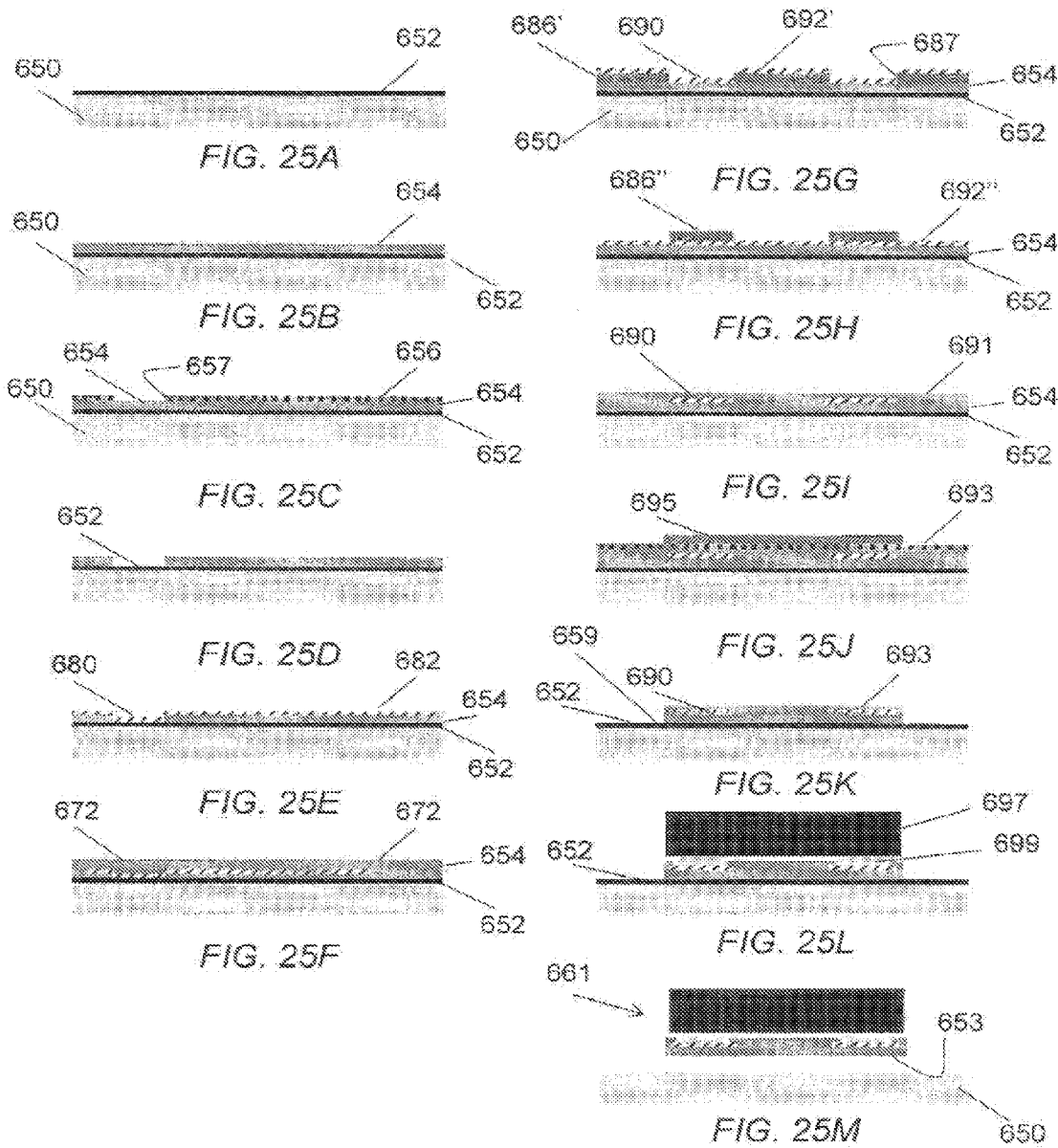

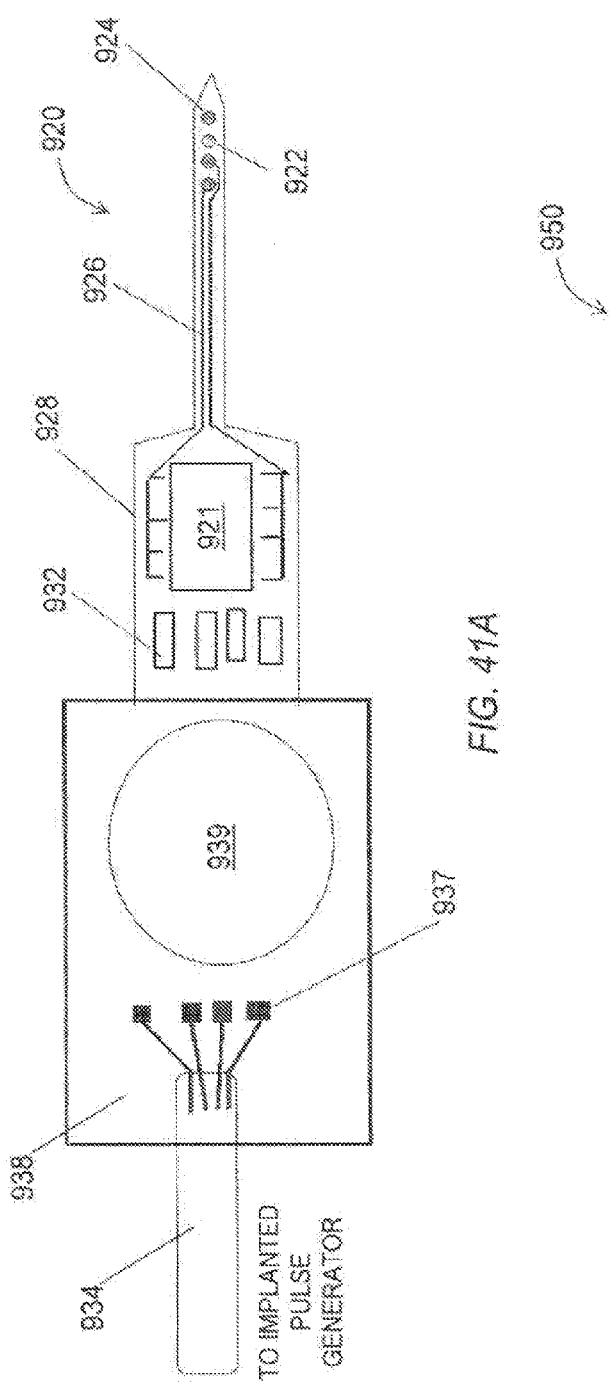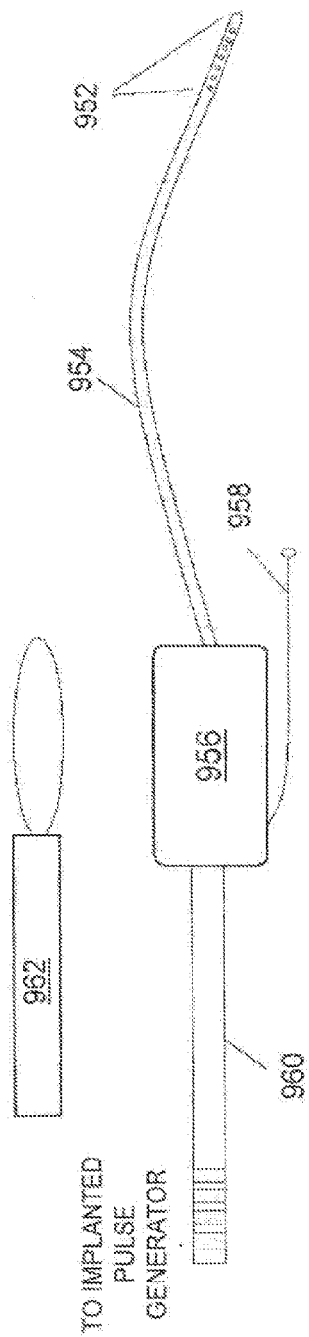
FIG. 41A
FIG. 41B

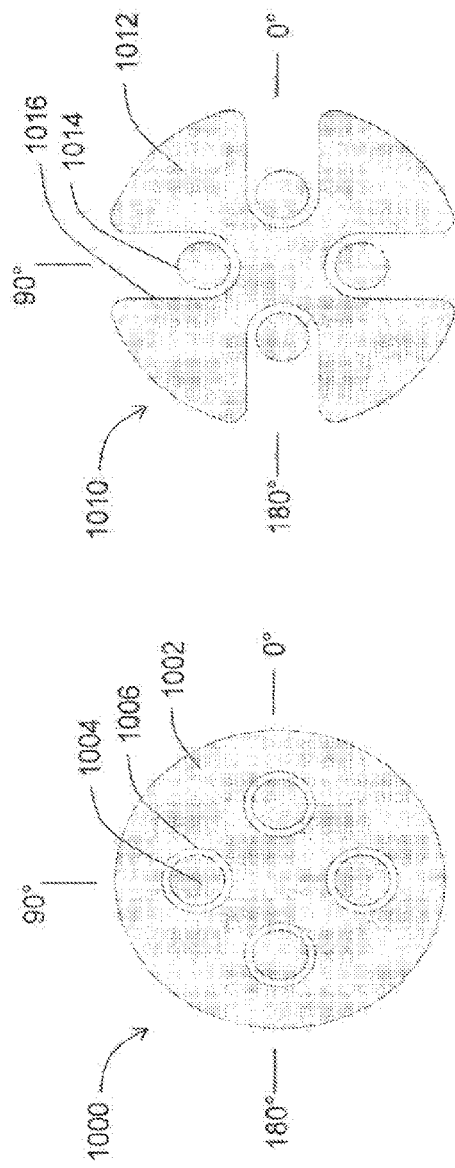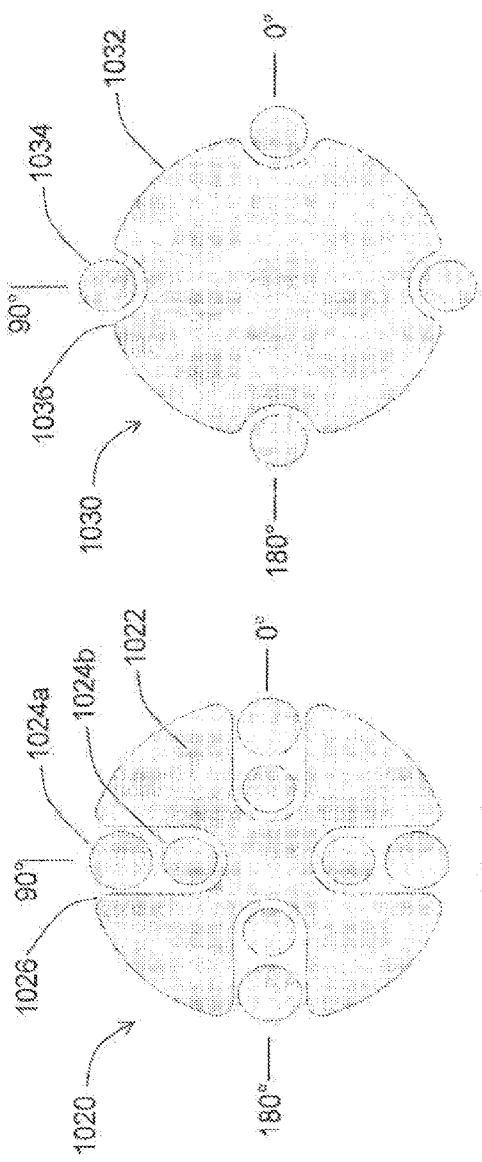
FIG. 42A  FIG. 42B  FIG. 42C  FIG. 42D

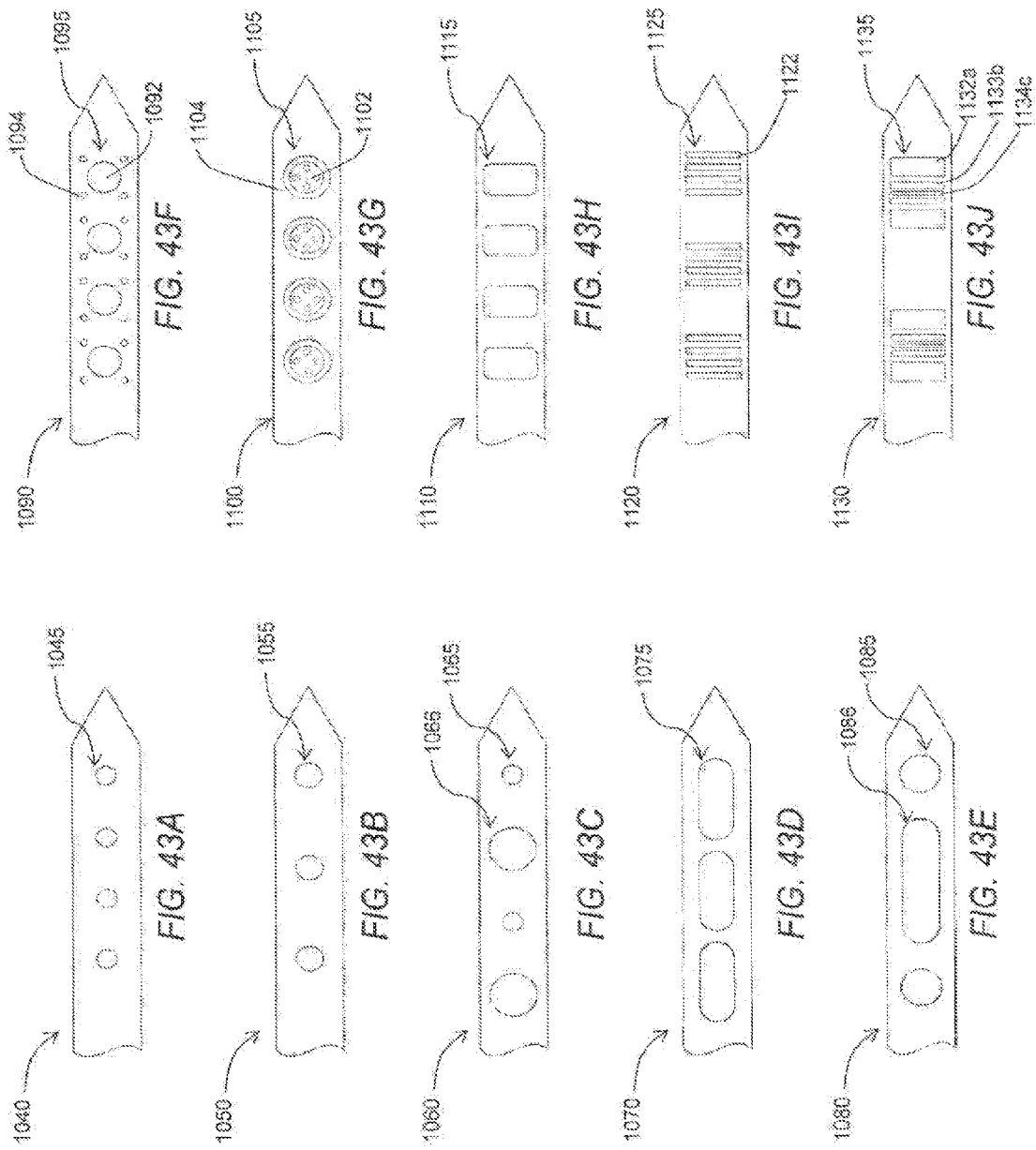

MICROFABRICATED SURFACE NEUROSTIMULATION DEVICE AND METHODS OF MAKING AND USING THE SAME

CROSS REFERENCE TO RELATED APPLICATION

The present application is a continuation of U.S. patent application Ser. No. 14/287,917, filed May 27, 2014, which is a continuation of U.S. patent application Ser. No. 13/512, 936, filed Jul. 19, 2012, which is a U.S. National Stage Application of PCT International Application Number PCT/EP2010/068658, filed on Dec. 1, 2010, which claims benefit of priority of U.S. Provisional Application Ser. No. 61/265,725 filed Dec. 1, 2009, the entire contents of each are incorporated by reference herein.

FIELD

The present disclosure relates generally to the field of interacting with biological tissue through the use of electrical probes, and more particularly to interacting with a neurological target through the use of microelectrode probes.

BACKGROUND

Neurostimulation is a category of medical devices that are used to transfer electric charge or electrical fields to tissue and result in a physiological change which benefits the patient, or performs a physiological measurement. Neurostimulation is used today in the cochlea, the retina, the peripheral nerve system, the spine, the brain and other parts of the body.

In particular application of Neuromodulation, conductive electrodes are placed in contact with certain cortical brain structures in order to treat certain neurological conditions. In the case of stimulating the cortical surface, for example, as described in U.S. Pat. App. 2008/0045775, the stimulation may relieve the symptoms of Parkinson's Disease, other movement disorders, or psychiatric disorders. In the case of stimulating an associated region of the cortical surface, for example, as described in U.S. Pat. No. 7,774,068, the stimulation can treat the symptoms of movement disorders including restless leg syndrome. In the case of stimulating the temporal love of the cortex, for example, as described in U.S. Pat. App. 2007/0055320 or [Theodore, W. H., Fisher, R. S., "Brain stimulation for epilepsy", *Lancet Neurology,* 3 (2), pp. 111-118, (2004).], the stimulation can treat the symptoms of temporal lobe epilepsy.

In the case where a cortical electrode array is used for recording and stimulating in long term therapy, an implantable pulse generator supplies the electrical signal to the electrode lead in contact with the brain structure. Additionally, the implantable pulse generator can record neural activity and electromagnetically transmit information outside the body. All components are placed surgically.

In the case where a cortical electrode array is used for recording and stimulation as a diagnostic tool, it may be placed temporarily on the cortex, for example for a few weeks, and then removed when no longer required. The information can be captured using wearable, or implantable, or semi-implantable, hardware.

In most prior art the electrode placed in contact with the cortex brain tissue has been metallic, disc like, and relatively large in size (e.g., 3 mm in diameter). In many cases, the electrodes are as large as the brain structures themselves. The large size of electrodes prevents specific and precise stimulation and recording of small brain targets which may be responsible for disease. The resulting large electric field and associated current paths stimulate other structures of the cortex, and do not concentrate on the intended target. Furthermore, these large electrodes cannot be used to identify the targets of the brain by neural-recording because the area they cover is very large.

Additionally, in most prior art, cortical electrodes are placed on the surface of dura mater which is an electrically insulting biomaterial. Placing electrodes on the dura mater, so called epidural electrode placement, prevents efficient charge transfer to and from the brain region, rendering stimulation and recording less efficacious. For example, electric fields and associated current paths established by an epidural electrode will not concentrate electrical stimulation on the intended target. This prevents the effective delivery of potentially therapeutic or diagnostic neural stimulation. Additionally, for example, neural signals that epidural electrodes are trying to capture will be very weak on the dural surface, and therefore signal-to-noise ratio will be very low. This prevents the reliable recording of diagnostically or therapeutically useful neural activity.

Current techniques that determine placement of such relatively large electrodes are accomplished by first performing a craniotomy that can vary in size but is usually at least 10 mm in diameter and be as large as several centimeters. An electrode array is then placed upon the surface of the cortex. Some surgeons may create a flap of the dura mater and place the electrode array directly on the cortical surface. Recordings of neural activity can be made using the electrode array, from several electrode contacts. This process is complex, requiring a highly skilled surgeon to place the electrode array, and usually a highly skilled neurophysiologist to interpret the neural recording data. The large craniotomies that have to be performed put the patient at risk of infection and serious collateral injury.

Attempts have been made at developing microfabricated devices specifically designed to incorporate an array of microelectrodes which can stimulate small volumes of tissue on the cortex of the brain. Attempts have also been made to develop sub-dural penetrating microelectrodes for use on the cortex of the brain, for example, as described in U.S. Pat. No. 5,215,088, "Three-Dimensional Electrode Device" by Normann et al. Additionally, descriptions have been made in [Richard et al., "A neural interface for a cortical vision prosthesis", *Vision Research,* 39, pp. 2577-2587, (1999)]. The prior devices however have not been able to easily translate to clinical use even though they have been available for more than a decade. This may be a result of the materials that are required to construct the device, because Silicon is a brittle material which may easily break during implantation or removal. Additionally, the reason for the lack of success may be because their functions do not provide enough additional information to the surgical team, because they only provide one electrode per penetrating shaft.

An important requirement for a successful outcome of cortical stimulation therapy, is the accurate placement of the stimulation and recording electrodes within the stimulation target area. Mislocation may result in unwanted side-effects, including sensory motor deficits. Additionally, a mislocated recording electrode will yield little or no relevant physiological data to the surgical team. Prior art procedures approximately localize the target by pre-surgical imaging and planning, for example through Trans-Cranial Magnetic Stimulation as described in [Komssi et al., "The effect of stimulus intensity on brain responses evoked by transcranial magnetic stimulation", *Human Brain Mapping*, 21 (3), pp. 154-164, (2004)] to identify a region of therapeutic interest. The targets themselves may be only a few mm or less, and not be detectable through standard imaging techniques alone. Therefore exploratory surgical procedures involving acute stimulation, many times with the patient awake during the procedure, are necessary. Once the precise target area is located, the acute or chronic recording and stimulation electrodes can be implanted at the precise location.

Disadvantages of the current technology include extension of operation time by several hours, which can be an increased burden for the patient, who may be awake during such procedures, and extended cost associated with lengthier complications from bleeding or tissue damage caused by large craniotomies or repeatedly placed electrode arrays are a major risk of infection for the patient. Additionally, the possibility that chronic electrode arrays are not precisely located at identified target for any number of reasons, including further brain movement require that patients return to surgery.

SUMMARY

For efficient stimulation of cortical brain structures, an array of subdural penetrating microelectrodes are required. After placement of the microelectrode array, the surgeon should be able to identify the area of the brain that requires stimulation by recording from the microelectrodes. Subsequently the surgeon should stimulate the identified structure.

For more efficient diagnostic and therapeutic use in cortical brain structures, subdural penetrating microelectrodes that create a three-dimensional volume of stimulation and recording functionality are described.

The disclosure described a system which places many microelectrode structures on the cortex of the brain, and allows the surgeon to apply a signal to each microelectrode separately, in parallel, or between at least two microelectrodes. Furthermore, using electronics to record neural activity from the system, the surgeon can develop a localized map of neural activity in the cortical region in which the electrode is implanted.

In one aspect, the disclosure relates to an implantable neurological probe. The neurological probe includes at least one protrusion on which at least one microelectrode elements are disposed on the surface of the protrusion. The microelectrode elements can perform neural stimulation or neural recording. The neurological probe preferably has several protrusions, and the protrusions preferably have several microelectrodes elements, or an array of microelectrode elements. Attached to the neurological probe, either on its surface, or connected through a tethered ensemble of wires, is the control circuitry. The control circuitry is itself encapsulated in a wearable or implantable enclosure. The neurological probe includes at least one electrical connection, or electromagnetic link, to the control circuitry. The control circuitry sends stimulation signals to the neurological probe. The control circuitry can also capture neurophysiological signals from the neurological probe. The control circuitry may connect telemetrically to yet another external controller, which can be used to transmit signals to and from the neurological probe, via the attached control circuitry.

In another aspect, the disclosure relates to a process for stimulating a neurological target. The process includes implanting a neurological probe at or near the target site on the cortex. The neurological probe itself comprises a supportive backing layer, at least one protrusion from the supportive backing layer, and at least one microelectrode element on each protrusion. Additionally, each of the at least one microelectrode elements are in electrical communication with either a proximal electrical contact, or in electrical communication with the control circuitry. The proximal electrical contact may be connected to a neurological stimulation source supplying an electrical signal. Alternatively, the control circuitry may be supplying the electrical signal to the microelectrode element. The supplied signal is applied to one or more of the microelectrode elements. The one or more energized microelectrode elements produce an electric field adapted to stimulate the neurological target site.

In yet another aspect, the disclosure relates to a process for recording from a neurological target. The process includes implanting a neurological probe at or near the target site on the cortex. The neurological probe itself comprises a supportive backing layer, at least one protrusion from the supportive backing layer, and at least one microelectrode element on each protrusion. Additionally, each of the at least one microelectrode elements are in electrical communication with either a proximal electrical contact, or in electrical communication with the control circuitry. The proximal electrical contact may be connected to a neurological recording source, such as an amplifier acquisition system. Alternatively, the control circuitry may be acquiring and recording the neurophysiological signal from the microelectrode element. The acquired signal may be transmitted from the control circuitry to the external controller. The one or more recorded microelectrode elements produce data on the electrophysiological activity of the neurological target site.

In another aspect, the disclosure relates to an implantable device comprising several neurological probes, where each neurological probes includes a supportive backing layer, at least one protrusion extending away from a surface of the supportive backing layer and at least one microelectrode element arranged along the at least one protrusion. The neurological probes may be connected to each other by tethered wires. Alternatively the neurological probes may be in telemetric communication.

In another aspect, the disclosure relates to an implantable neurological probe which includes a supportive backing layer, at least one protrusion extending away from a surface of the supportive backing layer and at least one microelectrode element arranged along the at least one protrusion.

In another aspect, the disclosure relates to a process for stimulating a neurological target by implanting a neurological probe within a vicinity of a cortical target site. The neurological probe includes a supportive backing layer, at least one protrusion extending away from a surface of the supportive backing layer. At least one microelectrode element is arranged along the at least one protrusion. The at least one microelectrode element produces an electric field adapted to stimulate the neurological target site.

In another aspect, the disclosure relates to an implantable neurological surface probe includes a supportive backing layer and a number of protrusions. Each protrusion is attached at one end to the supportive backing layer and extends away from a surface of the supportive backing layer. The probe also includes a microelectrode film disposed along at least a portion of the supportive backing layer. A number of microelectrode elements are disposed on the microelectrode film and arranged along each of the number of protrusions. Each microelectrode element is disposed at a respective depth measured from the surface of the supportive backing layer.

In yet another aspect, the disclosure relates to a process of making an implantable neurological surface probe includes shaping a supportive backing layer and defining within the supportive backing layer a number of rigid backing members. Each of the rigid backing members has a tip at one end and is attached to the supportive backing layer at another end. Each rigid backing member is bent at its attached end away from a surface of the supportive backing layer, forming a number of protrusions. A number of microelectrode elements are formed on a microelectrode film, and the microelectrode film is fastened along at least a portion of the surface the supportive backing layer. The film is fastened such that respective subsets of the plurality of microelectrode elements are arranged along each of the plurality of protrusions. When so arranged, each microelectrode element of each respective subset is disposed at a respective depth measured from the surface of the supportive backing layer.

BRIEF DESCRIPTION OF THE DRAWINGS

The foregoing and other objects, features and advantages of the disclosure will be apparent from the following more particular description of preferred embodiments of the disclosure, as illustrated in the accompanying drawings in which like reference characters refer to the same parts throughout the different views. The drawings are not necessarily to scale, emphasis instead being placed upon illustrating the principles of the disclosure.

FIG. 5A is a top view of the cortical neuromodulation device in FIG. 1.

FIG. 7B is a side view of the neurological surface probe in FIG. 1.

FIG. 7C is a top view of the neurological surface probe in FIG. 1.

FIG. 8A is a perspective view of a protrusion from the supportive backing layer of the neurological surface probe in FIG. 1.

FIG. 8B is an additional perspective view of a protrusion from the supportive backing layer of the neurological surface probe in FIG. 1.

FIG. 11A is a perspective view of a cross section of human anatomy demonstrating the placement of the cortical neuromodulation device of FIG. 1.

FIG. 11B is an additional perspective view of a cross section of human anatomy demonstrating the placement of the cortical neuromodulation device of FIG. 1.

FIG. 17A is a perspective view of an exemplary embodiment of a circular cortical neuromodulation device.

FIG. 17B is an additional perspective view of an exemplary embodiment of a circular cortical neuromodulation device shown in FIG. 17A.

FIG. 17C is a perspective view of a circular cortical neuromodulation device where currents have been applied to the microelectrodes.

FIG. 17D is an additional perspective view of a circular cortical neuromodulation device where currents have been applied to the microelectrodes demonstrating electric field isosurfaces.

FIG. 18A is a planar view of a component required to implement the circular cortical neuromodulation device shown in FIG. 17A.

FIG. 18B is a planar view of the microelectrode array film required to implement the circular cortical neuromodulation device shown in FIG. 17A.

FIG. 18C is a planar view of a component required to implement an alternative embodiment of the circular cortical neuromodulation device shown in FIG. 17A.

FIG. 18D is a planar view of the microelectrode array film required to implement an alternative embodiment of the circular cortical neuromodulation device shown in FIG. 17A.

FIG. 18E is a perspective view of the alternative embodiment of the circular cortical neuromodulation device components shown in FIG. 18C and FIG. 18D.

FIG. 20A is a planar view of human brain anatomy demonstrating the placement of a multiplicity of circular cortical neuromodulation devices of FIG. 17A.

FIG. 20B is a detailed perspective view of human brain anatomy demonstrating the placement of a multiplicity of circular cortical neuromodulation devices of FIG. 17A.

FIG. 21B is an additional perspective view of the circular cortical neuromodulation device shown in FIG. 21A.

FIG. 21C is a planar view of the circular cortical neuromodulation device shown in FIG. 21A.

FIG. 22 is a perspective view of human brain anatomy demonstrating the placement of a circular cortical neuromodulation device of FIG. 21A.

FIG. 23 is a detailed perspective view of human brain anatomy demonstrating the placement of a cortical neuromodulation device of FIG. 21A.

FIG. 24 is a detailed perspective view of human brain anatomy demonstrating a multiplicity of implanted circular cortical neuromodulation devices of FIG. 21A.

FIGS. 24A through 25M illustrate cross sections of an exemplary microelectrode device at various different stages of construction according to an exemplary fabrication procedure.

FIG. 41A is a schematic view of an embodiment of a neurological target stimulator.

FIG. 41B is a schematic view of an embodiment of a neurological target stimulator system.

FIG. 42A through 42D are a schematic views of various alternative embodiments of a microelectrode array.

FIG. 43A through FIG. 43J are schematic views of various alternative embodiments of a cortical depth microelectrode array.

DETAILED DESCRIPTION OF THE PREFERRED EMBODIMENTS

Figure 1:
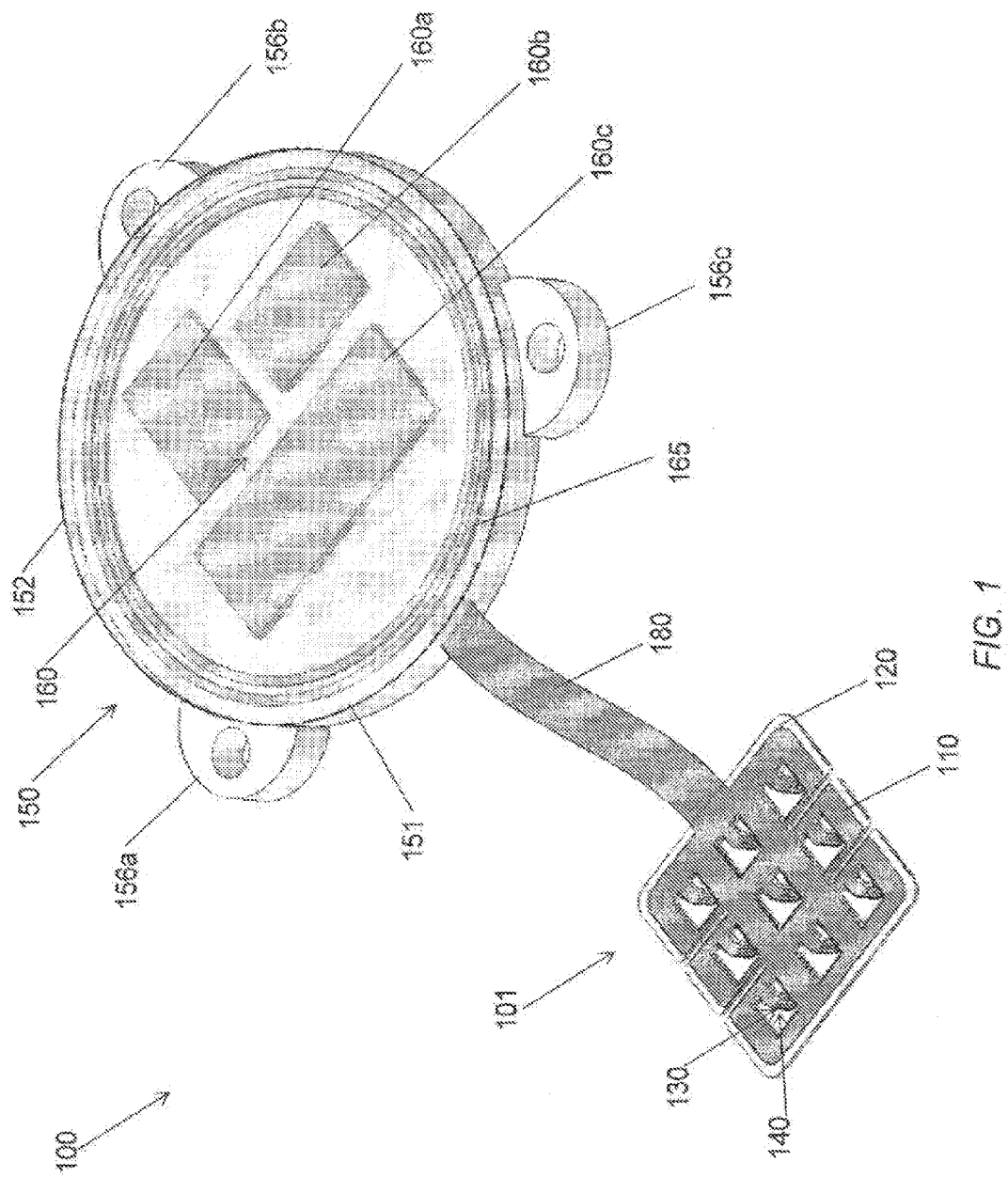
FIG. 1 is a perspective view of one embodiment of a cortical neuromodulation device.

Described herein are microelectrode array devices, and methods of fabrication and use of the same, to provide highly localized and efficient electrical stimulation of a neurological target, such as individual neurons, groups of neurons, and neural tissue as may be located in an animal nervous system, such as the human cortex. In indications where it is difficult to determine the final positioning of the microelectrode for diagnostic or therapeutic use, it is beneficial to safely implant many electrodes in the target region, and then proceed to determine the best electrode by applying an electrical signal for neural stimulation or performing neural recording. A higher number of microelectrodes, and more specifically a higher number of microelectrode in a three-dimensional volume, will increase the probability that the best therapeutic or diagnostic region is in contact with a microelectrode.

The stimulation can be highly localized, because the microelectrode elements can be as small as only 2 μm or large as 2 mm in either of diameter or width. The relative spacing between such microelectrode elements can also be as small as only 2 μm or as large as 2 mm. Although 2 μm are indicated as lower limits to either dimension or spacing, other embodiments are possibly having dimensions and/or inter-element spacing of less than 2 μm, as may be practically limited by fabrication techniques. Generally, microelectrodes in the form of a disc of about 100 μm in diameter, with about 500 μm spacing are particularly efficient in recording from neural tissue in the cortex. Additionally, microelectrodes in the form of a disc of about 300 μm in diameter, with about a 500 μm spacing are particularly efficient in stimulating neural tissue in the cortex. An array of such microelectrode elements may consist of one or more such elements (e.g., four elements), each disposed at a respective position along a support structure. There is additionally an array of support structures that can be all be arranged to protrude from a supportive backing. In this manner, a multiplicity of microelectrode elements can be arranged in three-dimensional space. This is in contrast to currently available epidural recording and stimulation leads, such as the RNS® System from NeuroPace Corp. (Mountain View, Calif.) which may be marketed in the future. Additionally, grid and strip electrodes are marketed for transient use from Integra Corp. (New Jersey, N.J.). Such commercially available devices include relatively large, disc electrodes measuring about 3 mm in diameter, with large spacing between each electrode (i.e., 5 mm) and only generate a two dimensional area of targeting in the epidural region of the cortex. It would be beneficial to have a system that can provide a three-dimensional volume of influence in the subdural area of the cortex, in order to perform better neural recording and provide more efficacious neural stimulation.

Smaller microelectrode elements can be used to provide neurological stimulation that is highly localized and efficient because an array of such microelectrodes can also be used to identify the stimulation region of interest. For example, one or more microelectrode elements of such an array of microelectrode elements can be used to detect and, in some instances, record neuronal activity in the vicinity of the detecting/recording microelectrode elements. Such refinement offered by the relatively small size and/or spacing of the microelectrode elements can be used to obtain a highly localized map of neuronal activity in the three-dimensional volume surrounding the implant. A suitably dimensioned microelectrode array, and a suitably dimensioned supportive backing layer, can have multiple microelectrode elements positioned in a general vicinity of a neurological target. The array can therefore be used to locate a precise neurological target without further repositioning, by identifying those one or more microelectrode elements located in a very specific region of the neurological target. The microelectrode array can be programmed to stimulate in a very specific region, for example, using only a certain number of the microelectrode elements to actively stimulate the surrounding neurons and/or neuronal tissue, while other electrode elements of the array remain inactive.

In some embodiments, a three-dimensionally arranged neurological surface probe includes such a multiplicity of microelectrode arrays having elements with relatively small size and/or spacing that can be used to obtain a highly localized map of neuronal activity in the region surrounding the implant. For example, such a device configured with a several linear arrays of microelectrodes can be surgically placed onto the surface of the patient's brain (i.e., the cortex). Preferably, the elements of the microelectrode arrays span a region including the neurological target. Neurological activity can then be independently detected by one or more of the microelectrode elements. The detected activity may be captured in a recorder or display device, allowing a clinician to identify which one or more of the microelectrode elements is positioned closest to the intended target. Beneficially, location of the target can be determined without any repositioning of the elongated device, thereby simplifying the medical procedure and reducing patient risk.

In some embodiments, the device is used only transiently, or acutely, being removed after the target has been located, being replaced with a chronic probe, positioned at the determined target location. Alternatively or in addition, the device itself can be left in place as a chronic device, the same microelectrodes, or different ones, being used to record and/or stimulate the neurological target over an extended period.

One embodiment of a neurological surface probe illustrated in FIG. 1 includes a neurological device assembly referred to as a cortical neuromodulation device 100. The cortical neuromodulation device 100 includes a neurological surface probe 101 and a control module 150. The neurological surface probe 101 is located on the distal portion of the cortical neuromodulation device 100, and the control module 150 is located on the proximal portion of the cortical neuromodulation device 100. The neurological surface probe 101 is comprised of two components, the supportive backing layer 120 and the microelectrode array film 110. In this embodiment nine protrusions from the neurological surface probe are referred to as cortical depth probes 130. On the surface of each cortical depth probe is a linear array of microelectrode elements 140. The neurological surface probe 101 is attached to the control circuitry 150 via a ribbon cable tether 180. The control module 150 is comprised of a lower housing 151 and an upper housing 152. The lower housing 151 may also incorporate at least one fixation structure 156 which is used to fix the control module 150 the skull. In the current embodiment three fixation structures 156a, 156b, 156c are provided which incorporate through holes for cranial fixation screws. Inside the control module 150 is the control circuitry 160 which is comprised of an electronic circuit. In the current embodiment the control circuitry 160 is comprised of three individual and interconnected control circuits 160a, 160b, 160c. Additionally, inside the control module 150 a loop antenna 165 is connected to the control circuitry 160 and is used to communicated information to and from the control module 150 extra-corporeally. In the exemplary embodiment, each of the microelectrode elements 140 is in electrical communication with the control circuitry 160 via a respective electrical conductor disposed in the microelectrode array film 110 and the ribbon cable tether 180. In use, stimulation signals are directed from the control circuitry 160 to the microelectrode elements 140. Additionally, in use, recorded neurophysiological signals are directed from the microelectrode elements 140 to the control circuitry 160. Furthermore, in use, the control circuitry 160 is programmed to function by an external control system (not shown) through the loop antenna 165. The control circuitry 160 can also transmit information about the recorded neurophysiological signals to the external control system (not shown) through the loop antenna 165.

The size and shape of the control module 150 can vary, but is generally intended to be implanted on the surface of the skull. The size and shape of the neurological surface probe 101 can vary, but is generally intended to be implanted on the surface of the cortex. The size and shape of the cortical depth probes 130 can vary, but are generally intended to penetrate the layers of the cortex. Finally, the size, shape, and quantity of the microelectrode elements 140 can vary, but are generally intended to record from the cortical layers and stimulate the cortical layers. The neurological surface probe 101 is shown as a square. Alternatively, in some embodiments the neurological surface probe 101 is circular. Alternatively, in some embodiments the neurological surface probe 101 is rectangular. The neurological surface probe 101 is shown with all cortical depth probes 130 descended and protruding from its surface. Alternatively, in some embodiments not all of the cortical depth probes 130 are descended. Alternatively, in some embodiments the cortical depth probes 130 are descended only at the time of surgery, once the surgeon has decided which cortical depth probes 130 are necessary.

The cortical neuromodulation device 100 is preferably sized and shaped for its intended neurological application. The cortical neuromodulation device 100 is not limited for use in the animal or human cortex. For example, the cortical neuromodulation device 100 may be at least partially placed within the central nervous system. Alternatively or in addition, the cortical neuromodulation device 100 may be used within other parts of the body, such as the retina, the cochlea, the epidural space of the spine, the spine, and other locations within the peripheral nervous system. Thus the diameter and length of the cortical neuromodulation device 100 may vary depending on the particular anatomical target. Additionally, the configuration of the neurological surface probe 101 and the cortical depth probes 130 are sized and shaped for an intended neurological target. The number, shape, orientation, size, and spacing of the microelectrode elements 140 can be defined in response to the intended neurological target.

In at least some embodiments one or more of the microelectrode elements 140 are sized and or spaced to record form and/or stimulate a single neuron, or group of neurons. The cortical neuromodulation device 100 can be used to detect and/or record neuronal activity at the neurological target. Neuronal activity naturally occurring within the neurological target gives rise to local electromagnetic fields that can be detected by one or more of the microelectrode elements 140 of the cortical depth probe 130. For example, electric fields produced by neurons will polarize one or more of the microelectrode elements 140. Such polarization gives rise to an electrical potential with respect to a reference, such as electrical ground, or another one of the microelectrode elements 140. Such electric activity can be further conducted to the control circuitry 160 through the internal electrical conductors in the ribbon cable tether 180. The control circuitry 160 can then electromagnetically transmit captured data of the detected electrical activity for further processing by an external controller (not shown). For example, the captured data can be displayed on a computer.

Alternatively or in addition, one or more of the microelectrode elements 140 can be used to electrically stimulate the neurological target. For example, one or more electrical signals generated by the control circuit 160 can be applied to one or more of the microelectrode elements 140. These electrical signals can be conducted through the internal electrical conductors in the ribbon cable tether 180 to one or more of the microelectrode elements 140 of the microelectrode array film 110. Depending on the amplitude and polarity of the electrical signals, an electrical field will be induced by the polarized microelectrode elements 140. Electrical fields induced by such polarization can interact with one or more neurons at the neurological target.

In some embodiments, at least a portion of the control module 150 can be extracorporeal. Alternatively or in addition, the stimulation source can be implanted in the body. Any implanted elements of the stimulation source are preferably fabricated and/or contained with a hermetically sealed, bio-compatible envelope. Such bio-compatible packaging of signal sources is well know, for example, in the area of artificial pacemakers. The stimulation source, when provided, may be a controllable signal generator producing a desired signal according to a prescribed input. For example, the signal generator may receive an input indicative of a desired output stimulation signal frequency. Such output stimulation signals can have a variety of wave forms, such as pulses, charged balanced pulses, sinusoidal, square wave, triangle wave, and combinations of such basic wave forms.

In some embodiments, the stimulation source includes a pulse generator for applying signals to the microelectrode elements 140. The signals from the pulse generator can be connected directly to the microelectrodes, or they can be preprocessed using electronics. In some embodiments, such preprocessing electronics are embedded within the implantable device. The preprocessing electronics can filter certain parts of an original signal, such as a cardiac pacemaker signal, in order to select preferred frequency components of the original signal that are at or near a peak resistance frequency of the microelectrodes. For embodiments in which there are more microelectrodes than signals, electronics can route the stimulation signals to preferred one or more of the microelectrodes.

Microfabricated Components

A microfabrication procedure can be used to implement electrically conductive traces within an insulative substrate to form any of the microelectrode array devices described herein, whether the array devices are rigid or flexible. The microfabricated components include portions of the microelectrode array assembly. The microelectrode array can be implemented in a polymeric material such as polyimide or parylene and includes thin film or plated layers of a metal or metal oxide with high charge transfer capability such as platinum, platinum-iridium, iridium, iridium oxide or titanium. In some embodiments, other metals, metal alloys, carbon based conductive materials, and electrically conductive materials, such as doped semiconductors, conductive polymers, and conductive ceramics may be used. In some embodiments, the polymeric and metallic layers are deposited sequentially and formed using established principles of microfabrication such as spin coating, DC/RF sputtering, photolithography, plasma etching, and etching with a mask consisting of a secondary or sacrificial material such as silicon dioxide or photosensitive resist.

The metallic layer is formed to create one or more of the microelectrode array elements and electrically conductive traces that connect the array elements to one or more of the electronics. In some embodiments, the microelectrode array includes multiple layers. For example, the polymeric layers serve to isolate the traces from each other, while also providing the structure of the implant's stimulating/recording tip. There are several fabrication methods which can be described to build such a microfabricated component.

The insulative substrate can be a polymer, such as a polyimide or parylene but can also be polyurethane or polysiloxane (silicon), or any other suitable insulator. For substantially non-flexible, or rigid embodiments, a rigid or semi-rigid substrate can be included. In some embodiments, the microelectrode array film 110 is formed on at least one surface of a rigid substrate, such as a planar ceramic member. Alternatively or in addition, one or more rigid or semi-rigid supporting members can be attached during fabrication to provide a desired amount of rigidity. Generally, the microfabricated component can be fabricated, for example, using a series of additive and subtractive processes that produce a stack of materials.

The supportive backing layer 120 provide a rigid or semi-rigid support to the microelectrode array film 110. It can be implemented in a variety of biocompatible materials, such as stainless steel, polyimide, or polyetheretherketone (PEEK). The supportive backing layer can be structured using laser micromachining processes, stamping, forming, or injection molding methods. In the case that the supportive backing layer 120 is of a conductive material, it may also form electrical ground for the stimulation or recording of signals. The supportive backing layer 120 is generally a relatively thin structure, between 50 um to 2 mm. The supportive backing layer 120 should be amenable to being slightly deformed in order to create protrusions from its surface, such as the case with the cortical depth probes 130 that it supports.

Mechanical components of the cortical neuromodulation device 100 include the supportive backing layer 120, and the control module 150. In some embodiments, the control module 150 may be implemented directly on the surface of the neurological surface probe 101. In the current embodiment it is implemented separately, but is attached via a ribbon cable tether 180. Alternatively, in some embodiments there is no control module 150, and the electrical conductors embedded in the microelectrode array film 110 and the ribbon cable tether 180 are connected directly to an external system through the patient's skin.

The electrical components can be discrete or microelectronic parts. Their purpose is to filter, route, generate, or process signals to and from the microelectrode elements 140. They can be attached to the control circuit 160 during production, or bonded afterwards. Alternatively, the can be bonded directly to the microelectrode array film 140. The loop antenna 165 is intended to transmit and receive signals in the control circuitry. All electrical components are generally contained within the control module 150.

The cortical neuromodulation device 100 can be implanted near a neurological target, such as a target brain structure, using common neurosurgical techniques such as stereotaxy or endoscopy. The cortical neuromodulation device 100 can be inserted without support, or attached to a stereotactic tool. Generally, the neurological surface probe 101 will be implanted in one surgical step, while the control module 150 will be implanted in an additional surgical step. The neurological surface probe 101 is intended to be implanted subdurally, through a craniotomy. The cortical depth probes 130 are intended to be rigid enough to penetrate the dura mater. However, the surgeon may also decide to create a flap of the dura mater during surgery, and thereby the neurological surface probe 101 will be implanted subdurally. The control module 150 is intended to be implanted on the surface of the skull and fixated to the bone matter using screws.

A clinician can direct the captured neurological recordings from the microelectrode elements 140 to a display unit. The information can be transmitted wirelessly using the loop antenna 165. Alternatively, in the case that the cortical neuromodulation device 100 does not include a control module 150, the information can be transmitted directly through the ribbon cable tether 180 to an external controller (not shown). The recorded data allows a clinician to identify certain regions of the brain according to their electrical activity. In some embodiments, such recording information can be processed automatically. The processing, or part of the processing, can be performed by the control circuit 160 before transmitting it wirelessly to an external controller. Alternatively, in the case that the cortical neuromodulation device 100 does not include a control module 150, the processing is performed entirely by the external controller (not shown). The microelectrode elements 140 used to record from the brain can be the same microelectrode elements 140 as those used to stimulate tissue. The recording electrodes can also be separate from those used to stimulate the brain. This situation might be preferred because electrodes destined for recording may be different in size and design than those for stimulation.

Figure 2:
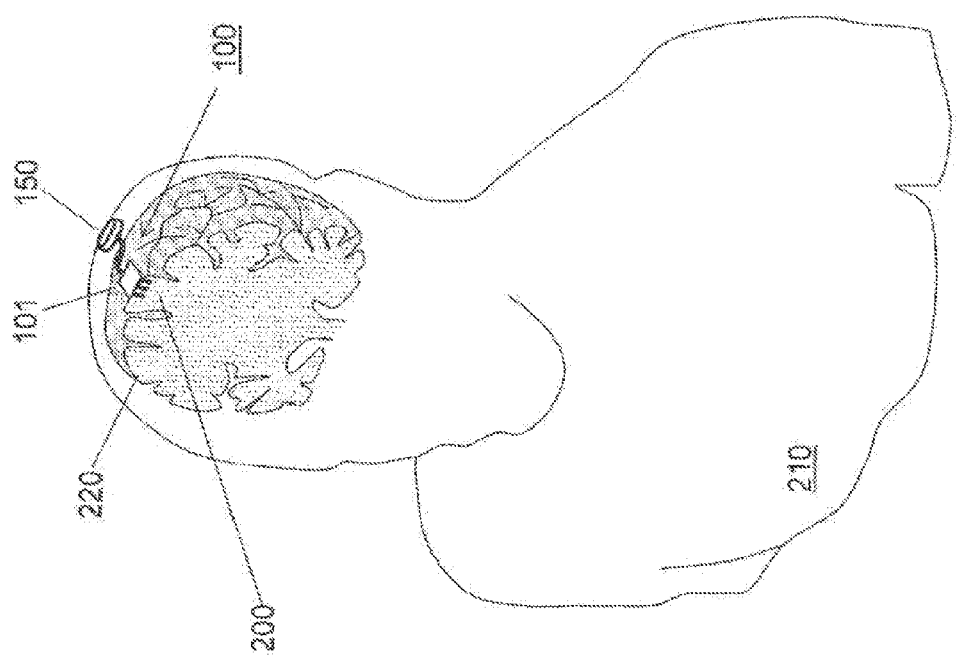
FIG. 2 is a perspective view of a portion of a human anatomy illustrating an exemplary cortical neuromodulation device implanted therein.

A perspective view of the portion of a human anatomy is illustrated in FIG. 2, showing implantation of an exemplary cortical neuromodulation device 100 positioned for interaction with a neurological target 200 located on the cortex of the human brain 220. The distal portion of the cortical neuromodulation device 100 is the neurological surface probe 101 and is positioned at the neurological target 200, in this instance located within the human brain 220. In this embodiment the proximal end of the cortical neuromodulation device 100, i.e., the control module 150, is attached to the distal end through a ribbon cable or wire bundle. This minimizes the size of the device implanted directly in the brain. In some embodiments the control module 150 is small enough to be integrated directly with the neurological surface probe 101. Alternatively, the control module 150 can be implanted at a remote portion of the subject body 210, such as the upper chest. One or more cortical neuromodulation devices 100 can be implanted in different cortical brain regions.

Figure 3:
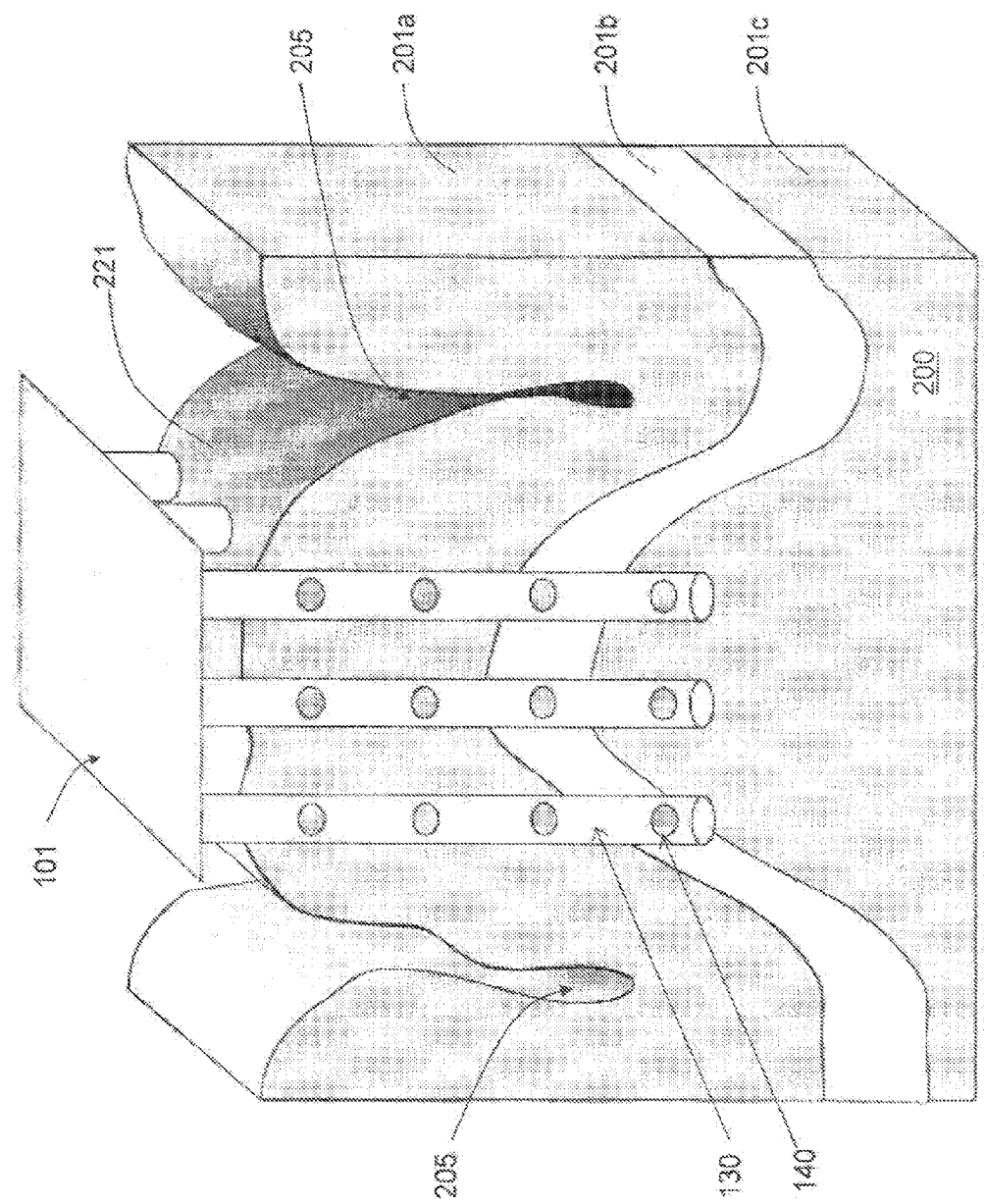
FIG. 3 is a cross-sectional view of a portion of a human cortex anatomy illustrating an exemplary neurological surface probe positioned on the surface of the brain.

Referring now to FIG. 3, a cross-sectional view of a portion of a human brain anatomy 200 is shown, illustrating an exemplary neurological surface probe 101 positioned at a neurological target 200 (e.g., the cortex as shown). The neurological surface probe 101 includes an array of nine cortical depth probes 130. On the surface of each cortical depth probe 130 is an array of microelectrode elements 140 distributed linearly. In this exemplary embodiment, there are four microelectrode elements 140 on each cortical depth probe 130. Preferably, the cortical depth probe 130 and microelectrode elements 140 are shaped and sized to allow one or more of the microelectrode elements 140 to be positioned in a clinically relevant cortical layer 210a 201b or 201c (collectively 201). Additionally, in some embodiments, it may be advantageous for the device to fit between two sulci 205, the natural folds of the cortex. This is important in terms of safety for the patient.

As illustrated, one or more of the microelectrode elements 140 (on the cortical depth electrodes 130 protruding from the neurological surface probe 101) are positioned in direct contact with the neurological target 200. The planar component of the neurological surface probe 101 remains on the surface of the brain 221. In some surgical procedures the planar component of the neurological surface probe 101 remains above the dura mater, while the cortical depth probes 130 are below the dura mater. In alternative surgical procedures the planar component of the neurological surface probe 101 is below the dura mater, requiring the formation of a flap of the dura mater during the surgery. Regardless of the formation of a dural flap during the surgery, in most procedures, the cortical depth probes 130 are subdural, and the microelectrode elements 140 are intended to be in contact with several cortical layers 201.

In some embodiments, selectable microelectrode elements 140 can be activated to record from the neurological target 200. Additionally, recordings of neurological activity from microelectrode elements 140 can be used to identify the location or position of the microelectrode element 140. For example, a microelectrode element 140 that is recording from cortical layer 201a will have a different signal that a microelectrode element 140 that is recording from a cortical layer 201b. As an additional example, a microelectrode element 140 that is recording from cortical layer 201b will have a different signal than a microelement 140 that is recording from cortical layer 201c. In the manner, the physician can determine the positioning of the microelectrode elements 140, and the neurological surface probe 101 in the neurological target 200.

In some embodiments, the microelectrode elements 140 that are used to record from the cortical surface 221 and cortical layers 201 are particularly useful in the diagnosis of epilepsy. The recorded activity in the patient can be used to determine the electrophysiological origin of an epileptic seizure, and can help the physician decide corrective or surgical action to be taken. In many cases the surgeon may recommend a surgical resection. If performed with this device, the precision of the resection may be improved and lead to better clinical outcomes. Additionally, if the resection is more precise, the patient may be able to keep additional neurological functionality that could have been lost to a larger resected area.

In some embodiments, selectable microelectrode elements 140 can be activated to stimulate a neurological target 200. Additionally, functional outcome of the neural stimulation can be used to identify the location or position of the microelectrode element 140 by a clinical evaluation of the patient undergoing the stimulation. For example, a microelectrode element 140 that is stimulating a cortical layer 201 in the motor cortex responsible for right hand index finger movement will experience twitching and or movement in their right hand index finger. As an additional example, a microelectrode element 140 that is stimulating in a cortical layer 201 in the auditory lobe may experience the perception of sounds. As an additional example, a microelectrode element 140 that is stimulating in a cortical layer 201 in the visual cortex may experience the perception of sight. In this manner, the physician can determine the positioning of the microelectrode elements 140, and the neurological surface probe 101 in the neurological target 200.

In some embodiments, the microelectrode elements 140 that are used to stimulate the cortical surface 221 and the cortical layers 201 are particularly useful in the treatment of stroke. The stimulation may not create a functional outcome such as movement of limbs, but may improve the ease with which patients can move. This stimulation applied to the microelectrode element 140 may be sub-threshold stimulation, meaning that it will not generate action potentials in neurons, but facilitate the ability of a neuron to reach the action potential threshold, by altering the extracellular potential.

In some embodiments, the microelectrode elements 140 that are used to stimulate the cortical surface 221 and cortical layers 201 are particularly useful in the treatment of chronic pain. The stimulation can be applied to a region of the sensor cortex where the physician has concluded that the region may be linked to the patient's pain. For example, a patient that presents himself with chronic pain in the face can implanted with the device in the general region governing sensation of the face in the sensory cortex. This stimulation can be applied to the microelectrode element 140 to suppress pathological activity in order to treat the pain.

Figure 4:
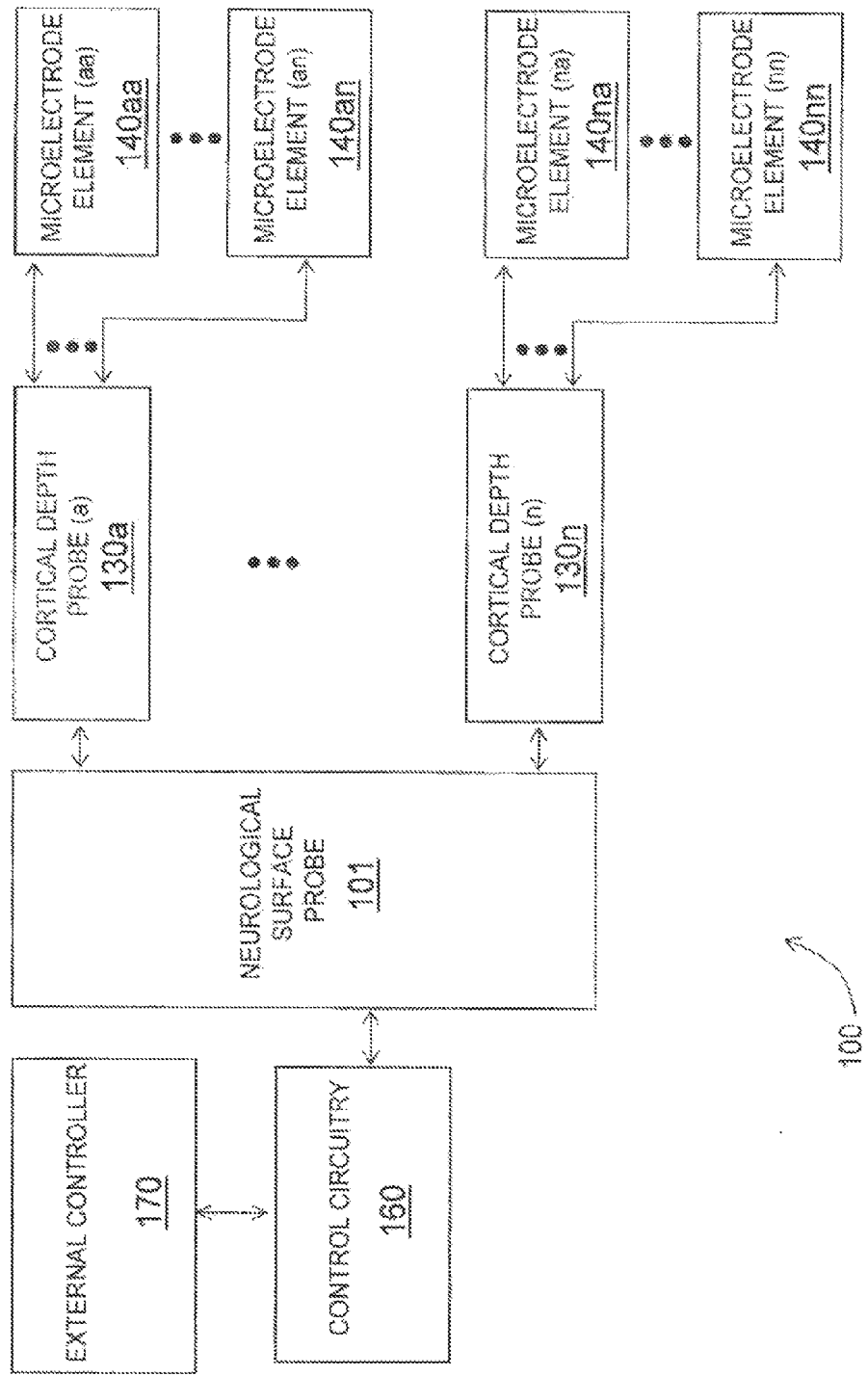
FIG. 4 is a schematic view of the components that are incorporated in the cortical neuromodulation device.

Referring now to FIG. 4, a schematic of the cortical neuromodulation device 100 is provided. The schematic begins with an external controller 170 which the operator can use to functions in the device. The external controller 170 can be in direct electrical contact with the control circuitry 160, or wirelessly connected through antenna circuitry. The control circuitry 160 is used to translate the commands from the external controller 170 to stimulate and or record from the device. The control circuitry 160 is also used to transmit captured information from the device to the external controller 170 for display or processing. Subsequently the control circuitry is electrical communication with the neurological surface probe 101. The communication is preferably through a tether wire or ribbon cable (not shown). Protruding from the neurological surface probe 101 are the cortical depth probes 130a through 130n (collectively 130), where n is an arbitrary quantity. Furthermore, each cortical depth probe 130 incorporates at least one microelectrode elements 140.

Figure 5B:
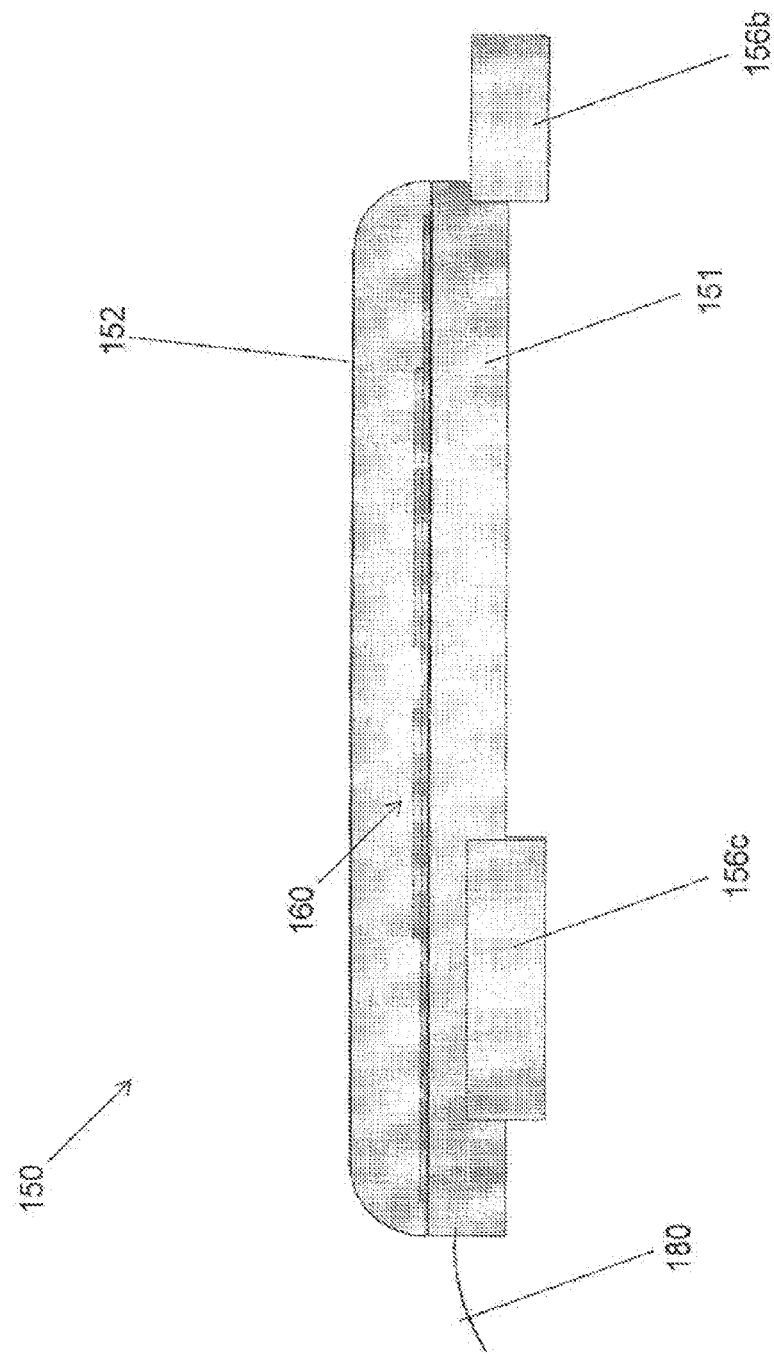
FIG. 5B is detailed view of the control module of the cortical neuromodulation device in FIG. 1.

Referring now to FIG. 5A, a top view of the exemplary embodiment in FIG. 1 is provided. FIG. 5B is a detailed planar view of the control module 150. The image demonstrates the curvature of the upper housing 152, and the shape of the lower housing 151. In particular, the fixation structures 156 are designed in order to be slightly offset from the planar surface of the lower housing 151 in order to be adaptable to all skull shapes, curvatures and sizes.

Figure 6A:
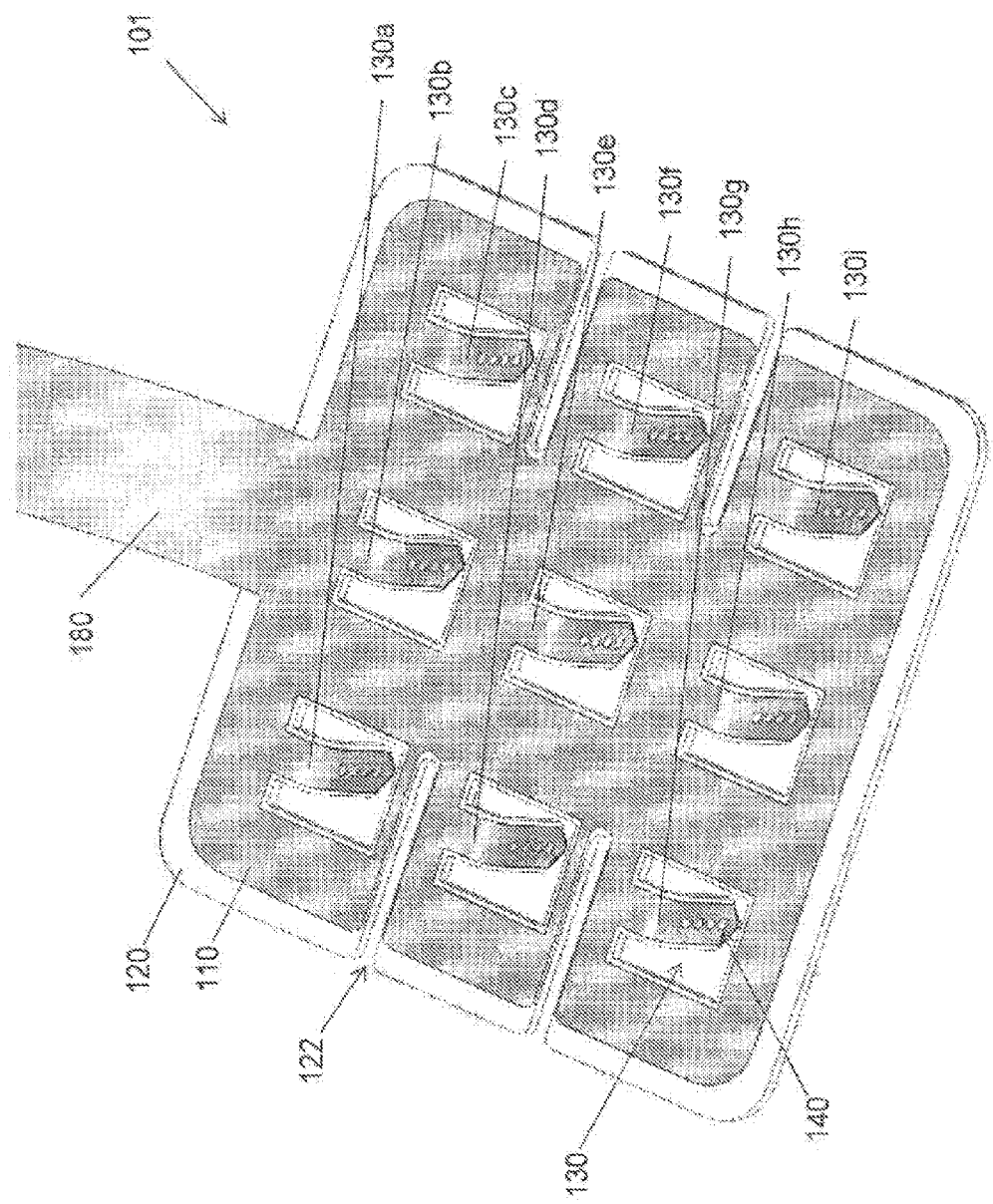
FIG. 6A is a detailed view of the neurological surface probe in FIG. 1.
Figure 6B:
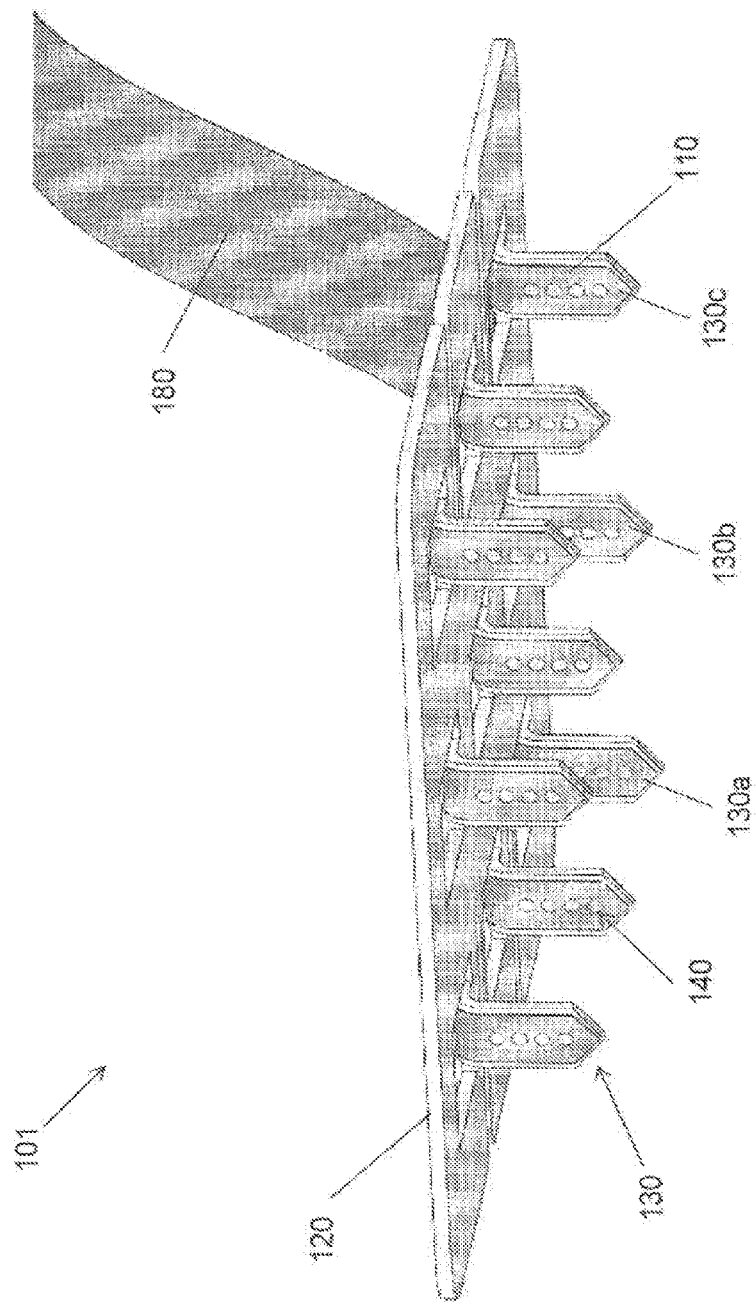
FIG. 6B is an additional detailed view of the neurological surface probe in FIG. 1.
Figure 6D:
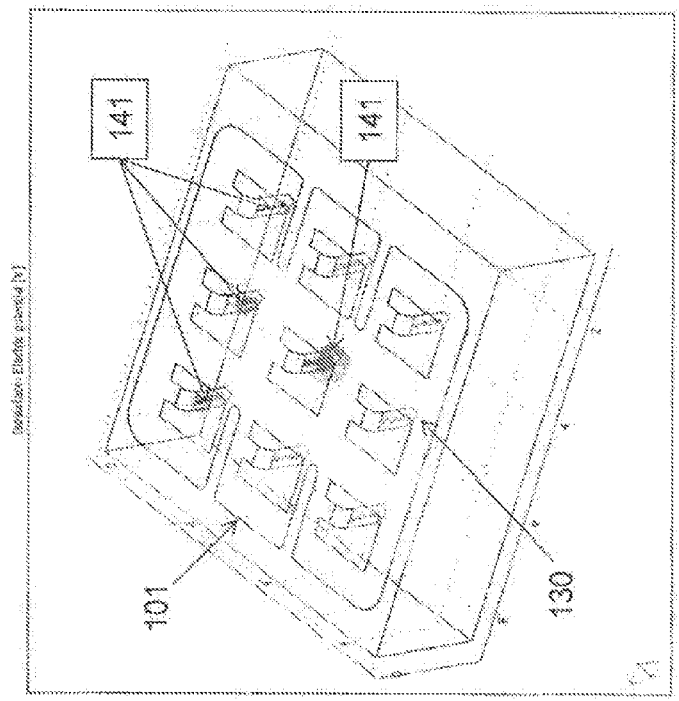
FIG. 6D is an additional perspective view of the neurological surface probe in FIG. 1 where currents have been applied to the microelectrodes demonstrating electrical field isosurfaces.
Figure 6C:
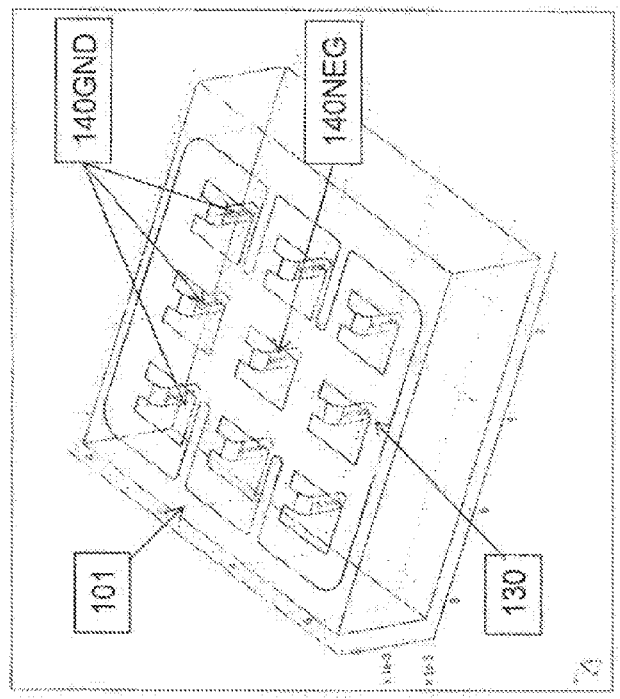
FIG. 6C is a perspective view of the neurological surface probe in FIG. 1 where currents have been applied to the microelectrodes.

Referring now to FIG. 6B, an additional perspective view of the neurological surface probe 101 is provided. In the image, cortical depth probes 130a through 130c are the most proximal. In FIG. 6C, a perspective view of the neurological surface probe 101 is demonstrated where currents have been applied to them are labeled 140NEG collectively. Microelectrodes that serve as electrical ground are label 140GND collectively. FIG. 6D demonstrates the electric field isosurfaces 141 that the applied currents would create. It is understood by those skilled in the art that any combination of signals (anodal, cathodal, ground) can be applied to any combination of microelectrodes 140 in order to create an arbitrary, or intentionally designed, three-dimensional electrical field in the tissue volume where the neurological surface probe 101 has been implanted.

Referring now to FIG. 6B, an additional perspective view of the neurological surface probe 101 is provided. In the image, cortical depth probes 130a through 130c are the most proximal.

Figure 7A:
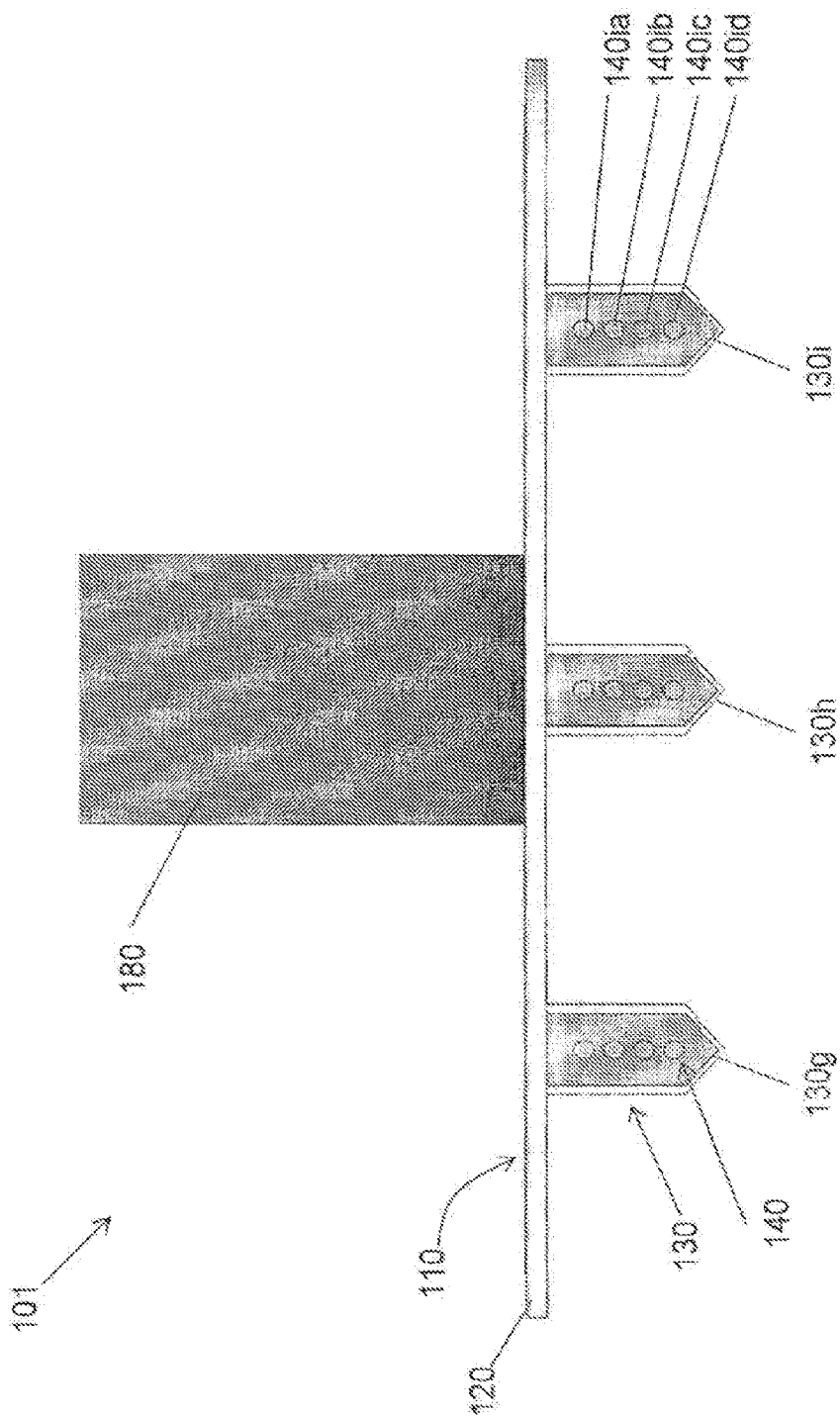
FIG. 7A is a front view of the neurological surface probe in FIG. 1.

Referring now to FIG. 7A, a frontal planar view of the neurological surface probe 101 is provided. In the image cortical depth probes 130g through 130i are shown. On cortical depth electrode 130i, the microelectrode elements 140 are labeled, 140ia through 140id. The microelectrode element 140ia is most proximal along the cortical depth probe 130i to the planar surface of the neurological surface probe 101. The microelectrode element 140id is most distal along the cortical depth probe 130i to the planar surface of the neurological surface probe 101.

Referring now to FIG. 7B and FIG. 7C, two additional planar views of the neurological surface probe 101 are provided. In the image cortical depth probes 130c, 130f, and 130i are shown. In FIG. 7B the cortical depth probe 130c is the proximal, whereas the cortical depth probe 130i is the most distal.

In FIG. 8A, a detailed perspective view of one cortical depth probe 130g is provided. In FIG. 8B an additional detailed perspective view of one cortical depth probe 130g is provided. The microelectrode elements on the surface of the cortical depth probe 130g are labeled 140ga through 140gd.

Figure 9:
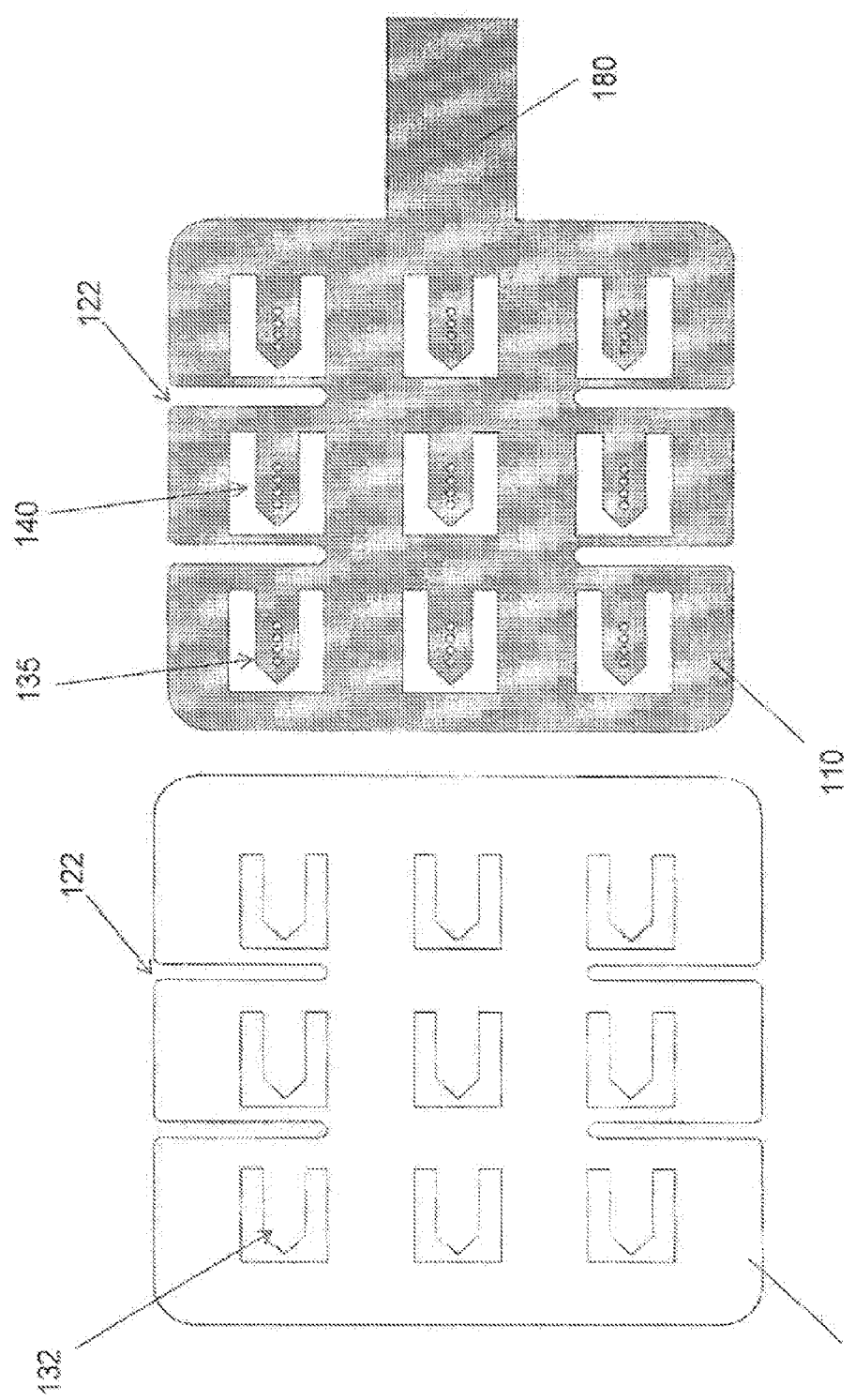
FIG. 9 is a top view of the supportive backing layer and microelectrode film that are incorporated in a neurological surface probe before they have been attached.

FIG. 9 partially demonstrates how the assembly of the neurological surface probe is performed. Additionally, in this example, the cortical depth probes 130 have not yet been bent down to protrude from the surface of the neurological surface probe 101. The supportive backing layer 120 has been constructed as described above. On its surface are cutouts of the structure that will create the cortical depth probe 130 which is here referred to as a cortical depth probe backing 132. Likewise, on the microelectrode array film 110, a structure referred to as the cortical depth probe film 135 is implemented. In this exemplary embodiment, there are nine cortical depth probe backings 132 and nine cortical depth probe films 135.

Figure 10:
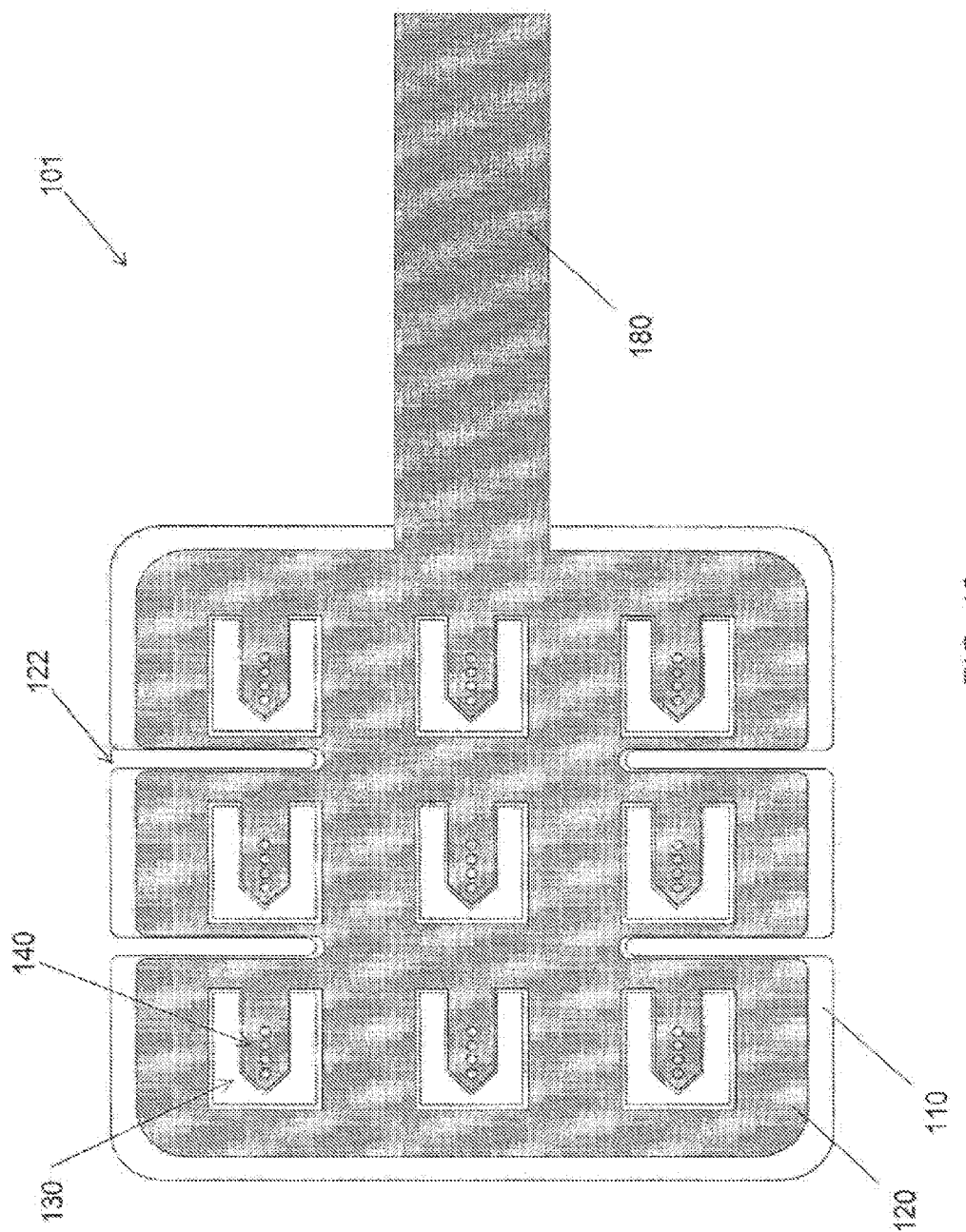
FIG. 10 is a top view of the supportive backing layer and microelectrode film that are incorporated in a neurological surface probe after they have been bonded.

By a process of bonding, the microelectrode array film 110 is attached to its supportive backing layer 120. FIG. 10 demonstrates the assembled neurological surface probe 101 after bonding, but before the cortical depth probes 130 have been bent down to protrude from the planar surface of the neurological surface probe 101.

Figure 11C:
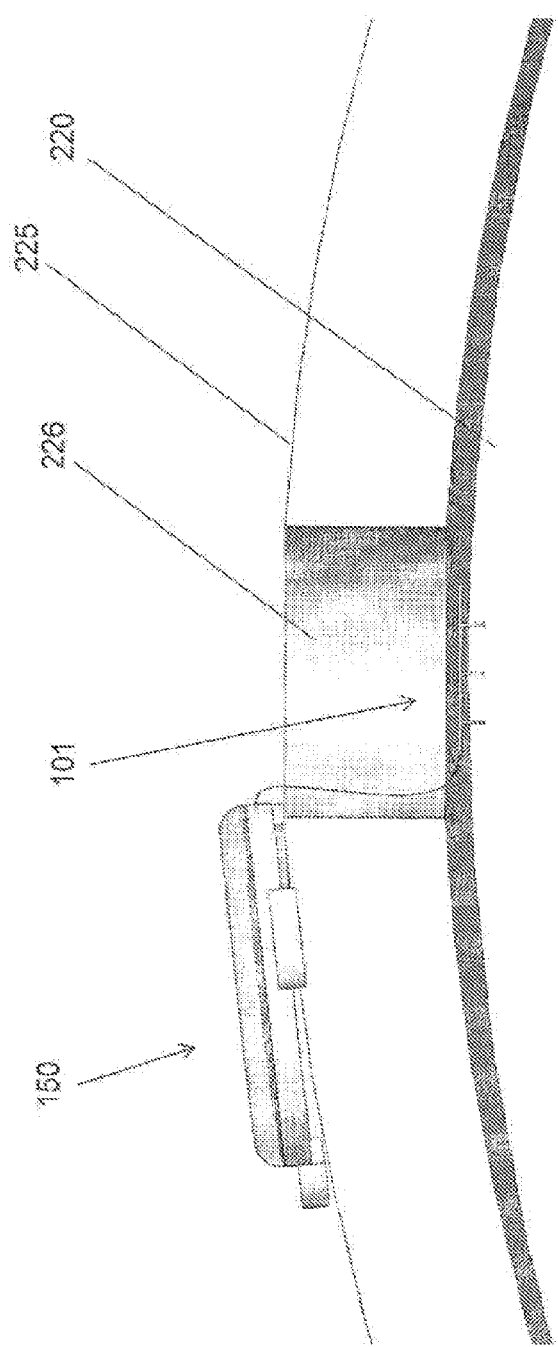
FIG. 11C is an additional planar view of a cross section of human anatomy demonstrating the placement of the cortical neuromodulation device of FIG. 1.

In use, the cortical neuromodulation device 100 is placed surgically through a craniotomy formed in the skull. FIG. 11A is a perspective view of the placement of the device. The image demonstrates a cross section of the brain surface 220 and skull 225. A circular craniotomy 226 has been performed in the skull. The neurological surface probe 101 has been surgically placed, with its cortical depth probes 130 piercing the dura mater (not detailed) and positioned subdurally. The control module 150 is placed on a different section of anatomy. It is surgically placed on the surface of the skull 225 and can be fastened using cranial screws. FIG. 11B demonstrates an additional perspective view of the cut-away anatomical region. FIG. 11C demonstrates an additional planar side view of the cut-away anatomical region.

Figure 12:
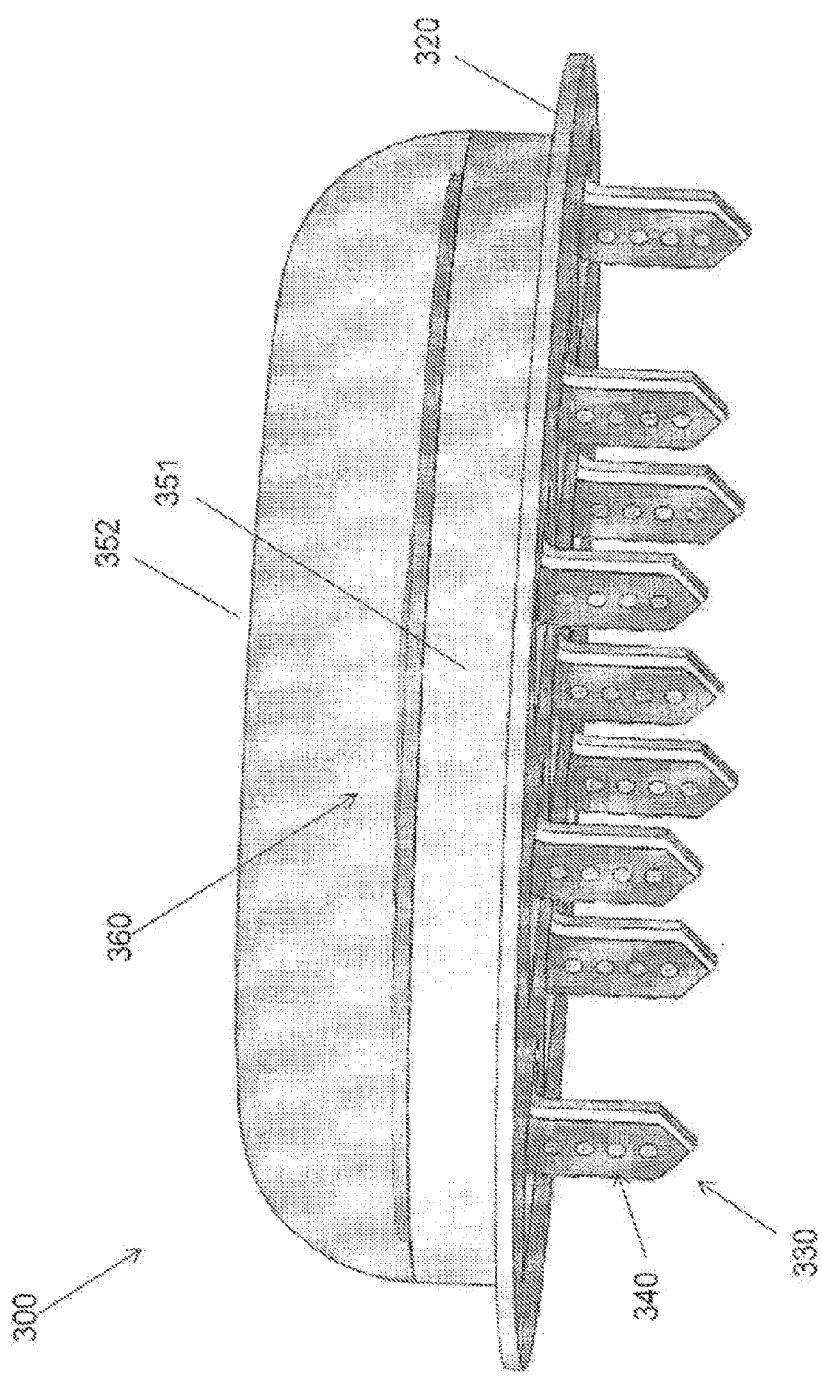
FIG. 12 is a perspective view of the alternative embodiment of the cortical neuromodulation device.

In some embodiments, it is preferably to integrate the control module with the neurological surface probe into one device, and avoid a wire or ribbon cable tether. The additional embodiment of an integrated cortical neuromodulation device 300 in FIG. 12 demonstrates the integration of all system components into one module.

Figure 13:
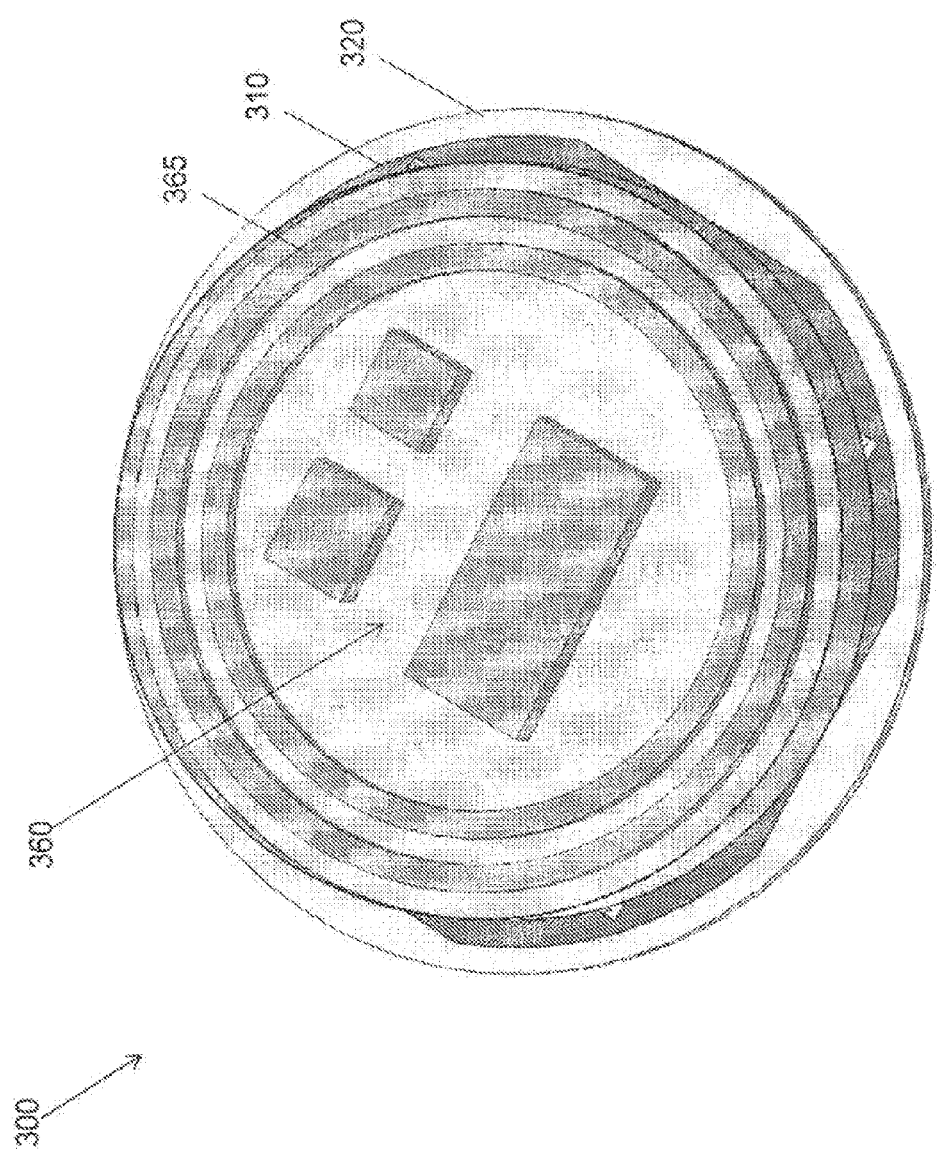
FIG. 13 is an additional perspective view of the alternative embodiment of the cortical neuromodulation device in FIG. 12.

FIG. 13 demonstrates an additional perspective view of the alternative embodiment. In some embodiments, the control circuitry 360 can be directly implemented on the microelectrode array film 310. Additionally, in some embodiments, the loop antenna 365 can be implemented on the microelectrode array film 310.

Figure 14:
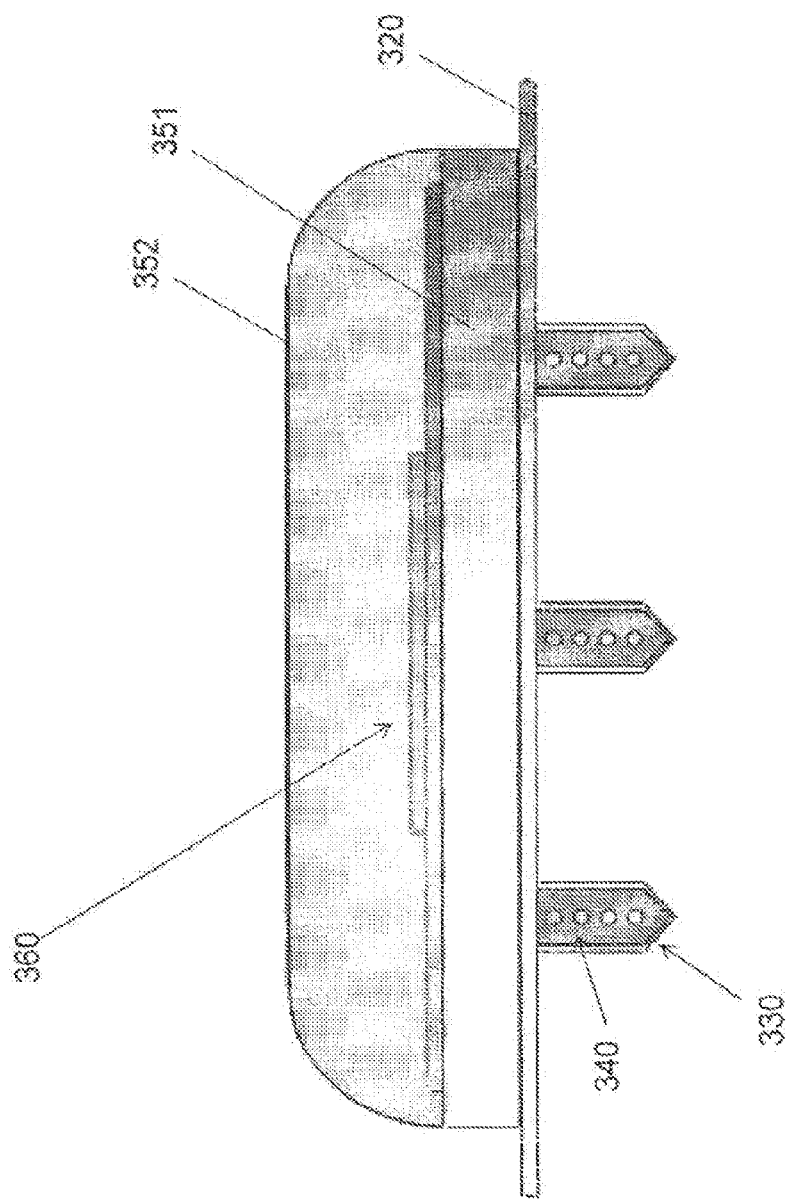
FIG. 14 is a top planar view of the alternative embodiment of the cortical neuromodulation device in FIG. 12.

FIG. 14 demonstrates a planar view of the integrated cortical neuromodulation device 300. The cortical depth probes 330 and their respective microelectrode elements 340 protrude from the lower surface of the device.

Figure 15:
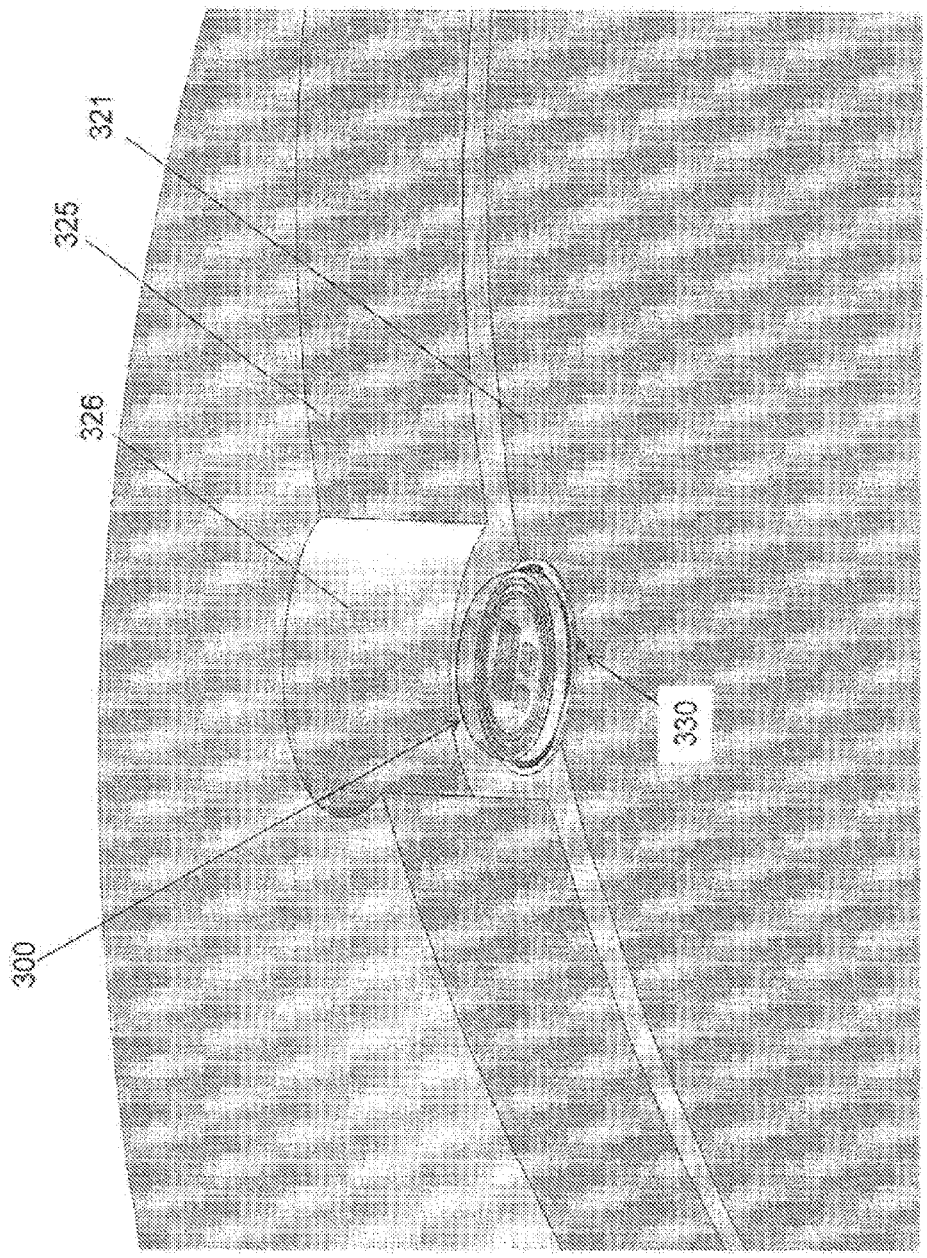
FIG. 15 is a perspective view of a cross section of human anatomy demonstrating the placement of the cortical neuromodulation device of FIG. 12.
Figure 16:
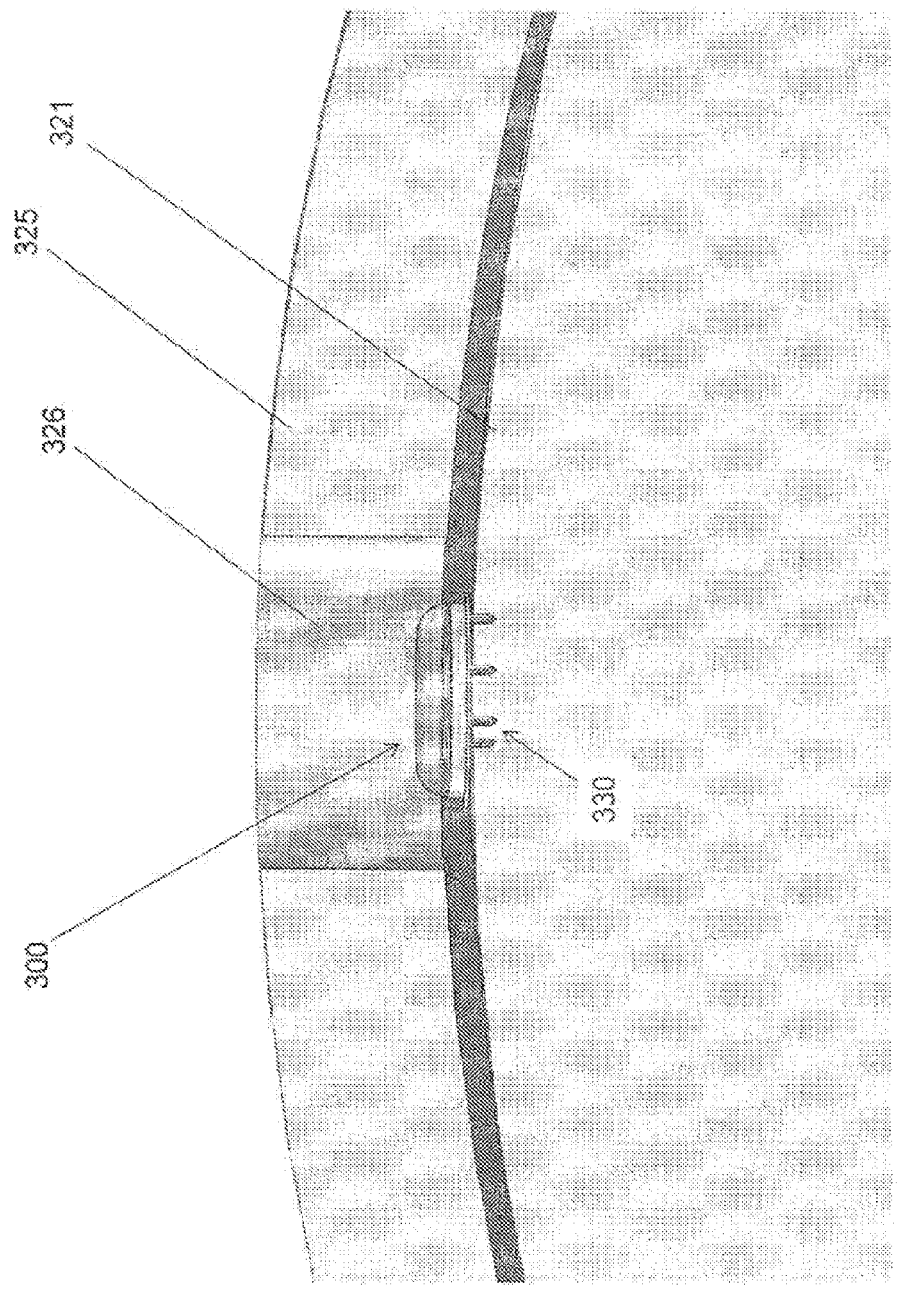
FIG. 16 is an additional perspective view of a cross section of human anatomy demonstrating the placement of the cortical neuromodulation device of FIG. 12.

In use, the integrated cortical neuromodulation device 300 is placed surgically through a craniotomy formed in the skull. FIG. 15 is a perspective view of the placement of the device. The image demonstrates a cross section of the brain surface 321 and skull 325. A circular craniotomy 326 has been performed in the skull. The integrated cortical neuromodulation device 300 has been surgically placed through the craniotomy, with its cortical depth probes 330 piercing the dura mater (not detailed) and positioned subdurally. FIG. 16 provides an additional planar view of the placement of the device in a cross section of human anatomy.

In some embodiments, it is preferably to have a circular neurological surface probe. FIG. 17A demonstrates a perspective view of a circular neurological surface probe 401. The device incorporates four cortical depth probes 430. On each cortical depth probe 430 a linear array of microelectrode elements 440 is implemented. Additionally, a large surface electrode 430, generally of diameter 3 mm, is used to record EEG signals from the surface of the brain. Finally, a ribbon cable tether 480 is used to communicate the microelectrode elements 440 to a control module (not shown) as described in previous embodiments. FIG. 17B demonstrates an additional perspective view of the circular neurological surface probe 401. In FIG. 17C, a perspective view of the circular neurological surface probe 401 is demonstrated where currents have been applied to a selection of microelectrodes 440. Microelectrodes that have a cathodal signal applied to them are labeled 440NEG collectively. Microelectrodes that serve as electrical ground are label 440GND collectively. FIG. 17D demonstrates the electric field isosurfaces 441 that the applied currents would create. It is understood by those skilled in the art that any combination of signals (anodal, cathodal, ground) can be applied to any combination of microelectrodes 440 in order to create an arbitrary, or intentionally designed, three-dimensional electrical field in the tissue volume where the circular neurological surface probe 401 has been implanted.

The circular neurological surface probe 401 is implemented by combining a supportive backing layer with a microelectrode array film. FIG. 18A demonstrates an exemplary circular supportive backing layer 420. It consists of a planar central body from which four cortical depth probe backings 432 protrude. Additionally, at the base of each cortical depth probe backings 432 are bending slits 433 that facilitate the bending of the probe into its final three-dimensional construction. FIG. 18B demonstrates the circular microelectrode array film 410 that is used in the current embodiment. It consists of four cortical depth probe film 435 on which the microelectrode elements 440 are disposed. The circular supportive backing layer 420 and the circular microelectrode array film 410 are bonded in a process that attaches them to each other. Subsequently, the cortical depth probes 430 are bent into place.

In some embodiments, it is preferable for a circular neurological surface probe to have a central cortical depth probe. FIG. 18C demonstrates an additional embodiment of a circular supportive backing layer 420C with an additional central cortical depth probe backing 432CM. It consists of a planar central body from which four cortical depth probe backings 432C protrude, and a central cortical depth probe backing 432CM of the same length and dimensions projects from the center of the circular supportive backing layer 420C. Additionally, at the base of each cortical depth probe backings 432C are bending slits 433C that facilitate the bending of the probe into its final three-dimensional construction. Additionally, at the base of the central cortical depth probe backing 432CM are bending slits 433CM that facilitate the bending of the central probe into its final three-dimensional construction.

FIG. 18D demonstrates the circular microelectrode array film 410C that is used in the current embodiment. It consists of four cortical depth probe films 435C on which the microelectrode elements 440C are disposed. Additionally, a central cortical depth probe film 434CM of the same length and dimensions projects from the center of the circular microelectrode array film 410C. The circular supportive backing layer 420C and the circular microelectrode array film 410C are bonded in a process that attaches them to each other. Subsequently, the cortical depth probes are bent into place, with the central cortical depth probe taking a position that is normal to the plane formed by the planar section of the supportive backing layer 420C.

Referring now to FIG. 18E, a perspective view of the circular neurological surface probe with central pin 401C is demonstrated. The components demonstrated in FIG. 18C and FIG. 18D are assembled to implement this embodiment. It consists of four cortical depth probes 430C and a central cortical depth probe 430CM. Microelectrode elements 440C are disposed on all five cortical depth probes. The central cortical depth probe 430CM of the same length and dimensions as the cortical depth probes 430C project from the center of the circular neurological surface probe 401C surface. The circular supportive backing layer 420C and the circular microelectrode array film 410C are bonded in a process that attaches them to each other. Subsequently, the cortical depth probes are bent into place, with the central cortical depth probe taking a position that is normal to the plane formed by the planar section of the supportive backing layer 420C.

Figure 19B:
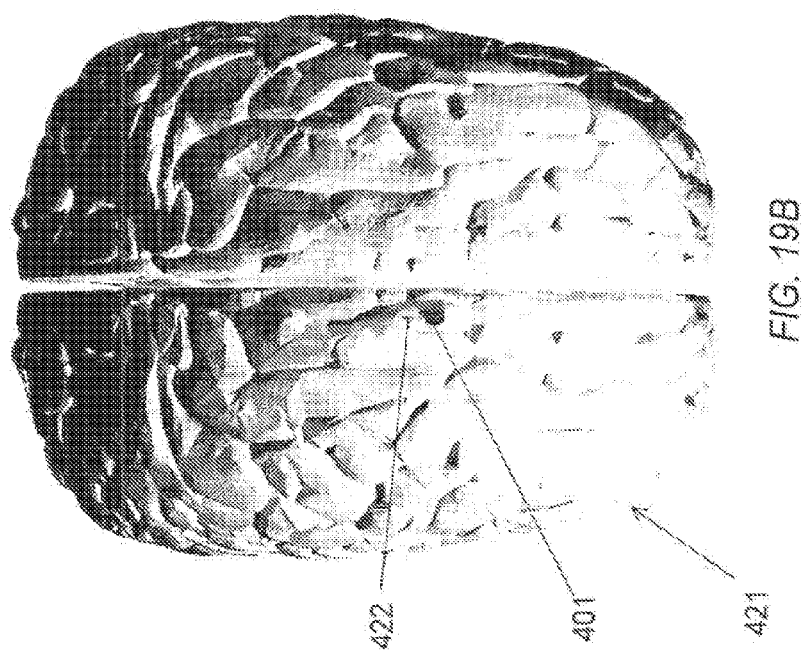
FIG. 19B is an additional planar view of human brain anatomy demonstrating the placement of the circular cortical neuromodulation device of FIG. 17A.
Figure 19A:
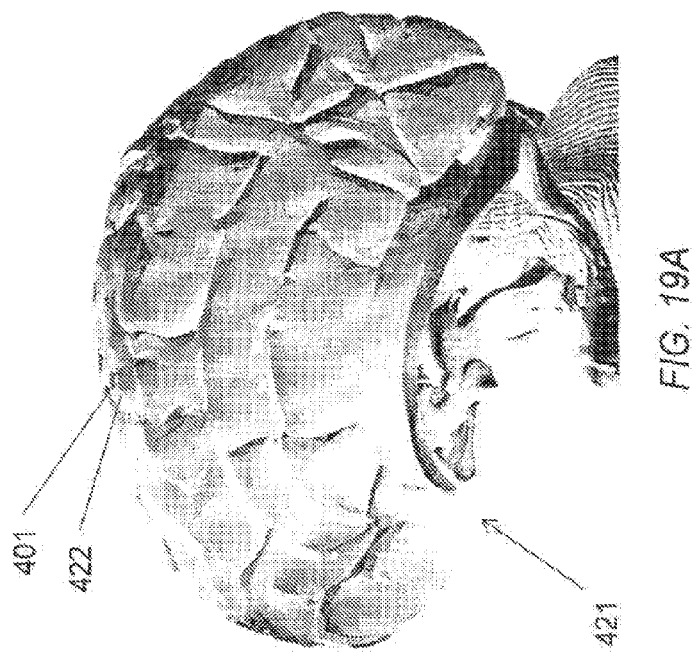
FIG. 19A is a planar view of a cross section of human brain anatomy demonstrating the placement of the circular cortical neuromodulation device of FIG. 17A.

Referring now to FIG. 19A a cross-sectional view of a portion of human brain anatomy 421 is shown, illustrating the exemplary circular neurological surface probe 401 positioned as a neurological target 422. In general, circular neurological surface probe 401 is representative of any of the cortical neuromodulation devices described herein. The circular neurological surface probe 401 includes an array of microelectrode elements along its individual cortical depth probes. Preferably, circular neurological surface probe 401 is implanted using by performing craniotomy. Its ribbon cable tether 480 remains outside of the human body, while the circular neurological surface probe 401 is implanted on the surface of the cortex of the brain. As in other embodiments, individual cortical depth probes are meant to be implanted subdurally, with the microelectrode elements in contact with at least one of the subdural layers of the cortex.

Referring now to FIG. 19B, a planar view of the positioning of the exemplary circular neurological surface probe 401 in a portion of human brain anatomy 421 referred to as the neurological target 422. As illustrated, one or more of the microelectrode elements circular neurological surface probe 401 are positioned in intimate contact with the neurological target 422. One or more additional microelectrode elements of the circular neurological surface probe 401 may reside at location not in the immediate vicinity of the neurological target 422. In at least some embodiments, one or more of the microelectrode elements are remotely accessible from a proximal end of the circular neurological surface probe 401 via one or more electrically conductive leads (not shown).

In some surgical procedures it would be highly beneficial to the patient to have several circular neurological surface probes 401 implanted in the region of the neurological target 422K. FIG. 20A demonstrates a cross-sectional view of a portion of human brain anatomy 421K, illustrating four exemplary circular neurological surface probes 401K positioned at a neurological target 422K. FIG. 20B is a more detailed close-up view of the neurological target 422K. Four circular neurological surface probes 401Ka, 401Kb, 401Kc, 401Kd (collectively 401K) were implanted in the neurological target 422K. It is highly beneficial in some surgical procedures to avoid the sulci 405K on the surface of the brain. The sulci 405K are regions where the brain surface folds and may be highly vascularized. The circular neurological surface probes 401K each have a ribbon cable tether, collectively 480K, that can lead to the external portion of the patient.

In practice the physicians will determine how many circular neurological surface probes 401K should be implanted. In some cases, it might be beneficial to implant only one, as the physician might determine that this will provide enough physiological information, or enough of a therapeutic stimulation volume. In some cases, it will be beneficial to implant a multiplicity of circular neurological surface probes 401 in the region, in order to increase the probability of finding the neurological target. The decision to implant a certain quantity of devices may be taken before the surgery, using surgical planning software. Alternatively, or in addition, the decision can be taken during the surgery.

Figure 21A:
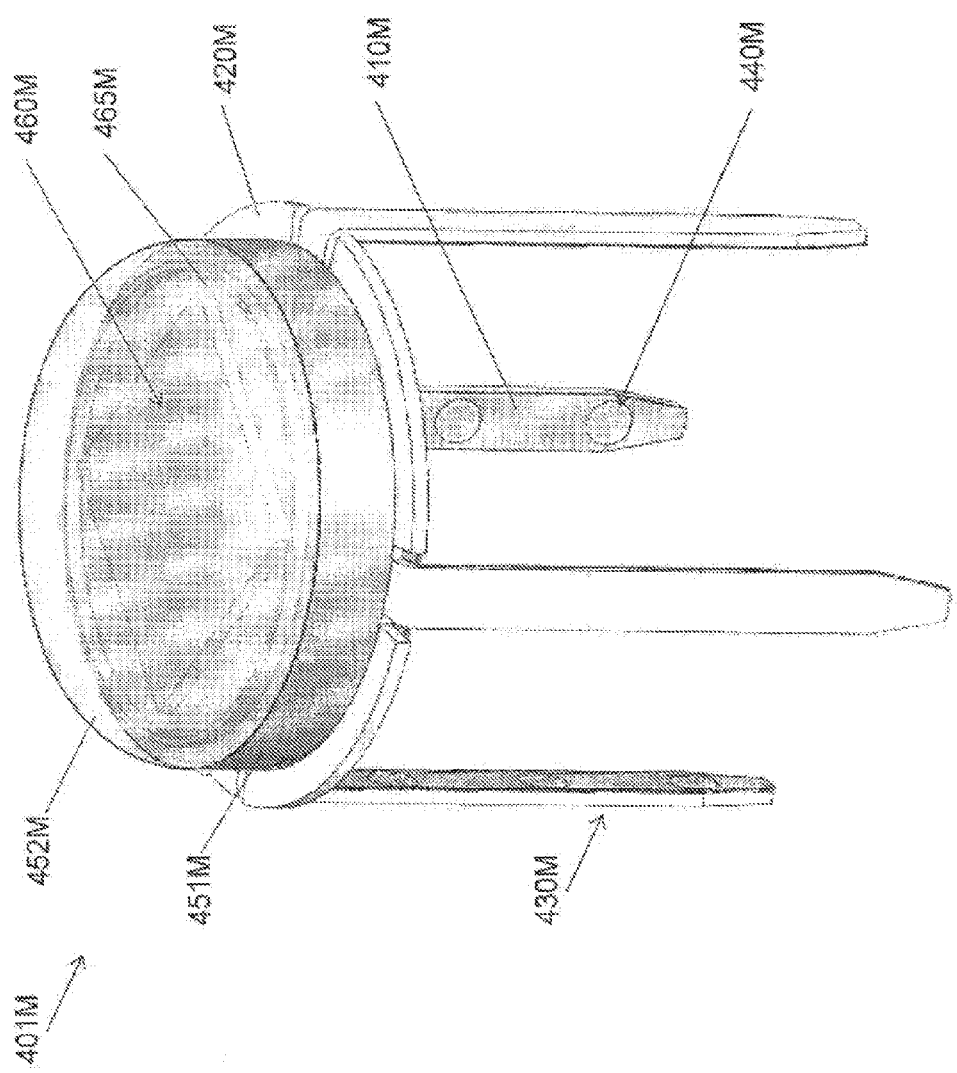
FIG. 21A is a perspective view of an additional embodiment of a circular cortical neuromodulation device.

In some embodiments, it is preferable to integrate the control module with the circular neurological surface probe into one device, and avoid a wire or ribbon cable tether. The additional embodiment of an integrated circular cortical neuromodulation device 401M in FIG. 21A demonstrates the integration of all system components into one module. The device incorporates four cortical depth probes 430M. On each cortical depth probe 430M a linear array of microelectrode elements 440M is implemented. Additionally, a lower housing 451M for control module is implemented directly above the planar region of the circular supportive backing layer 420M. The upper housing 452M is intended to encapsulate the control circuitry 460M and loop antenna 465M which are used to control and transmit information to the integrated circular cortical neuromodulation device 401M. On the surface of the circular microelectrode array film 440M are microelectrode array elements 440M which are in communication with the control circuitry 460M through embedded conductive traces (not shown). FIG. 21B demonstrates an additional perspective view of the integrated circular neurological surface probe 401M. In this image, the implementation of an EEG electrode 441M of 3 mm diameter is visible. FIG. 21C is an additional planar view of the exemplary integrated circular cortical neuromodulation device 401M.

Referring now to FIG. 22, a perspective view of a human brain anatomy 421M is shown with the exemplary embodiment of the integrated circular cortical neuromodulation device 401M implanted in a neurological target 422M. In this exemplary embodiment, the connection of a ribbon cable tether the external portion of the patient is not necessary. However, an external control module (not shown) is required to communicate with the implanted device. FIG. 23 demonstrates a more detailed view of the portion of human anatomy 421M and the positioning of the exemplary circular neurological surface probe 401M in the neurological target 422M.

In some surgical procedures, it would be highly beneficial to the patient to have several integrated circular neurological surface probes 401M implanted in the region of the neurological target 422M. FIG. 24 is a close-up perspective view of a portion of human brain anatomy 421M, illustrating five exemplary integrated circular neurological surface probes 401Ma, 401Mb, 401Mc, 401Md, 401Me (collectively 401M) positioned at a neurological target 422M. It is highly beneficial in some surgical procedures to avoid the sulci 405M on the surface of the brain. The sulci 405M are regions where the brain surface folds and may be highly vascularized. The integrated circular neurological surface probes 401M can wirelessly communicate to the external portion of the patient.

In all of the embodiments presented, it is understood that the devices are meant to be implanted using a surgical procedure on the surface of the brain. Additionally, it is intended that the cortical depth probes which protrude from all embodiments are meant to be in subdural region or the brain, and the microelectrode elements on the surface of the cortical depth probes are meant to be in contact with at least one of the cortical layers. The neurological surface probes are placed on the brain generally for recording and/or stimulation of the cortex. The region of the cortex that the physician is target for diagnosis of therapy is termed the neurological target.

The microelectrode elements can also be placed in other parts of the body, such as the retina, the peripheral nervous system for neural recording and/or neural stimulation of such portions of an animal anatomy. Although microelectrodes are discussed generally throughout the various embodiments, there is no intention to limit the upper or lower size of the microelectrodes. The devices and methods described herein are generally scalable, with a microelectrode size determined according to the intended application. For at least some of the neurological applications, microelectrodes are dimensioned sub-millimeter. In some embodiments, microelectrodes are dimensioned sub-micron. In some embodiments, the microelectrodes are formed as planar structures having a diameter of about 50 µm that are arranged in a linear array with center to center spacing of about 100 µm. The planar structure of the microelectrodes can have regular shapes, such as circles, ellipses, polygons, irregular shapes, or a combination of such regular and/or irregular shapes.

FIG. 23A is a schematic diagram of one embodiment of a cortical depth probe assembly. The microelectrode tip assembly 500 includes a supporting member 502 including an elongated portion terminating in a distal tip 506 and a proximal extension 510. A linear array of three microelectrode elements 504 is arranged along a longitudinal axis of the elongated portion of the support member 502. A corresponding number of three electrode contacts 508 are located on the proximal extension 510. Each microelectrode element of the array 504 is interconnected to a respective one of the electrode contacts 508 through a respective electrically conducting lead trace 512. In the exemplary embodiment, a polymer layer 514 is applied to at least one surface of the underlying support member 502. Each of the microelectrode leads, electrode contacts 508, and interconnecting lead traces 512 is implemented as an electrically conducting layer on or within the polymer layer 514. Although a linear array of microelectrode elements is shown, other embodiments are possible with nonlinear, planar, curved surface, and volumetric (i.e., three-dimensional) distributions of such microelectrodes are possible.

Fabrication Methods

There are several techniques to achieve the microfabricated components and the required mechanical and electrical characteristics. The fabrication procedure is a series of procedural steps in which various layers are deposited or removed (e.g., etched) to achieve a final form. Exemplary sequence of procedural steps is described herein.

Step 1: The Carrier Wafer and Sacrificial Layer

In a first step illustrated in FIG. 23A, a carrier substrate 650 is provided, such as a wafer composed of a crystalline material, such as Silicon, or an amorphous material, such as glass, in particular a thermal shock resistant borosilicate glass commercially available under the grand name PYREX®, or other suitable smooth supportive material. A first layer 652 comprising at least two sub-layers is applied to a surface of the water 650. One of the sub-layers 652 is a sacrificial layer deposited on the wafer 650, which will be removed in a subsequent electrochemical etch step. Preferably, the sacrificial sub-layer is preceded by another sub-layer, referred to as an underlayer, that will serve to form the electrochemical cell required to etch the sacrificial layer. In the preferred embodiment, the sacrificial sub-layer is Aluminum, or an alloy of Aluminum such as AlSi, which has a smaller granularity, whereas the underlayer is a TiW alloy, Chrome, or similar metal. The sacrificial layer is represented as a black line 652 in the image below, the carrier wafer 650 is shown in gray. Each of the images illustrated in this series represents a cross section of an exemplary embodiment, and are used herein to describe the procedural steps.

Figure 30:
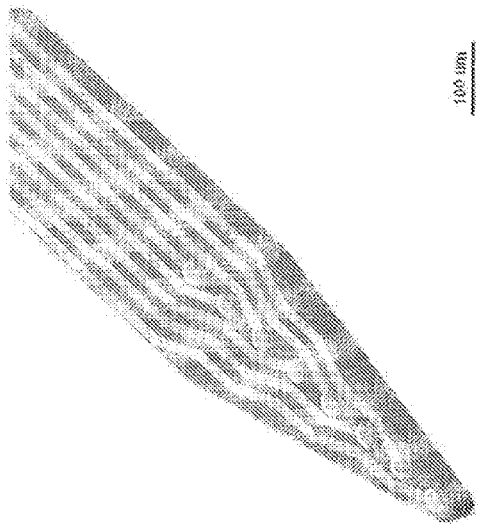
FIG. 30 is a schematic view of another portion of the construction element.

In some embodiments, the sacrificial layer 652, in addition to facilitating electrochemical removal of the finished device, is to establish a granularity, or grain size to the surface of the finished device. Namely, the sacrificial layer can add a micro or nano-roughness to the surface that can be precisely controlled at least in part by the selection of a suitable underlayer. For example, Aluminum can be deposited by DC Sputtering with a grain size ranging from 5 nm or less to 600 nm or more. This grain size provides a first grainy surface. A polymeric layer is subsequently deposited over the grainy sacrificial layer. This polymeric layer can be locally etched in order to create vias that open onto the grainy sacrificial layer. Subsequently, a metal layer is deposited over the resulting grainy surface, and polymeric layer, in which the deposited metal serves as the neuro-recording/stimulation microelectrode element, and wire trace. The area of the metal that falls into the via in the polymeric layer forms the microelectrode surface. The area of the metal falls on the polymeric layer can be etched into linear traces and form the interconnect between microelectrodes and bond pads or circuitry. The process is described below as a "backside microelectrode." Due to such an increase in granularity over a relatively flat surface, the overall surface area of the metal layer will have a higher effective surface area than that area subtended by the perimeter of the element. Beneficially, the increased surface area results in a corresponding decrease in electrical impedance of the electrode element. This concept is important in that it facilitates recording, allowing a greater recording fidelity with less complexity due to the reduction in impedance, while maintaining the same small diameter that guarantees high localization of the neural activity. An electrically conducting surface of an exemplary microelectrode element thus formed is illustrated in the image of FIG. 30.

Step 2: Deposition of First Polymeric Layer

Referring to FIG. 25B, the next step in the fabrication process includes depositing a first polymeric layer 654—sometimes referred to as a resin layer 654. The first polymeric layer 654 can be deposited upon the sacrificial layer 652. This can be done by any suitable means known to those skilled in the art of MEMS processing, by: (i) spin coating a liquid polymer precursors such as Polyimide or Silicone precursor; (ii) depositing a polymer through chemical vapor deposition as is done with parylene-C; or (iii) laminating a polymer sheet 654 onto the wafer 650. In some embodiments, the polymer layer 654 is heated, or baked, to polymerize.

Referring next to FIG. 25C and FIG. 25D, an optional step includes etching of first polymeric layer 654, as may be beneficial when preparing a device having one or more backside electrodes, that will ultimately be located along an underside of the finished device. In this optional step, the first polymeric layer 654 is locally etched in order to form open areas 652, where metals for such backside microelectrodes may be later deposited. This step is optional, and unnecessary when there is not need for any such backside electrodes on the finished device—all microelectrode contacts being formed on a front surface of the finished device. This step is also advantageous, because the backside electrode metal layer, when included, will also benefit from the higher effective surface area that can be gained from the sacrificial layer's granularity.

The etching can be performed by depositing a mask 656 on the first polymeric layer 654. Using well established methods for thin film processing, the mask 656 can be photolithographically defined. For example, a photosensitive resin 656 is spin coated onto the polymeric layer 654. A process of exposing an unmasked portion of the resin layer 657 to UV light is used for those areas in which the operator chooses to remove the polymer layer 654. The device is developed in a solvent that will selectively remove only the unmasked areas 657 that were exposed to UV light. This selective etching process locally opens areas of the polymeric layer 654, by etching, exposing in this instance the underlayer 652. In some embodiments, the device is etched in oxygen plasma to remove the exposed portion of the polymeric layer 657. The etch mask 656 may also be removed by the same etching process, but if it is thicker than the polymer layer it may not be completely removed. Illustrated in the figures is a defined etch mask 656. Alternatively or in addition, the etch mask 656 can also be implemented in a non-photodefinable layer, such as Silicon Dioxide deposited by DC Sputtering. The Silicon Dioxide then has the photoresist deposited and photolithographically defined on top of it. After etching the polymeric layer 654, the Silicon Dioxide mask can be optionally removed.

FIG. 25D illustrates the device after the exposed portion of the polymer layer 657 was removed. As illustrated, a portion of the sacrificial layer 652 is now exposed. In some embodiments, the photoresist mask 656 can be subsequently removed using a suitable solvent.

Step 3: Deposition and Definition of Metal Layer

The deposition of the layer can also be made through a resist mask 670, as shown in FIG. 25G. In this case a photoresist mask 686' would be photolithographically defined on the polymer layer 654. An electrically conductive (e.g., metal) layer 692' can then be deposited over the masked device. Thus, unmasked areas 687 at which it is desirable to have an electrically conducting layer 690 formed, are open with respect to the photoresist mask 686', such that the a portion of the deposited electrically conductive layer 692' lands directly onto the polymeric layer 654 at the unmasked area 687. This technique is sometimes referred to as a "lift off" technique. The photoresist mask 686', with any electrically conductive layer 692' thereon, is then dissolved, such that the only remaining metal 690 is on the polymer at the formerly unmasked areas. Note that the metal layer 692' on top of the photoresist 686' is also removed by removal of the photoresist mask 686'. Beneficially, that portion of the electrically conducting layer 690 in contact with the polymeric layer 654 remains after removal of the mask 686'.

In an alternative method, referring now to FIG. 25H, a metal layer 692" can be deposited onto the entire surface of a wafer 650. As illustrated, the metal layer 692" is provided on top of the polymeric layer 654, which is provided on top of the sacrificial layer 652. A masking layer 686" is provided over that portion of the metal layer 692" to remain. Exposed regions of the metal layer 692" can then be removed locally by a photolithographic step such as demonstrated below.

Referring next to FIG. 25E, an electrically conductive layer that serves as the electrode 680 and one or more electrically conductive traces 682 is next deposited. Such an electrically conductive layer can include a metal layer deposited by any suitable thin-film process, such as DC sputtering, RF Sputtering, or evaporation techniques. The metal deposited in the electrically conductive layer 680, 682 is preferably platinum, iridium, platinum-iridium alloy, iridium-oxide, titanium, or a titanium alloy to ensure acceptable electrical characteristics (such as charge transfer) and mechanical strength.

In a preferred embodiment, the metal layer 680, 682 is deposited with an adhesion promotion layer in contact with the polymer. For example, titanium can be sputtered onto the polyimide layer 654 in an initial partial step to improve adhesion, followed by a platinum layer deposited in an intermediate partial step, and optionally, a titanium layer may then be deposited onto the platinum layer in a subsequent partial step. This creates a Ti—Pt—Ti sandwich, where the titanium is responsible for adhering the platinum to the polyimide on either side of it, and the platinum is the metal layer that will be used.

For embodiments that produce backside electrodes, as described above in reference to FIG. 25C through FIG. 25E, then the electrically conductive layer 680 will be in contact with the sacrificial layer 652 in the region of the backside electrode 680. The metal deposition technique is selected to ensure that there is contact between the metal on top of the polymeric layer 654, and the metal on the exposed portion of the sacrificial layer 652. This is done by ensuring the metal 680 is conformally deposited, and that the polymeric layer 654 is not too thick. The metal layer 680 can then be photolithographically defined as explained above. An etch in a plasma, such as Chlorine gas plasma, can be used to remove the metal layers deposited using a photoresist mask. The photoresist mask can then be removed in a solvent.

Step 4: Deposition of 2nd Polymeric Layer

Referring next to FIG. 25I for a backside electrode embodiment and FIG. 25H, a second polymeric layer 672, 692 is deposited using a suitable technique, such as any of the techniques described above with respect to FIG. 25B. The second polymeric layer 672, 692 is deposited onto the underlying polymeric layer 654, 664, and any exposed metal layer 658, 668. In some embodiments, the first polymeric layer 654, 664 can be processed in order to increase its adhesion to the second polymeric layer 672, 692. For example, such processing can be accomplished through surface roughening or chemical alteration using an oxygen plasma. The second insulative, or polymeric layer 672, 692 isolates the electrical traces, when formed on different layers with respect to each other. In some embodiments, the polymeric material can be subjected to thermal process, such as baking.

Step 5: Definition of Polymeric Layers

Referring next to FIG. 25I through FIG. 25K, to define the one or more polymer layers, 654, 691 and therefore the device itself, an etch mask 695 is deposited to an external surface of the device. This etch mask 695 may consist of a photodefinable resist but preferably it will be a hard etch mask such as silicon dioxide or amorphous silicon which can withstand the etch of the polymeric layer without significant degradation.

The wafer 650 at this point also has a hard mask 693 deposited, for example by DC or RF sputtering. A photodefinable 695 resist is deposited on the hard mask 693 and the areas of the polymer 654, 691 that are to be etched are defined.

The hard mask 693 is then etched with a different gas then would be used to etch the polymeric layer 654, 691, for example CF4 plasma. Now the one or more polymeric layer 654, 691 can be etched with a gas, such as oxygen plasma, to the sacrificial layer 652, as shown. Thus, the remaining portions of the hard mask shown in FIG. 25K define the extent of the device, by defining the device's edges 659.

Figure 31:
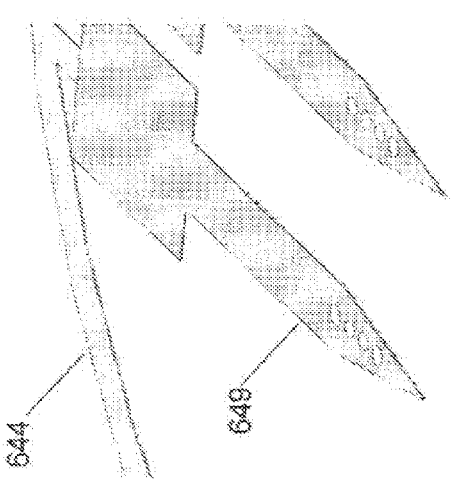
FIG. 31 is a perspective view of a distal portion of a microelectrode tip.
Figure 32:
FIG. 32 is a cross sectional view of the distal portion of the microelectrode tip illustrated in FIG. 31.

The remaining portions of the hard mask 693 can be optionally removed in a subsequent step. The goal of this etching process is to: (i) define the microelectrode sites; (ii) define the device shape; and (iii) define the contact areas for electronics or wire attachment. A top view of an exemplary finished microelectrode device is shown in FIG. 31. A cross-section of another exemplary finished microelectrode device is shown in FIG. 32.

If the option of making backside electrodes is taken in step 2, the device will have microelectrodes at its surface once removed from the substrate.

Step 6: Optional Bonding of Electronics

If the device is to be integrated with electronics, referring now to FIG. 25L, the contact pads 699 can be used at this point to connect to an electrical circuit device 697. For example, an Integrated Circuit chip 697 can be connected to the contacts 690 (FIG. 25K) by flip-chip bonding the chip 697 to the device 661, using a conductive epoxy interlayer. The chip 697 can then be further attached by chemical bonding, such as an epoxy to sure a strong and reliable connection to the device 661.

Step 7: Removal of Devices from Carrier Wafer

A final step of the fabrication process is illustrated in FIG. 25M, to remove the device 661, such as a MEMs device, from the underlying wafer 650. The sacrificial layer 652 (e.g., FIG. 25L) is electrochemically etched away. Removal of the sacrificial layer 652 from under the device 661, frees the underside of the device 661 from the wafer 650. This can be accomplished by placing the wafer in a saline bath with a high NaCl concentration. A platinum electrode in the bath can be used as a reference. A voltage is applied to the aluminum layer with respect to the platinum electrode. The electrochemical cell created by the Aluminum and TiW etches the aluminum, and this etch continues below the devices. The devices fall into the bath and are removed.

Figure 26:
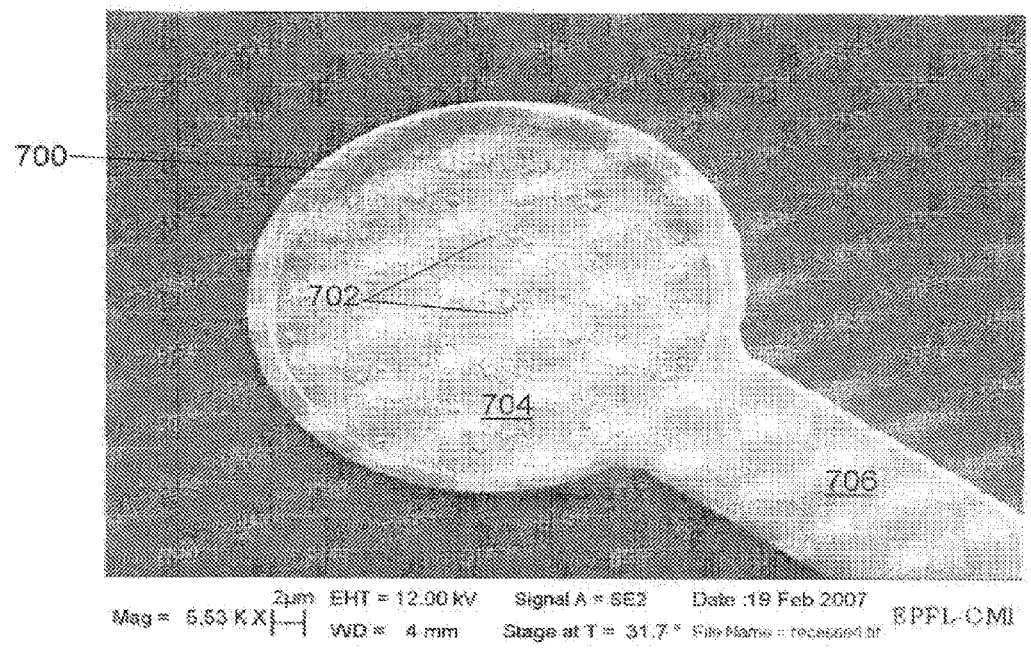
FIG. 26 is a micrograph of an embodiment of a microelectrode.

FIG. 26 is a micrograph of an embodiment of a backside microelectrode element 700. The image is taken at the process step shown in FIG. 25E. The granularity 702 of the aluminum sacrificial layer surface 704 is used to increase the effective surface area of a metal electrode in a subsequent step. Also shown is a portion of an interconnecting lead 706 in electrical communication with the microelectrode element 700.

Figure 27:
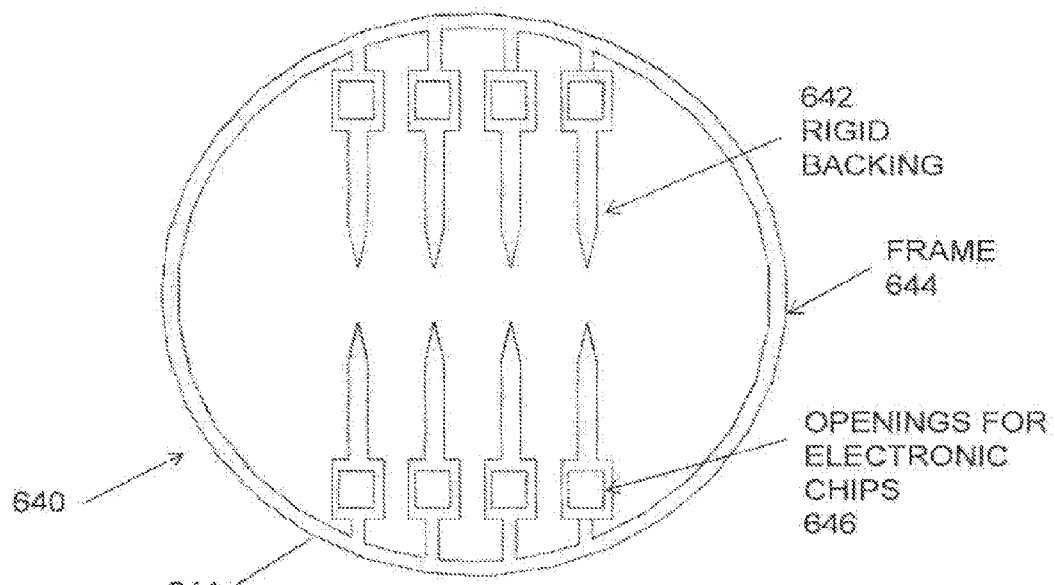
FIG. 27 is a planar view of a construction element of an embodiment of a microelectrode tip.

FIG. 27 is a planar view of a construction element of an embodiment of a microelectrode tip. The construction element includes a stencil frame tree 640 including eight rigid backing members 642 releasably attached to a supporting construction frame 644. Each of the rigid backing members 642 includes an elongated portion, and an proximal portion having an opening 646 to accommodate one or more electronic devices, when fabricated. The stencil frame tree 640 can be implemented in a rigid material, such that each of the individual supporting construction frames can be bonded to the devices on the carrier wafer.

Figure 28:
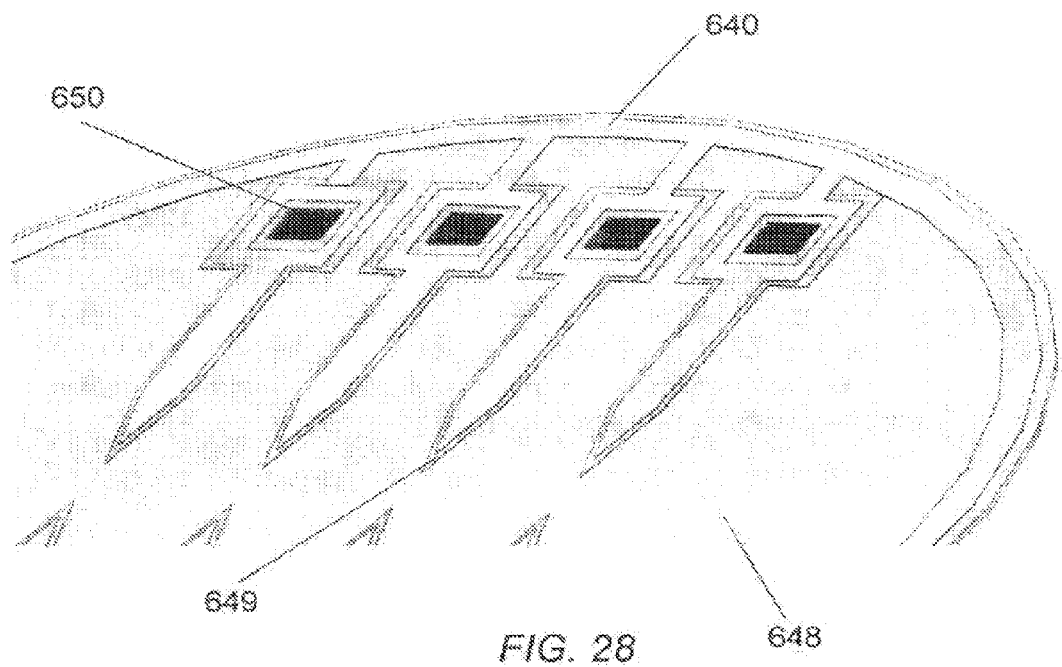
FIG. 28 is a schematic view of a portion of the construction element illustrated in FIG. 27.
Figure 29:
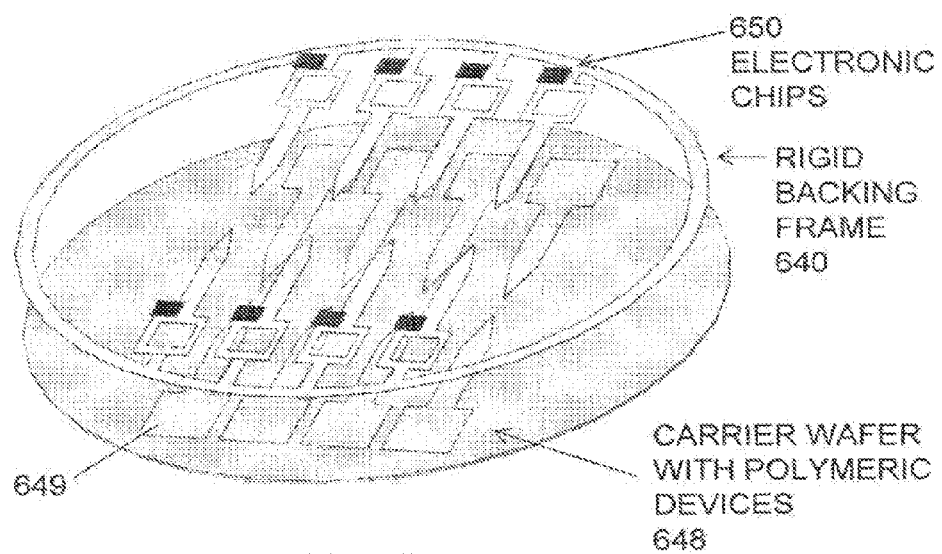
FIG. 29 is an exploded schematic view of a construction element of an embodiment of a microelectrode tip.

FIG. 28 is a schematic view of a portion of the construction element illustrated in FIG. 29, illustrating a close up of the assembled components. In this exemplary embodiment, the polymer devices were fabricated using a "backside" electrodes process.

FIG. 29 illustrates an exploded schematic view of a construction element of an embodiment of a microelectrode array tip. The stencil frame tree 400 is placed on a surface of a carrier wafer including micro-array devices 649 formed therein. The stencil frame tree 400 is suitable aligned with the microarray devices 649 of the carrier wafer 648, and bonded thereof. One or more electronic devices can be suitably placed on the polymer devices either after or before the stencil frame tree 400 is bonded to the carrier wafer 648.

FIG. 30 is a schematic view of another portion of the construction element illustrated in FIG. 29. Once the sacrificial layer has been removed as described above, the devices 649 are released from the carrier wafer 648 and are now bonded to the stencil 640 for support. In the exemplary embodiment, the side of the polymeric device 649 facing the carrier wafer 648 (and in contact with the sacrificial layer) has the microelectrodes at its surface. In general, microelectrodes may be included in either or both sides as described herein.

In some embodiments, a rigid back 642 on the polymer micro-device 649 is required. This renders the device 649 fully, or locally, rigid. This rigidity might be advantageous for insertion into tissue. The concept is a stencil shape 640 which can be bonded onto the devices on the carrier wafer where they have been fabricated. The stencil shape 640 can be implemented in a polymer, such as PEEK or Polyurethane, or in metal such as Medical Grade Stainless Steel or Titanium. It can be molded into shape, cut by machining or laser, or stamped out. When this rigid structure has been attached to the devices, the electronic chip can be bonded. The electronic chip can also be bonded to the devices beforehand. After the assembly process the devices can be removed from the carrier wafer using the same sacrificial etching techniques as described above. A further assembly procedure can be to remove the rigid backing from its frame and integrate the device with its final structure. In some embodiments, the rigid backing is conductive. In other embodiments, the rigid backing is non-conductive. When this support structure is of a conductive material, it can also serve as the electrical ground or reference for the stimulation.

Figure 33C:
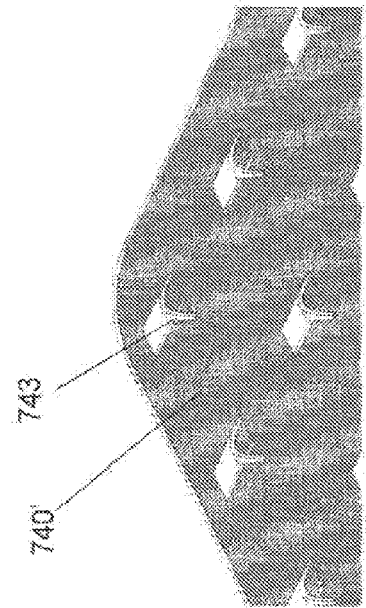
FIG. 33C is a perspective view of a construction element of a microelectrode array assembly shown in FIG. 33B after the rigid backing members have been assembled into position.
Figure 33A:
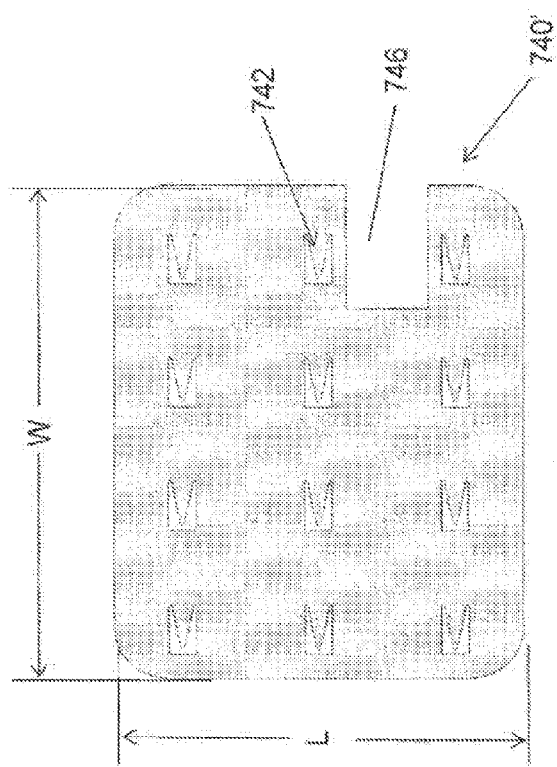
FIG. 33A is a planar view of a construction element of a microelectrode array assembly.

FIG. 33A through FIG. 36C are images of additional embodiments, in which one or more backing layers are used to support a microelectrode film. The one or more backing layers can be rigid, or semi-rigid. In some embodiments, the one or more backing layers can be flexible. FIG. 33A illustrates a planar view of a construction element used to create a rectangular array of microelectrode tips. The exemplary construction element includes a stencil frame tree 740' including an arrangement of, in this example, twelve individual semi-rigid backing members 742. The stencil frame tree 740' can include a rigid material, such as medical grade stainless steel. In some embodiments, the stencil frame tree 740' can be bonded to one or more microelectrode devices, for example, on a carrier wafer.

The stencil frame tree 740' can be implemented by laser cutting, water-jet cutting, chemical etching using photosensitive masks, or another method used to obtain medical-grade, two-dimensional structures. The stencil frame tree 740' can include one or more, open-ended or enclosed, apertures 746, for example, in which microelectronic circuitry can be located.

The stencil frame tree 740' is also characterized by its overall shape and size. Generally, any overall shape is contemplated, including polygons, ellipses, circles, serpentines, irregular shapes, and any combination of such shapes. In the illustrative embodiment, a substantially rectangular stencil frame tree 740' is characterized by its width, W, and its length, L. In the exemplary embodiment, the width is 20 mm, and the length is 15 mm. The stencil frame tree 740' is generally thin to facilitate fabrication and placement within the body. In the exemplary embodiment, the thickness is about 0.1 mm (not shown). Generally, the stencil frame tree 740' has an overall shape and dimensions conforming to the anatomy for which it is meant to be used. Such target anatomies include any of the anatomies described herein, including the brain, the spine, the peripheral nerve system, the cochlea, the retina, and other parts of the body. In some embodiments, it may have a width as wide as 20 cm or greater, and a length as long as 15 cm or greater, although no general limitation as to size and shape are contemplated.

Figure 33B:
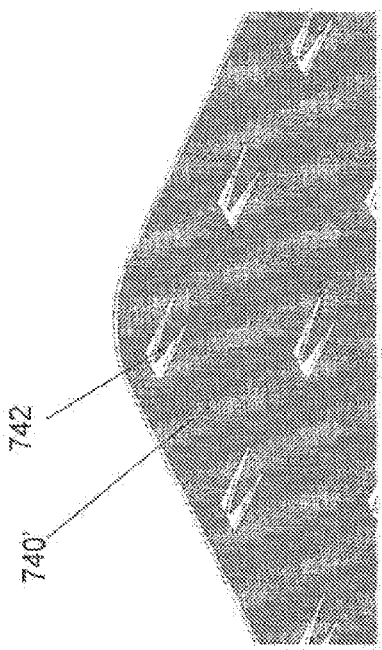
FIG. 33B is a perspective view of a construction element of a microelectrode array assembly.

FIG. 33B is a perspective view of a portion of the stencil frame tree 740, illustrating several semi-rigid backing members 742 formed therein. The general shape semi-rigid backing members 742 can be formed by any suitable means, including pushing, molding, or stamping. Once formed, the semi-rigid backing members 742 can be bent or otherwise formed into a downwards position as shown in FIG. 33C. In other embodiments, the backing members 742 can be bent into an upward position, or into a combination of downward and upward positions. This action results in protruding portions forming a supportive, probe backing member 743. As mentioned in previous embodiments, this bending can be performed before, or after, a microelectrode film has been attached to the stencil frame tree 740'.

Figure 34A:
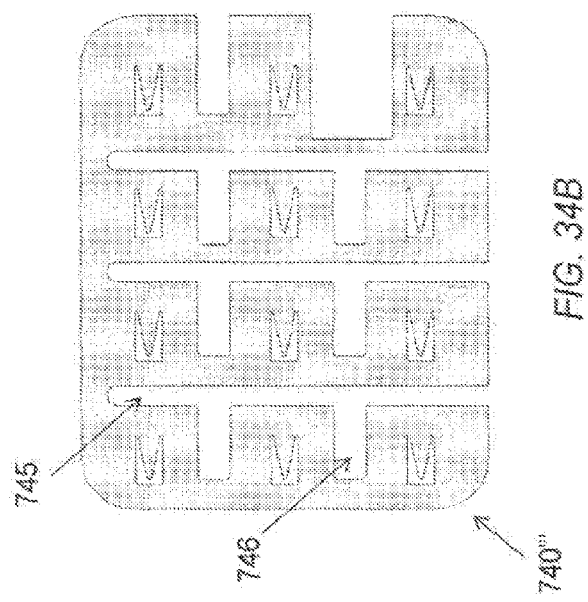
FIG. 34A is a planar view of a construction element of a microelectrode array assembly.
Figure 34B:
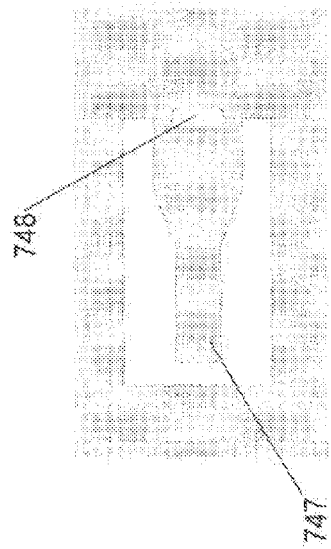
FIG. 34B is a planar view of a construction element of a microelectrode array assembly.

FIG. 34A and FIG. 34B demonstrate additional embodiments of a stencil frame tree 740', 740" (generally 740). In some embodiments, the stencil frame tree 740 can include one or more, vertical elongated grooves or openings 745a through 745c (generally 745) in order to make the stencil frame tree 740 more flexible along one or more axes, enabling a generally planar structure to conform to a portion of anatomy that is not flat, as shown in FIG. 34A. In some embodiments, the stencil frame tree 740 can include one or more, horizontal 746 or vertical elongated grooves or openings 745, in order to make it more flexible along several axes, enabling it to conform to a portion of anatomy which is not flat, as shown in FIG. 34B.

Figure 34C:
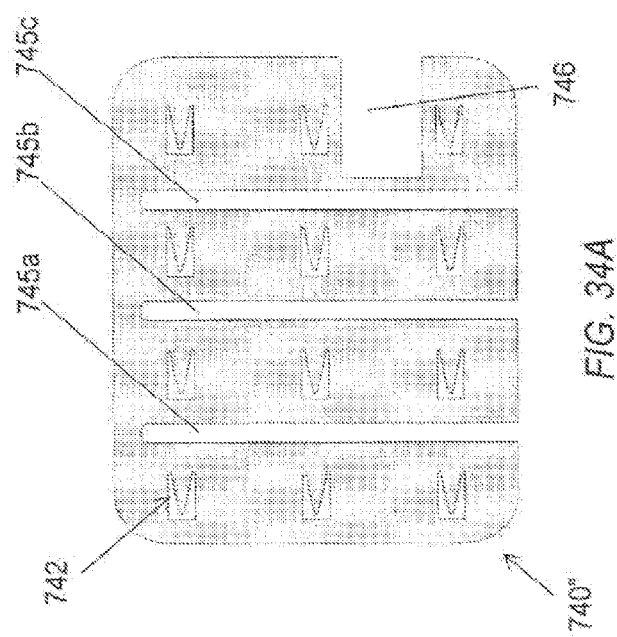
FIG. 34C is a more detailed planar view of a construction element of a microelectrode array assembly.
Figure 34D:
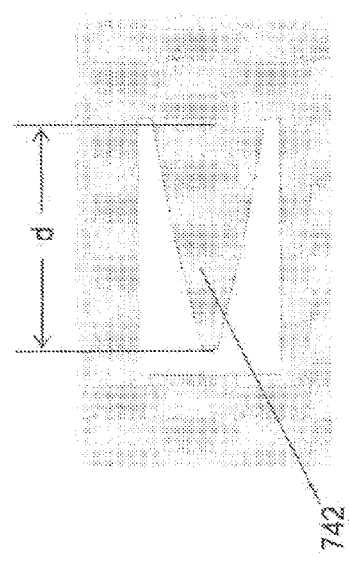
FIG. 34D is a more detailed planar view of an alternative embodiment of a construction element of a microelectrode array assembly.

FIG. 34C and FIG. 34D demonstrate various embodiments of semi-rigid backing members 742, illustrating different shapes and features. FIG. 34C demonstrates a closer view of the embodiment discussed above, characterized by a relatively sharp tip which can promote easier penetration of tissue, including the dura mater on the surface of the brain. The rigid members 742, 747 are also characterized by their respective length d measured from a base portion to the tip, that can be implemented to be short, or long enough to reach certain area of anatomy. In some embodiments, one or more of the semi-rigid backing members 742, 747 of the same stencil frame tree 740 can have different dimensions and/or different shapes. In some embodiments, e.g., for cranial applications, the length d is generally about 1-4 mm but can be as short as 0.5 mm or less, or as long as several centimeters or greater.

FIG. 34D illustrates an additional embodiment, characterized by a rounded tip which can prevent chronic injury of tissue after implantation. The rigid member 747 also differs by an aperture, or gap in its base 748 which can improve the ease of bending the member into is final, protruding position. Such a gap 748 can be included in any of the embodiments described herein.

Figure 35B:
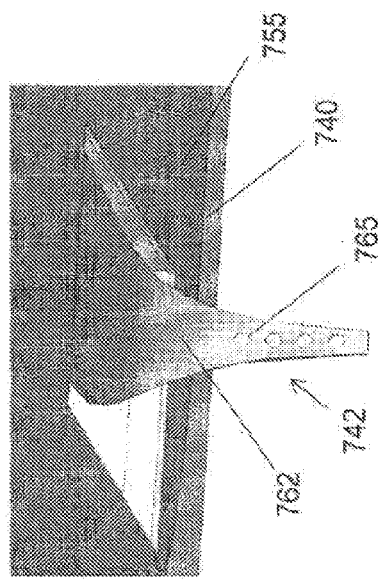
FIG. 35B is a more detailed perspective view of a microelectrode array tip.
Figure 35D:
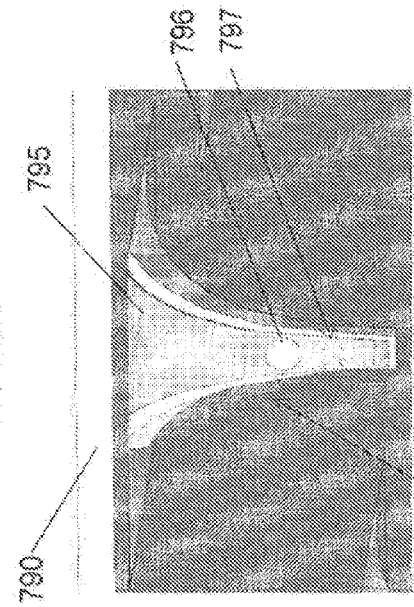
FIG. 35D is a more detailed perspective view of an alternative embodiment of a microelectrode array tip.
Figure 35A:
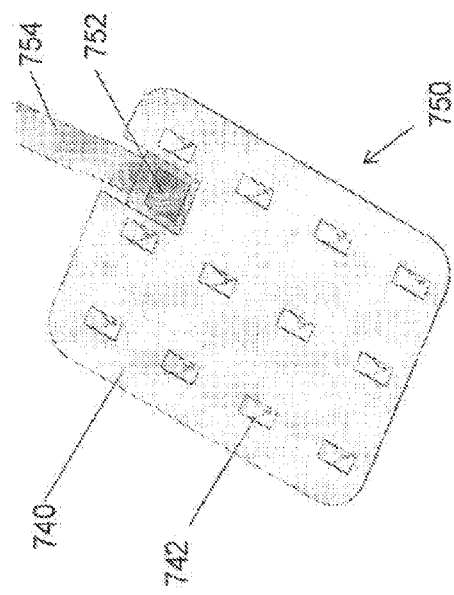
FIG. 35A is a perspective view of a microelectrode array assembly.

FIG. 35A illustrates a top perspective view of an assembled microelectrode assembly 740 that can be used for recording and/or stimulation. In this assembly the rigid stencil frame tree 740' is supporting a microelectrode film 755 (not shown) on its inferior side. Semi-rigid backing members 742 have been bent downwards to protrude from its inferior side. A microelectronic circuit element 752 is electrically coupled between the microelectrode film and an external device (not shown) through flexible electric conduit member 754.

FIG. 35B illustrates in more detail a perspective view of a single rigid backing member 742 from the inferior side of the assembly 750. The microelectrode film 755 is visible, having been bonded to the inferior side. On the inferior side of the microelectrode film 755 are an arrangement of microelectrode elements 765. The microelectrode film 755 and microelectrode elements 765 conform to the bent rigid backing member 742, extending away from the plane of the stencil frame tree 740'. On the surface of the exemplary embodiment are four microelectrode elements or sites 765. These sites can also be used for one or more of sensing or recording neural activity, or electrical stimulation, or they can be enabled to stimulate and record from the same site. The number of microelectrode sites 765 of each bent rigid backing member 742 can vary from one or more. In this exemplary embodiment there are four microelectrode stimulation sites 765. They can also be arranged in other configurations, including any of the configuration described herein, such as a tetrode configuration as will be shown in subsequent embodiments, such as in FIG. 42A through FIG. 42D and FIG. 43F through FIG. 43G.

Figure 35C:
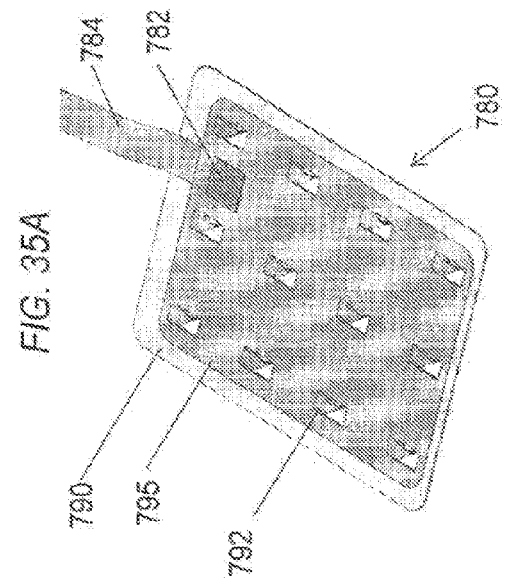
FIG. 35C is a perspective view of an alternative embodiment of microelectrode array assembly.

FIG. 35C illustrates a perspective view of an assembled microelectrode recording and stimulation device 780. In this assembly the rigid stencil frame tree 790 is supporting a microelectrode film 795 on its inferior side. Semi-rigid backing members 792 have been bent downwards to protrude from its inferior side. A microelectronic circuit element 782 brings the microelectrode film into electrical contact with an external device (not shown) through flexible electric conduit member 784.

FIG. 35D illustrates a closer perspective view of a single rigid backing member 792 from the inferior side of the assembly 780. The microelectrode film 795 has been bonded to the superior side of the rigid stencil frame tree 790. The microelectrode film 795 can be implemented using the micro-fabrication processes described herein, and can be bonded to the rigid stencil frame tree 790 by gluing or heating. On the superior side of the microelectrode film 795 are microelectrode elements 796 and 797 which conform to the bent rigid backing member 792. On the surface is a relatively large microelectrode stimulation site 796 for stimulating neural activity. Additionally, on the surface is an arrangement of four relatively small microelectrode recording sites 797 arranged in a tetrode configuration used for single neural cell recording. The number of microelectrode stimulation sites 796 on each rigid backing member 792 can vary from one or more. There are further tetrode configuration as will be shown in subsequent embodiments, such as in FIG. 42A through FIG. 42D and FIG. 43F through FIG. 43G.

Figure 35E:
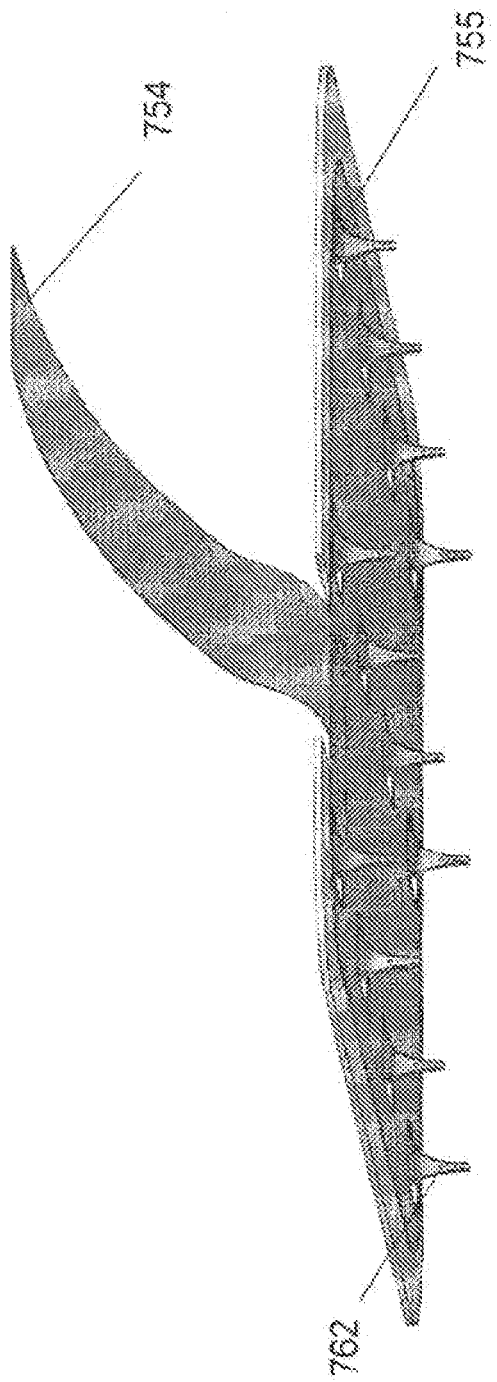
FIG. 35E is a perspective view of the microelectrode array assembly shown in FIG. 35A.

FIG. 35E illustrates a perspective view of the array of protruding microelectrode elements 762 shown in FIG. 35A. The microelectrode film 755 can be implement using any of the microfabrication procedures previously described. In this exemplary embodiment, the backside fabrication process was used. The microelectrode film 755 can be bonded to the stencil tree frame through gluing or heating.

As shown in FIG. 34A and FIG. 34B, it may be necessary to include elongated gaps in the rigid backing frame 740 and the bonded microelectrode film 755 in order for the microelectrode assembly 750 to conform to a portion of anatomy. FIG. 36A shows a portion of human anatomy, the left hemisphere of the brain 771. On its cortical surface, an exemplary microelectrode assembly 750 has been placed, which can be used to record and/or stimulate neural activity.

Figure 36B:
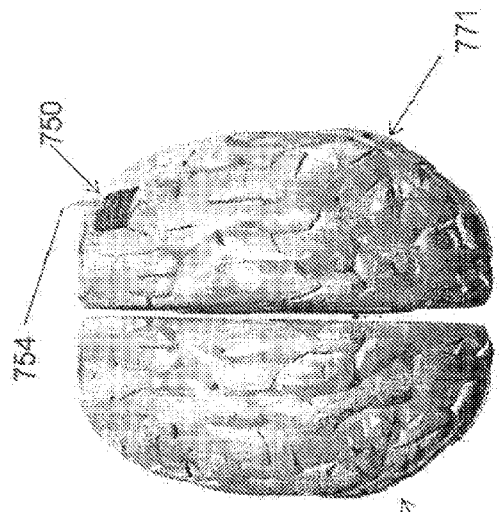
FIG. 36B is an additional view of a portion of a human anatomy illustrating an exemplary microelectrode structure positioned at a neurological target.

FIG. 36B illustrates an additional perspective demonstrating both the left hemisphere 771 and the right hemisphere 772 of the brain. The microelectrode assembly 750 has been surgical placed on the cortex, and connected to a separate control system (not shown) through electrical conduit 754. The separate control system can be located within the body, external to the body, or a combination of internal and external. The device is generally placed by creating a craniotomy. The protruding rigid members 742 can puncture the dura mater (not shown) therefore not requiring its surgical removal. Alternatively or in addition, a surgeon will remove the dura mater, and the protruding members 742 will puncture the cortex with a depth that is determined by the length of the protruding member 742.

Figure 36C:
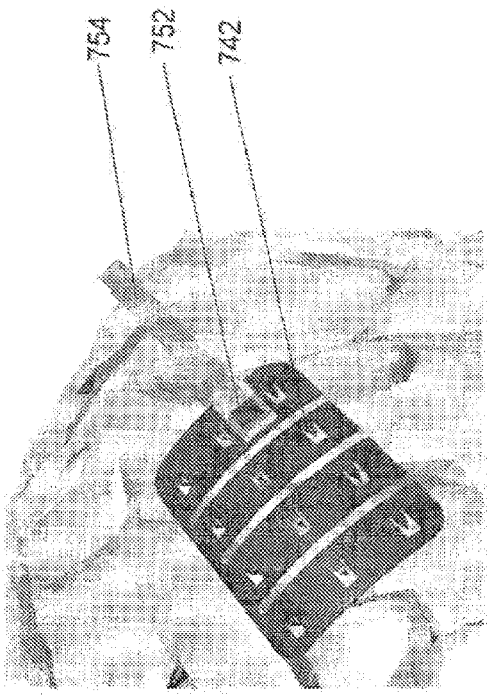
FIG. 36C is a more detailed view of a portion of a human anatomy illustrating an exemplary microelectrode structure positioned at a neurological target.
Figure 36A:
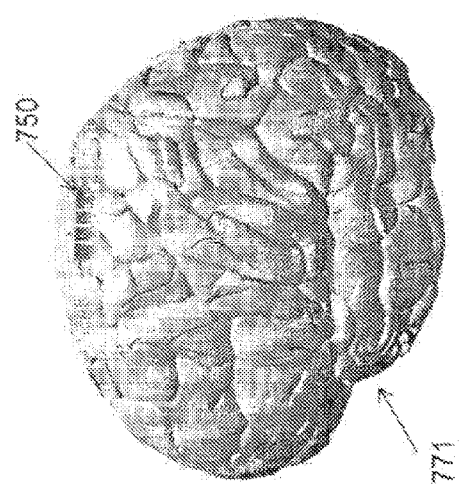
FIG. 36A is a view of a portion of a human anatomy illustrating an exemplary microelectrode structure positioned at a neurological target.

This is demonstrated in more detail in FIG. 36C, in which an array of 12 protruding members 742 have been inserted into the first layers of the cortex. A microelectrode element 752, when included, can be used to record, stimulate, or both record and stimulate neural activity on each of the microelectrode sites that have been implemented on each of the protruding members 742. In some embodiments, one or more of the protruding members 742 can be actuated independently or in one or more groupings to record and/or stimulate a desired region addressable by the device 250. In general, the microelectrode assembly 750 can be configured with any of microelectrode probe described herein, and used in combination with any of the stimulation and/or recording or sensing devices described herein.

Electronic Components

The electronic components of the device enable: (i) recording of neural activity from the microelectrode array to identify which microelectrode sites are closest to the stimulation region of interest; and (ii) stimulation and modulation of neuronal activity with the microelectrode array and the ability to select which microelectrode sites stimulating.

The electronics can be implemented using discrete components, integrated circuit technology, or a combination of both. A black box design of the electronics is shown below. The electronics can be driven by an existing Implantable Pulse Generator (IPG), but will include a telemetric programming interface to properly condition or route the signal from the IPG to the microelectrode array. An embodiment of the electronic components exists which does not require the IPG.

Mechanical Components

The mechanical components and associated assembly processes serve to house the device in a hermetic and biocompatible manner. They also enable connection to an existing Implantable Pulse Generator or the extra-corporeal control unit. The extra-corporeal unit provides power, programming ability and retrieval of information. It can be implanted much like the external cochlear stimulation systems that exist today. In an embodiment that includes an Implantable Pulse Generator, it would serve to retrieve information and program the electrical unit to route the signals from the IPG to the microelectrode array.

Figure 37:
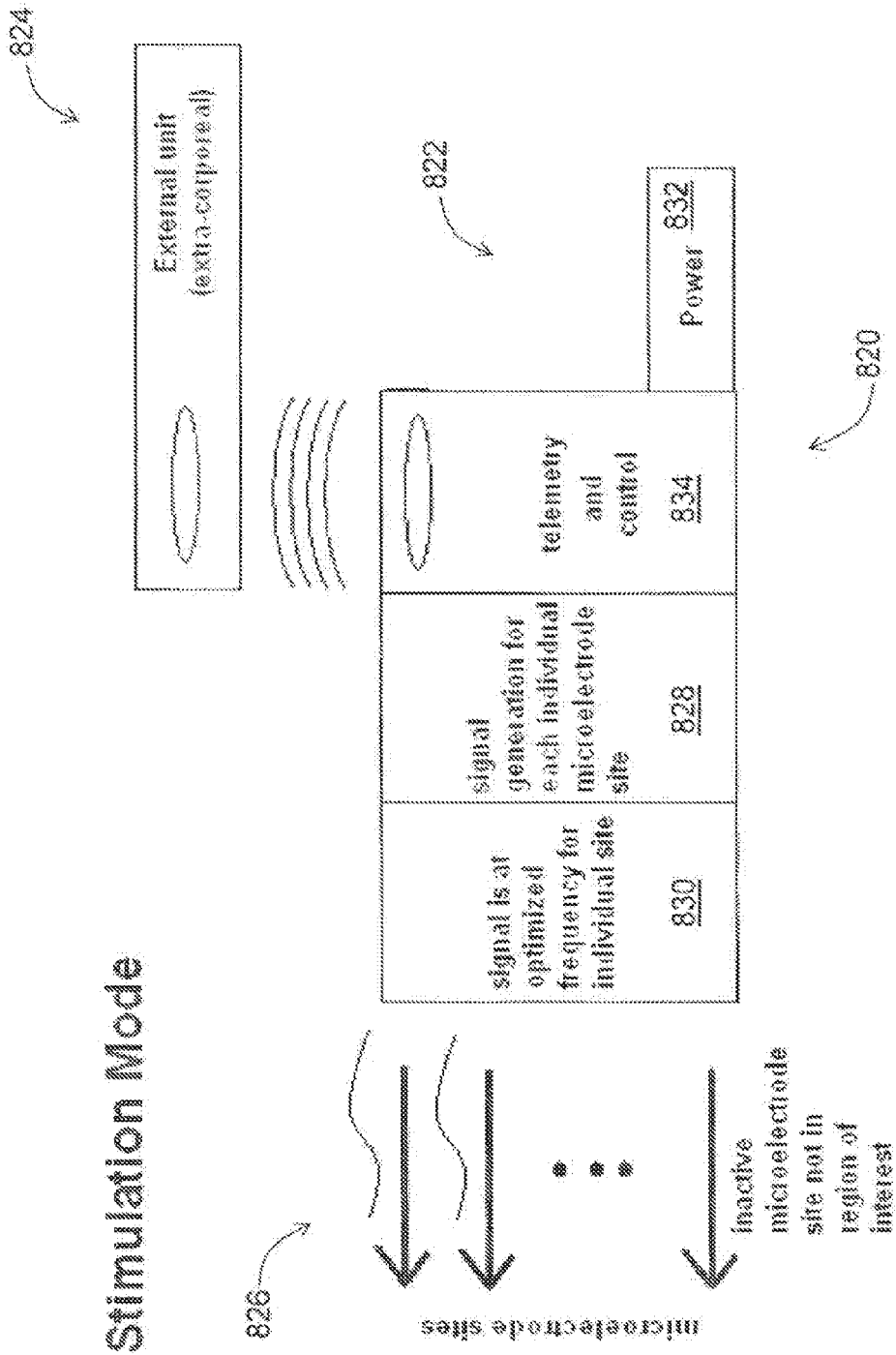
FIG. 37 is a functional block diagram of an exemplary embodiment of a neurological microelectrode system configured in stimulation mode.
Figure 38:
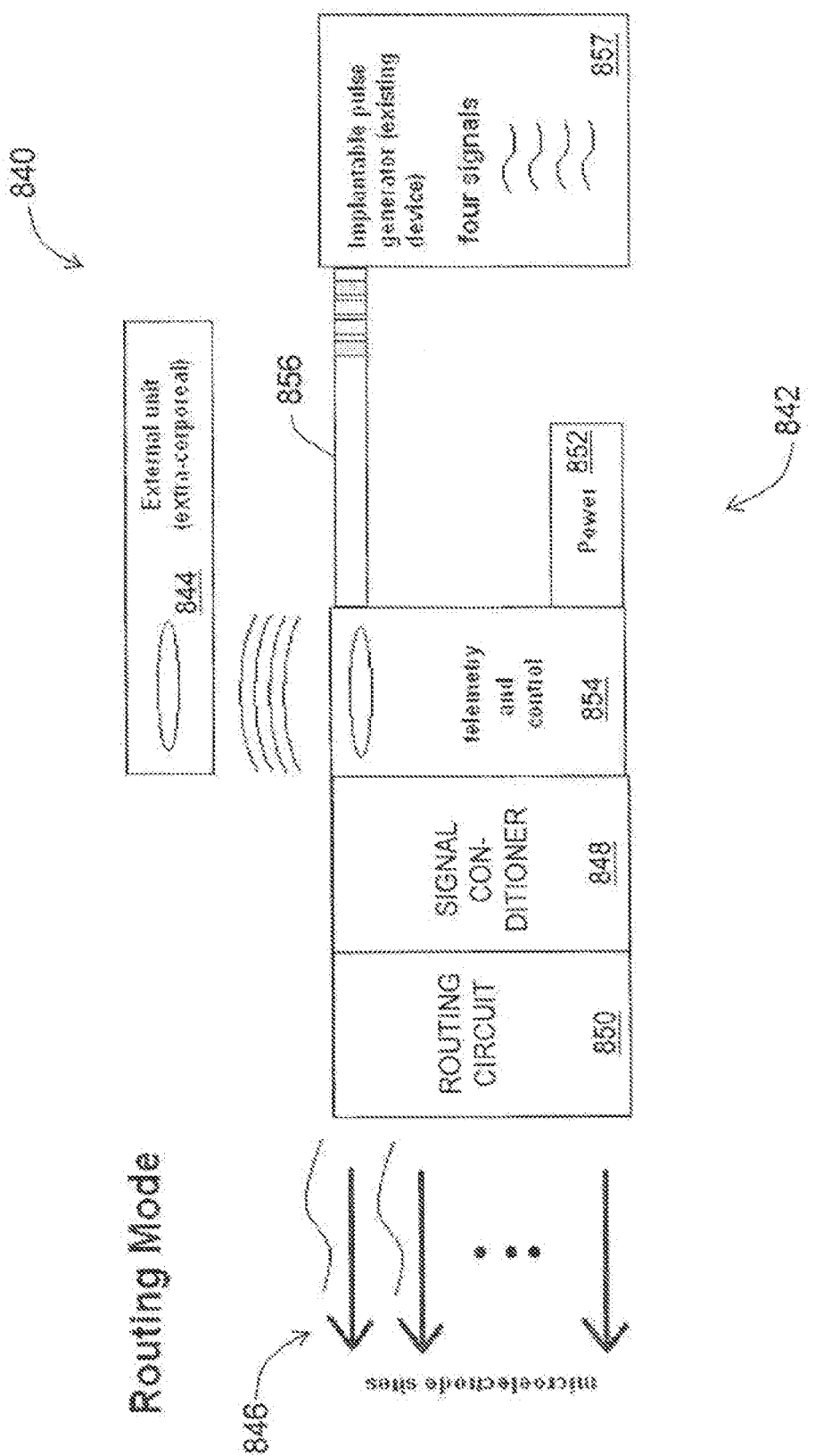
FIG. 38 is a functional block diagram of an exemplary embodiment of a neurological microelectrode system configured in routing mode.

Referring to FIG. 37, a functional block diagram of an exemplary embodiment of a neurological target stimulator 820 configured in a stimulation mode. The stimulator 820 includes an implantable portion 822 including a microelectrode array 826 positionable at a neurological target. The implantable portion 822 also includes a signal generation device 828 for actively stimulating the neurological target. In some embodiments, each of the one or more microelectrodes of the microelectrode array 826 is in communication with a dedicated signal generation device 828. The respective stimulation signal provided at an optimized frequency for each individual microelectrode-tissue interface, based on a peak resistance frequency. The implantable portion 822 can include a power source 832, such as a battery. In some embodiments, the implantable portion 822 also includes a telemetry and control module 834 configured for external communication with an extra-corporeal unit 824. Such a feature can be used to provide extra-corporeal control for operating the implantable portion 822.

Referring to FIG. 37, a functional block diagram of another exemplary embodiment of a neurological target stimulator 840 is illustrated configured in so-called routing mode. The stimulator 840 includes an implantable portion 842 including a microelectrode array 846 positionable at a neurological target. The implantable portion 842 also includes a signal routing circuit 850 configured to direct a stimulation signal to one or more of the microelectrodes 846 for actively stimulating the neurological target. In this embodiment, the stimulation signal is obtained from a separate, implantable pulse generator 857. The pulse generator 857 is in communication with the implantable portion 842 through an interconnection cable 856 containing one or more signal beads. The implantable portion 842 also includes at least one signal conditioner 848 configured to condition an output signal from the pulse generator 857 suitable for stimulation of the neurological target through one or more of the microelectrodes 846. The implantable portion 232 generally includes a power source 852, such as a battery. In some embodiments, the implantable portion 842 also includes a telemetry and control module 854 configured to communicate with an extra-corporeal unit 844, to provide controls for operating the implantable portion 842.

Filtering of an Existing Signal

In some embodiments, the signal conditioner 848 include a filtering circuit to pre-filter or gain adjust (e.g., pre-amplify and/or attenuate) or otherwise condition an existing signal before routing it to a microelectrode array. Several popular filter options include digital filters, such as infinite impulse response (IIR) filters, electronic filters using one or more electrical components, such as inductors and capacitors, and surface acoustic wave (SAW) devices. The filters can be designed through well known filter synthesis techniques to have a preferred performance features. Some of the controllable features in filter synthesis include filtration bandwidth, corner frequency, pass-band ripple, and relative sideband level. Such filters include categories referred to as Butterworth, Chebyshev 1 and 2, and Elliptic filters. The particular implementation—whether analog or digital, passive or active, makes little difference as the output from any implementation would still match the desired output.

Figure 39:
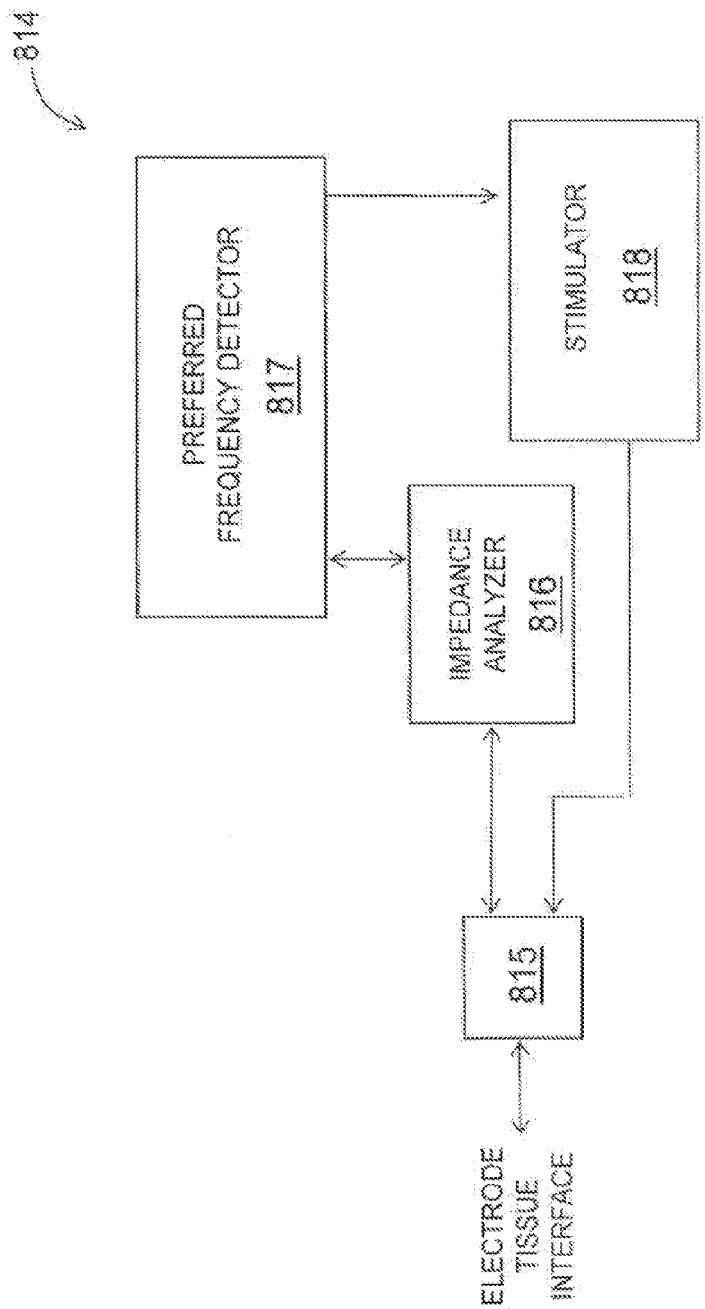
FIG. 39 is a functional block diagram of another embodiment of a neurological microelectrode system.

FIG. 39 is a functional block diagram of another embodiment of a neurological microelectrode target stimulator 814 is shown. The stimulator 814 includes a microelectrode array 815 positionable at a neurological target of interest. The stimulator 814 also includes an impedance analyzer 816 configured for measuring an electrical impedance, a preferred frequency detector 817, and a stimulator 818 for electrically stimulating the neurological target.

The impedance analyzer 816 can use any of various known techniques for measuring electrical impedance. Generally, the impedance analyzer 816 provides a test electrical signal having known or measurable attributes to the microelectrode-tissue interface. Such attributes include a voltage level of a voltage source, or a current level of a current source. The test voltage or current, as the case may be, when applied to the microelectrode-tissue interface, includes a sensed current or voltage according to physical properties of the microelectrode-tissue interface. The impedance analyzer 816 can form a ratio of the test signal to the sensed signal, yielding an impedance value according to Ohm's Law: $Z=V/I$. As the microelectrode-tissue impedance Z is a complex quantity, each of the test and sensed electrical signals is identified as having both a magnitude and a phase.

In operation, the impedance analyzer measures a complex impedance of the microelectrode-tissue interface surrounding the at least one microelectrode 815. The impedance analyzer repeats the measurements at multiple different frequencies, by varying frequency of the applied test electrical signal. Preferably, the multiple frequencies span a frequency range that includes a biologically relevant frequencies. The preferred frequency detector 817 identifies the measured impedance being closest to a pure resistance. Such a determination can be accomplished by identifying the measured impedance value having a phase value closest to zero. For example, a measured impedance can be identified having minimum absolute value phase (i.e., $MIN|\angle Z|$). Such a determination can also be accomplished by identifying the measured impedance value having a minimum reactance (i.e., $MIN(Im\{Z\})$). The frequency at which the impedance determined to be closest to a pure resistance is identified as a preferred stimulation frequency. The stimulator 818 is then adjusted to provide a stimulation signal at a frequency, or frequency band, at or near the preferred stimulation frequency. The stimulation signal is then applied to the microelectrode array 815.

Figure 40:
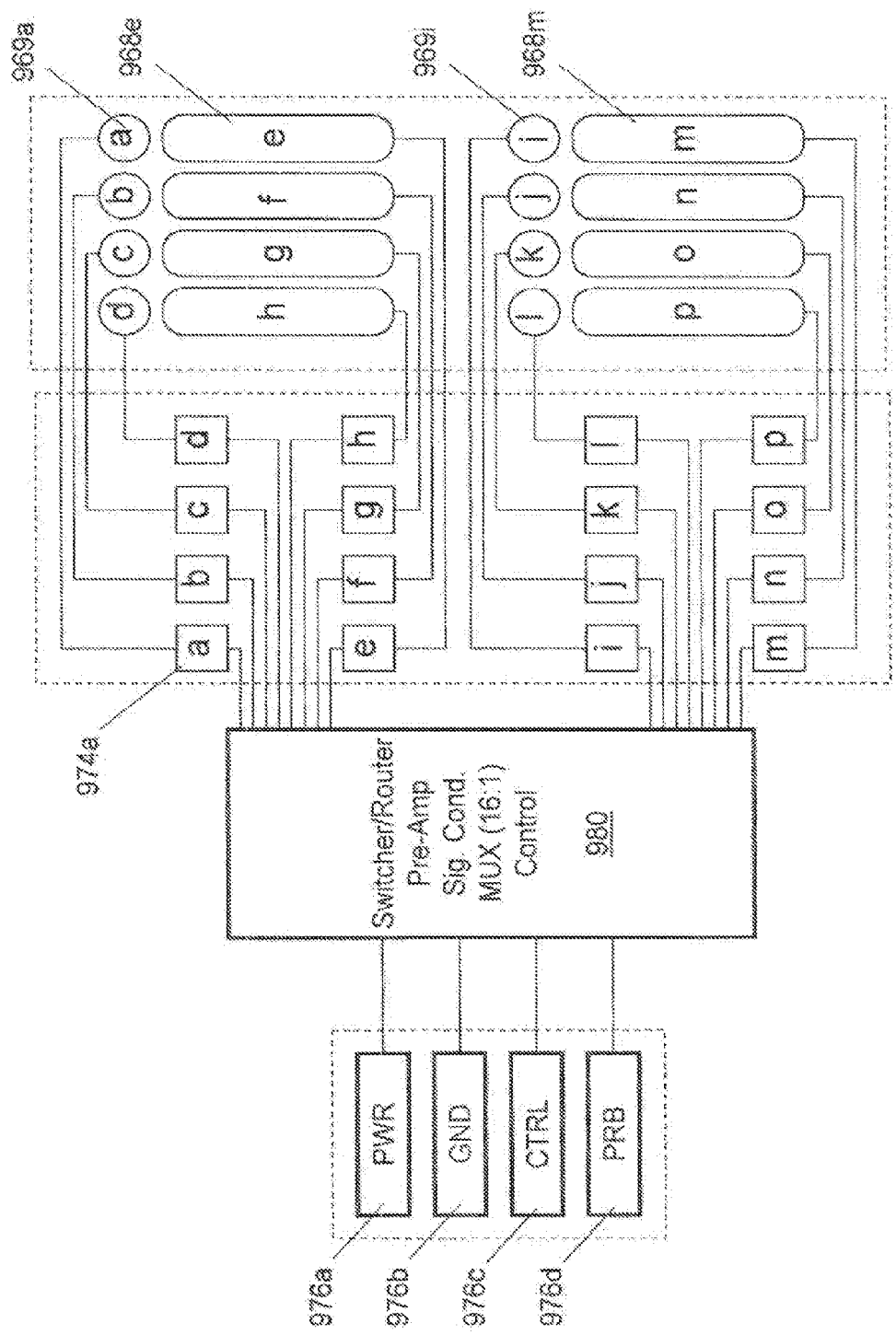
FIG. 40 is an electronic circuit schematic diagram for an exemplary on board microelectronic circuit.

Illustrated in FIG. 40 is an electronic circuit schematic diagram for an exemplary on board ASIC as shown in the embodiments above. Shown along the right hand portion of the schematic diagram are eight stimulation electrode elements 968a through 868h (generally 968) which are generally spread between several cortical depth probes. Each one of these elements 968 is in electrical communication with a respective electronic device contact 974a through 974d and 974m through 974p (generally 974). Also illustrated along the right hand portion of the schematic diagram are eight recording electrode elements 969a through 969h (generally 969). Similarly, the recording contacts are spread between several cortical depth electrodes. Similarly, each of the recording electrode elements 970 is in electrical communication with a respective electronic device contact 974e through 974h and 974j through 974l. For illustrative purposes, the schematic diagram includes a representative electronic device 980. For brevity, the schematic diagram includes only eight recording and eight stimulation contacts but a full schematic diagram for many more contacts is similar. Additionally, or alternatively, some embodiments will only include recording electrodes. The electronic device may include one or more of a switch or router, a preamplifier, a signal conditioner, a multiplexer, and a controller. The electronic device 980 is in electrical communication with all sixteen of the electronic device contact elements 974a through 974p.

The electronic device 980 is in further communication with wire lead contacts 976a through 976d (generally 976) that are embedded in the exemplary ribbon cable tether. In the illustrative example, the first wire lead contact 976a is used for supplying electrical power to the microelectronic device and/or one or more of the stimulation electrode elements 968. The second wire lead contact 976b is used to provide an electrical ground contact. This ground contact 976b may include earth ground, another electrical ground within the system, such as a chassis ground of a medical device connected to the electronic device 980, or simply a signal return line. A third wire lead contact 976e corresponds to a control signal that may be used to provide control inputs from an operator or other medical device, to control configuration and/or operation of the electronic device 980. Alternatively or in addition, the control signal contact 976c may be used for control signals from the electronic device 980 to another medical device. A fourth wire lead contact 976d corresponds to a signal contact as may be used for directing electrical activity detected by one or more of the recording electrode elements 969 to a recording or display device. Alternatively or in addition, the signal contact 976d may be used for directing electrical stimulation signals from another medical device to one or more of the stimulation electrode elements 968.

A top view of an exemplary embodiment of a microelectrode assembly 920 is illustrated in FIG. 41A. The assembly 920 includes an array of microelectrodes 922 positioned along a distal end of an elongated probe substrate 924. A first electronic assembly 928 is positioned at a proximal end of the elongated probe substrate 924. The first electronic assembly 928 can include one or more integrated circuit elements 921, such as a microprocessor, and one or more discrete electronic components 932. The first electronic assembly 928 is interconnected to each of the microelectrodes 922 through a respective trace 926 running along the elongated probe substrate 924. The electronic assembly 928 and can be configured to implement one or more functions of the implantable neurological stimulator described herein. In some embodiments, the elongated probe substrate also includes at least a portion of the electronic assembly 928.

In some embodiments, the first electronic circuitry 928 is connected to an implanted pulse generator (not shown) through a cable 924. In some embodiments, as shown, a second electronics assembly (or a portion of the first electronics assembly) includes telemetry circuitry 939, such as a telemetry antenna. In the exemplary embodiment, at least a portion of electronic circuitry 928, 938 is positioned adjacent to the microelectrodes 922, for example being joined by the elongated probe substrate 924.

The mechanical components and associated assembly processes serve to house the assembly 920 in a hermetic and biocompatible manner. They may also enable connection to an existing Implantable Pulse Generator or the extra-corporeal control unit. The extra-corporeal unit can provide power, programming ability, and retrieval of information. In some embodiments, the assembly 920 can be implanted much like currently available external cochlear stimulation systems. In an embodiment that includes an implantable pulse generator, it would serve to retrieve information and program the electrical unit to route the signals from the implantable pulse generator to the microelectrode array 922.

The device provides highly localized and efficient stimulation by incorporating microfabricated components, electronic components and mechanical components. The microfabricated component consists of a microelectrode array. This array can be implemented in a polymeric material such as polyimide, polyurethane, parylene, or polysiloxane (silicone) and includes thin film or plated layers of a metal or metal oxide with high charge transfer capability such as platinum, platinum-iridium, iridium, iridium oxide or titanium. The polymeric and metallic layers can be deposited sequentially and formed using established principles of microfabrication such as spin coating, DC/RF sputtering, photolithography, plasma etching, and etching with a mask consisting of a secondary or sacrificial material such as silicon dioxide or photosensitive resist. The metallic layer can be formed to create the microelectrode arrays and traces which connect the array to the electronics and housing. The polymeric layers serve to isolate the traces from each other but also provide the structure of the implant's stimulating/recording tip. There are several fabrication methods which can be described to build such a microfabricated component.

The electronic or microelectronic components of the device enable: (i) the ability to identify the peak resistance frequency for each individual microelectrode site using electrical impedance spectroscopy; (ii) stimulate at the characteristic peak resistance frequency of each microelectrode (this guarantees minimized signal distortion and maximum charge transfer to the tissue); and (iii) stimulation and modulation of neuronal activity with the microelectrode array and the ability to select which microelectrode sites are stimulating.

The electronics can be implemented using discrete components, integrated circuit technology, digital signal processing (DSP), or a combination of all three. The electronics can be incorporated in one unit, or can be used in conjunction with an existing implantable pulse generator (IPG). The electronics may include a telemetric programming interface to properly condition or route the signal from the IPG to the microelectrode array.

Referring to FIG. 41B, a side view of an exemplary alternative embodiment of a microelectrode structure is illustrated. In this embodiment, an electronics assembly 956 is positioned remote from the microelectrode array 952. The microelectrode array 952 is joined to the electronics assembly 956 through an arrangement of interconnecting electrical leads 954. The electronics assembly 956 can be configured to implement one or more function of the implantable neurological stimulator described herein. As illustrated, the electronics assembly 956 can also be connected to an implanted pulse generator (not shown) through an interconnecting cable 960. Alternatively or in addition, the electronics assembly 956 can include telemetry circuitry for communicating with an external telemetry device 962.

The electronics assembly can include an electrical grounding lead for interconnection to an electrical ground potential 958. In any of the embodiments described herein, impedance measurements and/or stimulation can be implemented between two or more microelectrodes (e.g., adjacent microelectrodes). Alternatively or in addition, impedance measurements and/or stimulation can be implemented between one or more microelectrodes and an electrical ground reference.

Note that a device can be assembled to not include electronics. This device would then transfer the signal from the Implantable Pulse Generator directly to the electrodes. A device with electronics would first "pre-filter" the signal before applying to the electronics. This "pre-filter" might take the form of signal filtering in order to achieve a certain signal spectrum, multiplexing and routing in order to direct signals from a pulse generator to a choice of microelectrode sites. The following figures demonstrate the different components and embodiments.

Cortical Depth Probe Embodiments

Various exemplary embodiments of microelectrode array element configuration including tetrode arrangements are illustrated in FIG. 42A through FIG. 42D. Referring to FIG. 42A, a microelectrode array element 1000 includes a stimulation electrode 1002 and four recording electrodes 1004. In the exemplary embodiment, the stimulation electrode 1002 is disc-shaped; however, other shapes are anticipated, such as polygons, ovals, and irregular shapes. In this embodiment, the recording electrodes 1004 are substantially smaller than the stimulation electrode 1002, and positioned within the outer perimeter of the stimulation electrode 1002. In order to accommodate this arrangement, the stimulation electrode includes a respective open area 1006, one for each of the recording electrodes. In the exemplary embodiment, the recording electrodes 1004 are uniformly spaced having about 90° angular separation between adjacent pairs.

In general, the open areas 1006 can have any shape, and the shape need not be the same as the shape of any recording electrode 1004 that may be positioned therein. In the exemplary embodiments, the open areas 1006 do have a similar shape, namely a circle, as the disc-shaped recording electrodes 1004. The openings are dimensioned larger than the recording electrodes 1004, such that the recording electrodes can be placed within the open areas 1006, without touching the stimulation electrode 1002. An annular region of separation exists between the two electrodes 1002, 1004. The recording electrodes 1004 may each be similarly shaped and/or similarly sized with respect to each other. They may have similar shape as the stimulation electrode 1002, or have a different shape. In some embodiments, at least some of the recording electrodes 1004 have different shapes and/or different sizes with respect to each other.

In the exemplary embodiment, the four disc electrodes 1004 embedded within the larger, stimulation electrode 1002. The recording electrodes 1004 each have a respective diameter of about 50 μm, and a relative separation to their nearest neighbors of about 150 μm. The stimulation device has a diameter of 300 μm. In some embodiments, the diameter of each recording electrode can range between about 2 μm or less, and about 300 μm or more. In some embodiments, the diameter of the stimulation electrode can range between about 5 μm or less, and about 1,000 μm or more.

Referring to FIG. 42B, an alternative embodiment of a microelectrode array element 1010 shows a stimulation electrode 1012 as a non-closed disc. The outer perimeter of the stimulation electrode 1012 generally follows a circular arc, with indentations defining open areas 1016 extending in from the perimeter, towards the center of the electrode 1012. In particular, four such open area 1016, or slots, each accommodate a respective recording electrode 1014. The recording electrode 1014 is positioned toward an inner end of the open area 1016, nearest the center of the stimulation electrode 1012. In at least some embodiments, the recording electrode 1014 does not touch the stimulation electrode 1012. In some embodiments, the perimeter of the stimulation electrode 1012 are generally rounded, without sharp corners, in order to prevent highly localized fields. Although a four-recording electrode embodiment is shown, other embodiments are possible including one or more recording electrodes positioned within respective open areas 1016. Although circular shapes are illustrated for each of the stimulation electrode and the recording electrode, different shapes can be used. The shapes can be regular, such as ellipses, polygons, and irregular shapes.

Referring to FIG. 42C, illustrates a similar embodiment of a microelectrode array element 1020 to that described above, except that two tetrodes 1024a, and 1024b are embedded within the same stimulation electrode 1022. The two tetrodes 1024a, 1024b can record neural activity from different tissue volumes sizes, with different sensitivities to neural activity. The "inner tetrode" 1024b can have the same, or different microelectrode diameters than the "outer tetrode" 1024a. The diagram shows an "inner tetrode" with 50 μm discs, and an "outer tetrode" with 60 μm discs. Other shapes, sizes, and numbers of tetrode elements are possible.

Referring to another microelectrode element embodiment 1030 illustrated in FIG. 42D, a tetrode 1034 is only slightly embedded into the stimulation electrode 1032. As shown, the innermost portion of the open area 1036 is spaced apart from an outer perimeter of the stimulation electrode 1032 by a distance less than a diameter of the recording element 1034. Such a configuration would allow adjustment and optimization of the sensitivity and volume of tissue being recorded.

Various embodiments of neurological stimulation devices and techniques have been described herein. These embodiments are given by way of example and are not intended to limit the scope of the present disclosure. It should be appreciated, moreover, that the various features of the embodiments that have been described may be combined in various ways to produce numerous additional embodiments.

One or more of any of the microelectrode array elements 1000, 1010, 1020, 1030 can be positioned on an elongated planar member, or a cortical depth probe, forming a microelectrode array film that is one component of a neurological surface probe. The neurological surface probes described above were composed of at least one cortical depth probe. In most embodiments the cortical depth probe protrudes from a planar surface of the neurological surface probe. It is understood that the following embodiments, i.e., FIG. 43A through FIG. 43J, of cortical depth probes, can each be used and implemented in the embodiments of neurological surface probes presented herein.

A series of exemplary cortical depth probes are illustrated in FIG. 43A through FIG. 43J. An exemplary cortical depth probe 1040 is illustrated in FIG. 43A. The cortical depth probe 1040 includes four microelectrode elements 1045. Each of the microelectrode elements 1045 can be used as stimulation or recording electrodes, or combined stimulation-recording electrodes. In the present embodiment microelectrode elements 1045 are implemented with a diameter of 300 um and are spaced by 1 mm. In the illustrative embodiment, the microelectrode elements 1045 are discoid and are spaced apart from each other in a manner to cover a wide linear depth in the cortical region.

A series of exemplary cortical depth probes are illustrated in FIG. 43A through FIG. 43J. An exemplary cortical depth probe 1040 is illustrated in FIG. 43A. The cortical depth probe 1040 includes four microelectrode elements 1045. Each of the microelectrode elements 1045 can be used as stimulation or recording electrodes, or combined stimulation-recording electrodes. In the present embodiment microelectrode elements 1045 are implemented with a diameter of 300 μm and are spaced by 1 mm. In the illustrative embodiment, the microelectrode elements 1045 are discoid and are spaced apart from each other in a manner to cover a wide linear depth in the cortical region.

An additional cortical depth probe 1050 is illustrated in FIG. 43B. The cortical depth probe 1050 includes three microelectrode elements 1055. Each of the microelectrode elements 1055 can be used as stimulation or recording electrodes, or combined stimulation-recording electrodes. In the present embodiment microelectrode elements 1055 are implemented with a diameter of 400 μm are and spaced by 1.5 mm. In the illustrative embodiment, the microelectrode elements 1055 are discoid and are spaced apart from each other in a manner to cover a wide linear depth in the cortical region.

An additional cortical depth probe 1060 is illustrated in FIG. 43C. The cortical depth probe 1060 includes two small diameter microelectrode elements 1065 and two large diameter microelectrode elements 1066. Each of the microelectrode elements 1065 and 1066 can be used as stimulation or recording electrodes, or combined stimulation-recording electrodes. However, in the present embodiment it may be preferable to use the small diameter microelectrode elements 1065 as recording electrodes because they are smaller in diameter and may capture more single-unit cellular activity. Additionally, it may be preferable to use the large diameter microelectrode elements 1066 as stimulation electrodes because they are larger in diameter and can transfer more charge to the neural tissue increasing the efficacy of stimulation. In the present embodiment, small diameter microelectrode elements 1065 are implemented with a diameter of 300 μm, and large diameter microelectrode elements 1066 are implemented with a diameter of 700 μm. The microelectrode elements 1065 and 1066 are spaced by 1.2 mm. In the illustrative embodiment, the microelectrode elements 1065 and 1066 are discoid and are spaced apart from each other in a manner to cover a wide linear depth in the cortical region.

Another alternative embodiment of a cortical depth probe 1070 is illustrated in FIG. 43D. In this embodiment, each of the cortical depth probes 1070 include at least one elongated microelectrode elements 1075. Each of the elongated microelectrode elements 1075 can be used as stimulation or recording electrodes, or combined stimulation-recording electrodes. In the illustrative embodiment, the elongated microelectrode elements 1075 are rounded-corner rectangular and are spaced apart from each other in a manner to cover a wide linear depth in the cortical region.

Another alternative embodiment of a cortical depth probe 1080 is illustrated in FIG. 43E. In this embodiment, each of the cortical depth probes 1080 include at least one elongated microelectrode elements 1085 and one discoid microelement 1086. Each of the microelectrode elements 1085 and 1086 can be used as stimulation or recording electrodes, or combined stimulation-recording electrodes. However, in the present embodiment it may be preferably to use the discoid microelectrode elements 1085 as recording electrodes because they are smaller in diameter and may capture more single-unit cellular activity. Additionally, it may be preferable to use the elongated microelectrode elements 1086 as stimulation electrodes because they are larger in diameter and can transfer more charge to the neural tissue increasing the efficacy of stimulation. In the illustrative embodiment, the microelectrode elements 1085 and 1086 spaced apart form each other in a manner to cover a wide linear depth in the cortical region.

An exemplary cortical depth probe 1090 as illustrated in FIG. 43F. The cortical depth probe 1090 includes four microelectrode elements 1095. Each of the microelectrode elements 1095 includes a respective stimulation electrode 1092 and tetrode arrangement of recording electrodes 1094. In the illustrative embodiment, discoid tetrode elements 1094 are disposed along an external perimeter of a discoid stimulation electrode 1092, such that the tetrode elements 1094 are spaced apart from the outer perimeter of the stimulation electrode 1092.

Another alternative embodiment of a cortical depth probe 1100 is illustrated in FIG. 43G. In this embodiment, each of the cortical depth probes 1100 include four microelectrode elements 1105. Each of the microelectrode elements 1105 includes a respective stimulation electrode 1102 and tetrode arrangement of recording electrodes 1104. In the illustrative embodiment, discoid tetrode elements 1104 are disposed within an open interior region of an annular stimulation electrode 1102, such that the tetrode elements 1104 are spaced apart from the inner annular perimeter of the stimulation electrode 1102.

Another alternative embodiment of a cortical depth probe 1110 is illustrated in FIG. 43H. In this embodiment, each of the cortical depth probes 1110 include four microelectrode elements 1115. Each of the microelectrode elements 1115 can be used as stimulation or recording electrodes, or combined stimulation-recording electrodes. In the illustrative embodiment, the microelectrode elements 1115 are rectangular and are spaced apart from each other in a manner to cover a wide linear depth in the cortical region.

Another alternative embodiment of a cortical depth probe 1120 is illustrated in FIG. 43I. In this embodiment, each of the cortical depth probes 1120 include at least one microelectrode element group 1125. In the present embodiment there are four microelectrode element group 1125. Each of the microelectrode element groups 1125 is composed of at least one rectangular microelectrode sub-element 1122. In this present embodiment there are four rectangular microelectrode sub-elements 1122 in each of the microelectrode element groups 1125. In some embodiments the four rectangular microelectrode sub-elements 1122 are all connected electrically, taking advantage of the edge effects to perform more efficient neurostimulation. In some embodiments the four rectangular microelectrode sub-elements 1122 are not connected electrically, and are independently stimulated.

Microelectrode element groups 1125 in addition to collective, or individual, microelectrode sub-elements 1122 can be used as stimulation or recording electrodes, or combined stimulation-recording electrodes. In the illustrative embodiment, the microelectrode element groups 1125 are rectangular groups of microelectrode sub-elements 1122 and are spaced apart from each other in a manner to cover a wide linear depth in the cortical region.

Another alternative embodiment of a cortical depth probe 1130 is illustrated in FIG. 43J. In this embodiment, each of the cortical depth probes 1130 includes at least one graded microelectrode element group 1135. Each of the graded microelectrode element groups 1135 is composed of at least one rectangular microelectrode sub-element, collectively 1132. In this present embodiment there are five rectangular microelectrode sub-elements 1132 in each of the graded microelectrode element groups 1135. The rectangular microelectrode sub-elements 1132 decrease in width and spacing toward the center of a graded microelectrode element group 1135. For example, in this manner, electrical stimulation performed can focus current to the center of such a group, while maintaining advantageous and safe electrochemical limits. For example, microelectrode sub-element $1132a$ is 300 μm wide, microelectrode sub-element $1132b$ is 100 μm wide, and microelectrode sub-element $1132c$ is 50 μm wide. In some embodiments the rectangular microelectrode sub-elements 1132 are all connected electrically, taking advantage of the edge effects to perform more efficient neurostimulation. In some embodiments the rectangular microelectrode sub-elements 1132 are not connected electrically, and are independently stimulated. Graded microelectrode element groups 1135 in addition to collective, or individual, microelectrode sub-elements 1132 can be used as stimulation or recording electrodes, or combined stimulation-recording electrodes. In the illustrative embodiment, there are two graded microelectrode element groups 1135 of microelectrode sub-elements 1132 but it is understood that more can be implemented.

In practice the operator can connect the neurological surface probe 101 to a recorder unit configured to identify certain regions of the neurological target (e.g., the brain) according to the electrical activity detected by the microelectrode elements shown in FIG. 43A through FIG. 43J. In some embodiments, the microelectrode elements used to record form the neurological target can be the same microelectrodes as those used to stimulate the target in applications in which both recording and stimulation are accomplished. Alternatively or in addition, the microelectrode elements used to record from the neurological target can be separate microelectrode elements from those used to stimulate the target. This is demonstrated in embodiments, where each cortical depth probe includes one or more recording electrodes and one or more stimulating electrodes. As shown, the dedicated recording electrodes are smaller than dedicated stimulation electrodes. In some embodiments, microelectrodes destined for recording may differ in one or more of size, shape, number, and arrangement from those microelectrodes destined for stimulation, e.g., using different microelectrodes.

CONCLUSION

Various embodiments of micro-fabricated cortical neuromodulation devices have been described herein. These embodiments are giving by way of example and are not intended to limit the scope of the present disclosure. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the disclosure.

Although some devices described herein are identified as either cutaneous or chronic, it is understood that such cutaneous devices may be used in chronically, being implanted for extended periods, or even indefinitely. Similarly, any devices described herein as being chronic, it is understood that such devices may also be used cutaneously.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to means "either or both" of the elements so conjoined, i.e. elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, or a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one or each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While this disclosure has been particularly shown and described with references to various embodiments, it will be understood by those skilled in the art that various changes in form and details may be made therein without departing from the scope of the encompassed by the appended claims.

What is claimed is:

1. An implantable probe, comprising:
a control module comprising a lower housing;
a microelectrode array film comprising:
   a proximal portion coupled with the lower housing; and
   a distal portion comprising a surface probe, the surface probe comprising a plurality of depth probe films, each of the plurality of depth probe films comprising a plurality of microelectrode elements; and
   a control circuit coupled with the proximal portion of the microelectrode array film, the control circuit comprising at least one of a stimulator, a router, an amplifier, a microprocessor, a memory, or a multiplexer; and
a supportive backing layer coupled with the distal portion of the microelectrode array film.

2. The implantable probe of claim 1, comprising:
a ribbon cable tether coupling the proximal portion of the microelectrode array film with the distal portion of the microelectrode array film.

3. The implantable probe of claim 1, comprising:
a housing comprising the lower housing and an upper housing, the housing comprising at least one fixation structure and that encloses at least a portion of the proximal portion of the microelectrode array film and the control circuit.

4. The implantable probe of claim 1, comprising:
a proximal insulative layer, a conductive layer comprising a plurality of conductive traces disposed on the insulative layer, and a second insulative layer disposed on at least a portion of the conductive layer.

5. The implantable probe of claim 4, wherein:
at least one of the plurality of microelectrode elements is in electrical communication with the control circuit via a respective one of the plurality of conductive traces.

6. The implantable probe of claim 1, wherein the microelectrode array film includes a micro-electromechanical system.

7. The implantable probe of claim 1, comprising:
the supportive backing layer coupled to the surface probe of the microelectrode array film.

8. The implantable probe of claim 7, comprising:
the supportive backing layer including a plurality of cutouts forming a plurality of backing members, each of the plurality of depth probe films arranged along a respective one of the plurality of backing members.

9. The implantable probe of claim 7, wherein a plurality of backing members protrude away from a surface of the supportive backing layer.

10. A method of stimulating a target, comprising:
implanting a probe comprising:
   a control module comprising a lower housing;
   a microelectrode array film comprising:
      a proximal portion coupled with the lower housing; and
      a distal portion comprising a surface probe, the surface probe comprising a plurality of depth probe films, each of the plurality of depth probe films comprising a plurality of microelectrode elements;
      a control circuit coupled with the proximal portion of the microelectrode array film, the control circuit comprising a stimulator;
      a supportive backing layer coupled with the distal portion of the microelectrode array film; and
energizing, with the stimulator, the plurality of microelectrode elements.

11. The method of claim 10, comprising:
positioning the surface probe of the microelectrode array film along a surface of a brain.

12. The method of claim 10, comprising:
recording a neurological activity detected by the plurality of microelectrode elements.

13. The method of claim 10, comprising:
a ribbon cable tether coupling the proximal portion of the microelectrode array film with the distal portion of the microelectrode array film.

14. The method of claim 10, comprising:
coupling at least one fixation structure of the lower housing to a skull.

15. The method of claim 10, wherein the microelectrode array film is a micro-electromechanical system.

16. The method of claim 10, wherein the probe comprises the supportive backing layer coupled to the surface probe of the microelectrode array film.

17. The method of claim 16, wherein the supportive backing layer further comprises a plurality of cutouts forming a plurality of backing members, wherein each one of the plurality of depth probe films is arranged along a respective one of the plurality of backing members.

18. The method of claim 16, wherein a plurality of backing members protrude away from a surface of the supportive backing layer.

19. The method of claim 10, comprising:
a plurality of conductive traces electrically coupling at least one of the plurality of microelectrode elements to the stimulator.

* * * * *